United States Patent
Pidgeon et al.

(10) Patent No.: US 6,602,861 B1
(45) Date of Patent: Aug. 5, 2003

(54) ACYLATED PHOSPHOLIPID DRUGS

(75) Inventors: Charles Pidgeon, West LaFayette, IN (US); Robert J. Markovich, Franklin Park, NJ (US)

(73) Assignee: Research Corporation Technologies, Inc., Tucson, AZ (US)

( * ) Notice: Subject to any disclaimer, the term of this patent is extended or adjusted under 35 U.S.C. 154(b) by 0 days.

(21) Appl. No.: 07/869,697

(22) Filed: Apr. 16, 1992

(51) Int. Cl.$^7$ ............................................. A61K 31/685
(52) U.S. Cl. ........................ 514/77; 514/78; 514/88.5; 554/78; 554/79; 554/80; 554/81
(58) Field of Search .............................. 554/79, 81, 77, 554/78, 80; 525/54.1; 536/29; 514/77, 78, 85

(56) References Cited

U.S. PATENT DOCUMENTS 4,471,113 A     9/1984     MacCoss ...................... 536/29

(List continued on next page.)

FOREIGN PATENT DOCUMENTS

EP     0 316 117     5/1989

(List continued on next page.)

OTHER PUBLICATIONS

Chemical Abstract of JP–62–205092, Sep. 1987.*

(List continued on next page.)

*Primary Examiner*—Gary Geist
*Assistant Examiner*—Deborah D Carr
(74) *Attorney, Agent, or Firm*—Scully, Scott Murphy & Presser

(57) ABSTRACT

This invention relates to a method for improving the efficiency of a drug containing a free carboxy group, the improvement comprising esterifying said carboxy group to the hydroxy group of the glycerol portion of a glycerolphospholipid ester having the formula:

$$\begin{array}{c} O \\ \parallel \\ O-P-OR \\ | \\ CH_2-CH-CH_2 \; OH \\ | \quad\;\; | \\ OR_1 \;\; OR_2 \end{array}$$

or pharmaceutically acceptable salts thereof wherein one of $R_1$ and $R_2$ is hydrogen and the other is hydrogen, a hydrocarbyl fatty acid acyl group having 4–26 carbon atoms or a hydrocarbyl heteroatom fatty acid acyl group having 3–25 carbon atoms, or $$R_4\;CH_2\;\overset{\displaystyle O}{\underset{\displaystyle R_3}{\overset{\parallel}{\underset{|}{CH-C-}}}}$$

and

R is a naturally occurring polar head group characteristic of a glycerophospholipid isolated from endogenous sources;

$R_3$ is hydrogen or lower alkyl and $R_4$ is hydrogen, hydrocarbyl containing from 1–18 carbon atoms in a principal chain and up to a total of 23 carbon atoms, said principal chain may contain 1–5 double bonds or 1–2 triple bonds; phenyl which may be unsubstituted or substituted with lower alkyl; naphthyl which may be unsubstituted or substituted with lower alkoxy; or $R_5ZR_6$;

Z is O or S; $R_5$ and $R_6$ are independently a hydrocarbyl chain containing from 1–18 carbon atoms in the principal chain and up to a total of 23 carbon atoms, said chain may be completely saturated or may contain 1–5 double bonds or 1–2 triple bonds;

and the sum of the carbon atoms in $R_3$ and $R_4$ does not exceed 23.

This invention also relates to the compounds prepared therefrom as well as the use of the compounds to treat diseases in animals.

123 Claims, 8 Drawing Sheets

U.S. PATENT DOCUMENTS

| | | | |
|---|---|---|---|
| 4,569,794 A | | 2/1986 | Smith et al. ................. 260/113 |
| 4,594,193 A | * | 6/1986 | Regen ......................... 260/399 |
| 4,814,112 A | * | 3/1989 | Paltauf et al. .............. 260/403 |
| 4,927,879 A | | 5/1990 | Pidgeon ..................... 525/54.1 |
| 4,931,498 A | | 6/1990 | Pidgeon ..................... 525/54.1 |
| 5,059,591 A | | 10/1991 | Janoff et al. .................. 514/31 |
| 5,073,571 A | | 12/1991 | Heuckeroth et al. ........ 514/557 |
| 5,082,967 A | | 1/1992 | Heuckeroth et al. ........ 562/512 |
| 5,151,445 A | | 9/1992 | Welply et al. .............. 514/557 |
| 5,158,942 A | | 10/1992 | Herrmann et al. ............ 514/77 |

FOREIGN PATENT DOCUMENTS

| | | |
|---|---|---|
| EP | 0415902 | 8/1990 |
| EP | 0 415 902 | 3/1992 |
| JP | 62-205092 | 9/1987 |
| WO | 02447 | 4/1991 |

OTHER PUBLICATIONS

Chemical Abstract, 105:187057, Hasegawa et al, "Synthesis and properties of polymerizable phospholipids", 1986.*

Sandstrom, Drugs, vol 34, p. 372–390, 1987.*

Pidgeon, et al., Immobilized Artificial Membrane Chromatography, Rapid Purification of Functional Membrane Proteins, Anal. Biochem. 194 pp. 163–173 (1991).

Chae, et al., Modern Phytochemical Methods in Recent Advances in Phytochemistry, eds. N.H. Fischer, et al., 25, pp. 149–174, 1991.

Pidgeon, et al., Photolabile liposomes as carrier, Methods Enzymol. 149, pp. 99–111 (1987).

Markovich, et al., Silica subsurface Amine Effect on the Chemical Stability and Chromatographic Properties of End–Capped Immobilized Artifical Membrane Surfaces, Anal. Chem. 63, pp. 1851–1860 (1991).

Stevens, et al., III. Characterization of Immobilized Artifical Membrane HPLC Columns Using Deoxynucleotides as Model Compounds, Biochromatog. 4, pp. 192–205 (1989).

Pidgeon, Solid phase membrane mimetics, Immobilized artificial membranes, Enz. Microb. Techn. 12, pp. 149–150 (1990).

Pidgeon, et al., U.V. Immobilized artificial membranes, Chromatography supports composed of membrane lipids, Anal. Biochem. 176, pp. 36–47 (1989).

Pidgeon, et al., Immobilized Artifical Membranes Chromatography: Surface Chemistry and Application in Applications of Enzyme Biotechnology, Plenum Press (1991).

Immobilized Artificial Membrane, Regis News, vol. 1, No. 1, pp. 1–4 and vol. 1, No. 2, pp. 1–4, 1988.

Markovich, et al., FTIR assay of hydrocarbon ligands immobilized to silica, Leaching and stability of IAM bonded phases, Anal. Biochem., 182, pp. 237–244 (1989).

Lynn, et al., Human Immunodeficiency Virus (HIV–1) Cytotoxicity: Perturbation of the Cell Membrane and Depression of PHospholipid Synthesis, Virology 163, pp. 43–51 (1988).

Aloia, et al., Lipid composition and fluidity of the human immunodeficiency virus, Proc. Natl. Acad. Sci. USA vol. 85, pp. 900–904 Feb. 1988.

Hostetler, et al., Synthesis and Antiretroviral Activity of Phospholipid Analogs of Azidothymidine and Other Antiviral Nucleosides, *J. Biol. Chem., 1990*: 265, 6112–6117.

Paige, et al., Metabolic Activation of 2–Substituted Derivatives of Myristic Acid to Form Potent Inhibitors of Myristoyl CoA:Protein N–Myristoyltransferase, Biochemistry, vol. 29, No. 46, 1990, 10566–10573.

Kishore, et al., The Substrate Specificity of *Saccharomyces cervisiae* Myristoyl–CoA:Protein N–Myristoyltransferase, The Journal of Biological Chemistry, vol. 266, No. 14, May 15, 1991, pp. 8835–8855.

Heuckeroth, et al., 11–(Ethylthio)undecanoic Acid a Myristic Acid Analogue of Altered Hydrophobicity Which is Functional for Peptide N–Myristoylation with Wheat Germ and Yeast Acyltransferase, The Journal of Biological Chemistry, vol. 263, No. 5, Feb. 15, 1988, pp. 2127–2133.

Heuckeroth, et al., Heteroatom–substituted fatty acid analogs as substrates for N–myristoyltransferase: An approach for studying both the enzymology and function of protein acylation, Proc. Natl. Acad. Sci USA, vol. 85, pp. 8795–8799, Dec. 1988.

Bryant, et al., Replication of human immunodeficiency virus 1 and Moloney murine leukemia virus is inhibited by different heteroatom–containing analogs of myristic acid, Proc. Natl. Acad. Sci USA, vol. 86, pp. 8655–8659, Nov. 1989.

Towler, et al., Protein fatty acid acylation: Enzymatic synthesis of an N–myristoylglycyl peptide, Proc. Natl. Acad. Sci. USA vol. 83, pp. 2812–2816, May 1986.

Towler, et al., The Biology and Enzymology of Eukaryotic Protein Acylation, Ann. Rev. Biochem. 1988, 57 pp. 69–99, 1989.

Towler, et al. Amino–terminal Processing of Proteins by N–Myristoylation, The Journal of Biological Chemistry, vol. 262, No. 3, Jan. 25, 1987 pp. 1030–1036.

Heuckeroth, et al., Altered membrane association of $p60^{v-src}$ and a murine 63–kDa N–myristoyl protein after incorporation of an oxygen–substituted analog of myristic acid, Proc. Natl. Acad. Sci. USA vol. 86, pp. 5262–5266, Jul. 1989.

Towler, et al., Purification and characterization of yeast myristoyl CoA: protein N–myristoyltransferase, Proc. Natl. Acad. Sci. USA vol. 84, pp. 2708–2712, 1987 Biochemistry.

Duronio, et al., Analyzing the Substrate Specificity of *Saccharomyces cerevisiae* Myristoyl–CoA:Protein N–Myristoyltransferase by Co–expressing It with Mammalian G Protein alpha Subunits in *Escherichia coli*, The Journal of Biological Chemistry, vol. 266, No. 16, pp. 10498–10504, 1991.

Duronio, et al. Protein N–myristoylation in *Escherichia coli*: Reconstitution of a eukaryotic protein modificaiton in bacteria, Proc. Natl. Acad. Sci USA vol. 87, pp. 1506–1510, Feb. 1990.

Johnson, et al. Functional analysis of protein N–myristoylation: Metabolic labeling studies using three oxygen–substituted analogs of myristic acid and cultured mammalian cells provide evidence for protein–sequence–specific incorporation and analog–specific redistribution, Proc. Natl. Acad. Sci. USA vol. 87, pp. 8511–8515, Nov. 1990.

Duronio, et al. Myristic Acid Auxotrophy Caused by Mutation of *S. cerevisiae* Myristoyl–CoA:Protein N–Myristoyltransferase, The Journal of Cell Biology, vol. 113, No. 6, Jun. 1991, pp. 1313–1330.

Rudnick, et al. Kinetic and Structural Evidence for a Sequential Ordered Bi Bi Mechanism of Catalysis by *Saccharomyces cerevisiae* Myristoyl–CoA:Protein N–Myristoyltransferase, The Journal of Biological CHemistry, vol. 266, No. 15, pp. 9732–9739, 1991.

Gordon, et al., Protein N–Myristoylation, The Journal of Biological Chemistry vol. 266, No. 14, pp. 8647–8650, 1991.

Schultz, et al., Fatty Acylation of Proteins, Ann. Rev. Cell biol. 1988, 4: pp. 611–647.

Alvarez, et al., Pancreatic Lipase–Catalyzed Hydrolysis of Esters of Hydroxymethyl Phenytoin Dissolved in Various Metabolizable Vehicles, Dispersed in Micellar Systems, and in Aqueous Suspension, Pharmaceutical Research, vol. 6, No. 7, 1989, pp. 555–563.

Huber, et al., Dietary Egg Yolk–Derived Phospholipids: Rationale for Their Benefits in Syndromes of Senescence, Drug Withdrawal, and AIDS, Phospholipids, 1990, pp. 241–255.

James, et al., Fatty Acylated Proteins as Components of Intracellular Signaling Pathways, Biochemistry, vol. 29. No. 11, Mar. 20, 1990, pp. 2623–2634.

Hostetler, et al., Phosphatidylazidothymidine, Mechanism of Antiretroviral Action in CEM Cells, J. Biol. Chem., 266, 1991; 266, 11714–11717.

Hasegawa, et al., Polymer Bulletin 1986, 15, 397–403.

* cited by examiner

AC1

AC2

1-(12-methoxydodecanoyl)-sn-3-glycerophosphatidylcholine 12-methoxydodecanoic acid

ACYLATED PHOSPHOLIPID DRUGS

This invention relates to means for improving the efficacy of a drug containing a carboxy group by esterifying the drug to a glycerol phospholipid. The present invention also relates to the product obtained therefrom and the method of using the resulting product to treat various pathological conditions in animals, especially mammals.

SUMMARY OF THE INVENTION

The present invention relates to a method for improving the efficacy of a drug containing a carboxy group or a hydrolyzable group that can be converted to a carboxy group by acylating a glycerol phospholipid ester to the drug. The present invention also relates to the resulting product and the method of using the product to treat diseases in animals, especially mammals.

More specifically, the present invention relates to a new method for improving the efficacy of a drug containing a carboxy group or the hydrolyzable group referred to hereinabove or its pharmaceutically acceptable salt by esterifying the carboxy containing drug to the glycerol backbone of a glycerol phospholipid ester, the glycerol phospholipid ester having the formula:

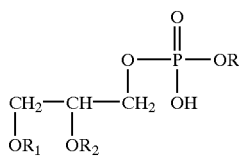

A or pharmaceutically acceptable salts thereof;

wherein one of $R_1$ and $R_2$ is hydrogen and the other is hydrogen, alkyl fatty acid acyl group having 4–26 carbon atoms or alkyl heteroatom fatty acid acyl group having 3–25 carbon atoms or

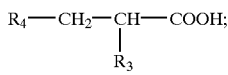

$R_3$ is hydrogen or lower alkyl and $R_4$ is hydrogen; hydrocarbyl containing from 1 to 22 carbon atoms in a principal chain and up to a total of 26 carbon atoms, said principal chain may contain 1–5 double bonds or 1–2 triple bonds; phenyl which may be unsubstituted or substituted with lower alkyl; naphthyl, which may be unsubstituted or substituted with lower alkoxy; or $R_5ZR_6$;

Z is O or S;

$R_5$ and $R_6$ are independently a hydrocarbyl chain containing from 1–21 carbon atoms in the principal chain and up to a total of 25 carbon atoms, said chain may be completely saturated or may contain 1–5 double bonds or 1–2 triple bonds, such that the sum of carbon atoms in $R_3$ and $R_4$ is not greater than 25;

R is a naturally occurring polar group characteristic of a glycerophospholipid isolated from endogenous sources; preferred examples of

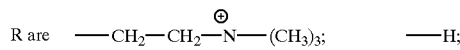

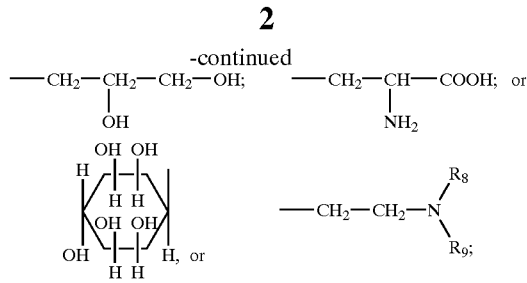

wherein $R_8$ and $R_9$ are independently hydrogen or lower alkyl, and preferably hydrogen.

The utility of the resulting phospholipid compounds from the above esterification reaction is similar to that of the drug prior to undergoing the reaction described hereinabove. Thus, the present invention is also directed to the acylated (esterified) phospholipid resulting from the acylation (esterification) reactions described hereinabove as well as the use of the acylated phospholipid for treating diseases in animals, especially mammals.

DETAILED DESCRIPTION OF THE INVENTION

Figure 1:
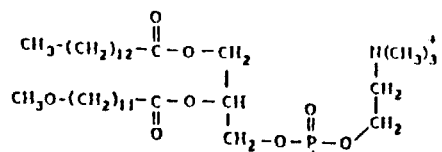
FIGS. 1(A–D) depicts the anti-HIV activity in T-cells of AC1, AC2, 1-(12-methoxydodecanoyl)-sn-3-glycerophosphatidylcholine and 12-methoxydodecanoic acid. Results are plotted on mM scale for direct comparison. Toxicity of the compounds in the CEM cells is labelled above each bar as toxic or non-toxic. The % reduction in the direct cytopathic effect of the virus (CPE) is represented on the Y-axis.
Figure 1:
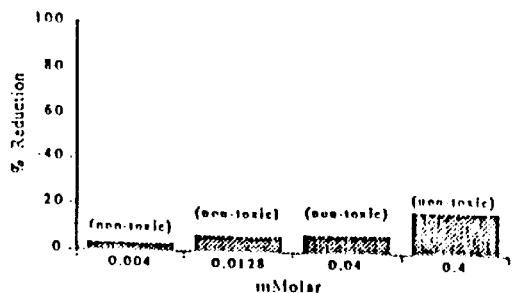
Figure 1:
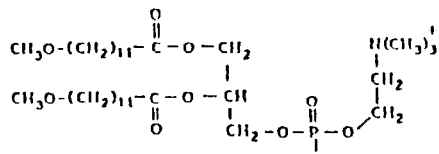
Figure 1:
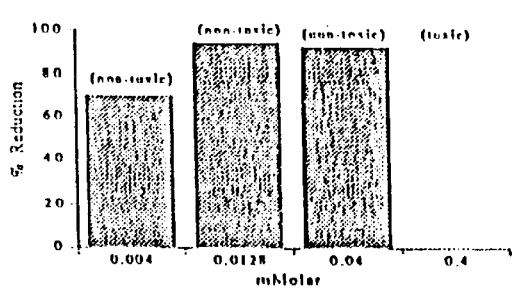
Figure 1:
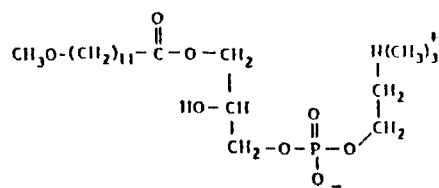
Figure 1:
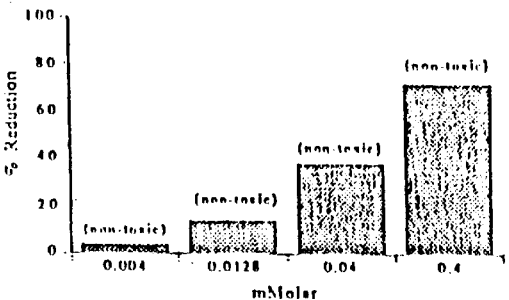
Figure 1:
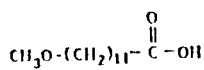
Figure 1:
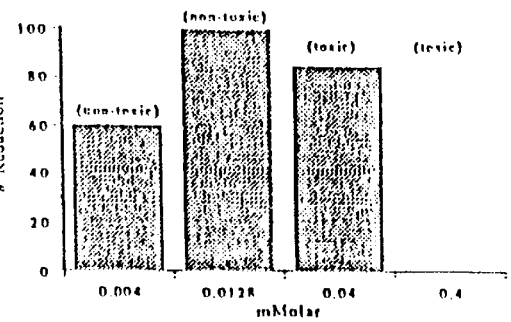

As used herein, the term "drug" refers to a chemical compound that may be used on or administered to animals, including mammals, such as man, as an aid in the diagnosis, treatment or prevention of disease or other abnormal condition for the relief of pain or suffering or to control or improve a physiologic or pathologic condition. As defined herein, the word "drug" includes the active compound or ingredient imparting the efficacious results thereto. Furthermore, the drug used in the present invention must either have a free carboxy group (—COOH—), or be its pharmaceutically acceptable salt thereof. It may also include those active compounds, such as esters and amides, that can be hydrolyzed to the COOH form without concomitant significant loss of biological activity. It also includes those drugs which can be derivatized with a carboxyl group without significant loss of biological activity.

Drugs containing free carboxy groups can be classified into various categories. These drugs are described in *Wilson and Griswold's Textbook of Organic Medicinal and Pharmaceutical Chemistry*, edited by Delgado and Remers, J. B. Lippon Cott Company, Philadelphia, 1991, pp. 1–907 and the *Merck Index*, Eleventh Edition, 1989, and are incorporated by reference as if fully set forth hereinbelow.

For example, fatty acids or their pharmaceutically acceptable salts are used as antifungal agents, i.e., drugs destructive to fungi or suppressing their reproduction or growth. These fatty acids are straight chain hydrocarbyl groups containing from 3–26 carbon atoms and may contain 1–4 internal double bonds or triple bonds. The preferred antifungal agents contain from 3–16 carbon atoms and may contain 1 or 2 internal double bonds. Examples include propionic acid, octanoic acid or 10-undecylenic acid, or the pharmaceutically acceptable salts thereof.

Drugs, as defined herein, also include antifungal agents that are polyenes which contain free carboxy groups. Examples include Amphotericin B (fungizone), Nystatin (Mycostatin, Nilstat, Mykinac, Nystex), Candicidin (Candeptin), Natamycin (pemaricin, Natacyn) and the like.

Certain antibacterial agents by virtue of their solubility properties concentrate in the urine and are effective in the treatment of infections in the urinary tract. These agents include quinoline having free carboxy groups. Examples include Nalidixic acid (1-ethyl-1,4-dihydro-7-methyl-4-oxo-1,8-naphthyridine-3-carboxylic acid), Cinoxacin (1-ethyl-1,4-dihydro-4-oxo-[1,3]-dioxolo-[4,5 g]-cinnoline-3-carboxylic acid), Norfloxacin (1-ethyl-6-fluoro-1,4-dihydro-4-oxo-7-(1-piperazinyl)-3-quinoline carboxylic acid), Enoxacin, Ciprofloxacin, Perfloxacin, Amifloxacin and the like.

Other antibacterial agents, especially the B-lactam antibacterial agents, and the penicillins also contain free carboxy groups. Examples include Penicillin G (Benzylpenicillin), Penicillin V (Phenoxymethylpenicillin), Methicillin (2,6-Dimethoxyphenylpenicillin), Nafcillin (2-ethoxy-1-naphthylpenicillin), Oxacillin (5-Methyl-3-phenyl-4-isoxazolylpenicillin), Cloxacillin (5-methyl-3-(2-chlorophenyl)-4-isoxazolylpenicillin), Dicloxacillin (5-methyl-3-(2,6-dichlorophenyl)-4-isoxazolylpenicillin), Ampicillin (D-α-Aminobenzylpenicillin), Amoxicillin (D-α-amino-p-hydroxybenzylpenicillin), Cyclacillin (1-aminocyclohexylpenicillin), Carbenicillin (α-carboxybenzylpenicillin), Ticarcillin (α-carboxy-3-thienylpenicillin), Piperacillin (α-(4-ethyl-2,3-dioxo-1-piperazinylcarbonlamino)benzylpenicillin), Azlocillin (α-(2-oxoimidazolidinocarbonylamino)benzylpenicillin), Mezlocillin (α-(1-methanesulfonyl-2-oxoimidazolidinocarbonylamino)-benzylpenicillin), the pharmaceutically acceptable salts thereof and the like.

Other β-lactam antibiotics include Clavulanic acid or the Potassium salt thereof, 1,1-dioxopenicillanic acid (Sulbactam), carbapenems, such as thienamycin, the cephalosporins, such as Cephalexin, Cephradine, Cefadroxil, Cefaclor, Cephalothin, Cephaprin, Cefazolin, Cefamandole, Cefonacid, Ceforanide, Cefuroxime, Cefotaxime, Ceftizoxime, Ceftriaxone, Ceftazidime, Cefoperazone, Cefoxitin, Cefotetan, and Moxalactam, the pharmaceutically acceptable salts thereof and the like.

Anti-inflammatory analgesics, especially acetylsalicylic acid and their acid salts are also examples of drugs that can be used in accordance with the present invention. Other analgesics that could be used in the present invention include the N-arylanthranillic acids, such as Mefenamic acid (N-2,3-xylylanthranillic acid), meclofenamate and the like; the arylacetic acid derivatives, such as Indomethacin (1-p-chlorobenzoly)-5-methoxy-2-methylindole-3-acetic acid), Sulindac ((Z)-5-fluoro-2-methyl-1-[[p-methylsulfinyl) phenyl]methylene]-1H-indene-3-acetic acid), Tolmetin (1-methyl-5-(p-toluoyl) pyrrole-2-acetate dihydrate sodium), Zomepirac (5-(4-chlorobenzoyl)-1,4-dimethyl-1H-pyrrole-2-acetate dihydrate sodium), Ibufenac, Ibuprofen (2-(4-Isobutylphenyl) propionic acid, Namoxyrate (2-(4-Biphenyl) Butyric acid dimethylaminoexhanol salt), Naproxen ((+)6-Methoxy-α-methyl-2-naphthalene-acetic acid), Fenoprofen calcium (α-Methyl-3-phenoxybenzene acetic acid dihydrate calcium) (Nalfon), S-adenosylmethione, Alminoprofen, Amfenac, Benoxaprofen, Bucloxic acid, Carprofen, Etodolac, Felbinac, Fentiazac, flufenamic acid, Flunixin, Flunoxaprofen, Indoprofen, Isoxepac, Ketoprofen, Ketorolac, Loxoprofen, Oxaprozin, Protizinic acid, Sulindac, Suxibozone, Tiaprofenic acid, Tolfenamic, Tolmetin, Zomepirac, Chromolyn, the pharmaceutically acceptable salts thereof and the like.

Antihypertensive agents containing a carboxy group can also be used in the present invention. Examples include Alacepril, Captopril, Cilazapril, Enalaprilat, Lisinopril, and the like.

Anti-ulcer drugs, such as Cetraxat, Rosaprostol and the like can also be used in the present invention.

Anti-cancer drugs and anti-metabolites containing a carboxy group can also be used in the present invention. Examples include folic acid, aminopterin, methotrexate, homofolic acid, Baker's Antifol, 10-ethyl-10-deazaaminopterin, and the like.

As used herein, the term "drug" also includes heteroatom fatty acids, as defined hereinbelow. A preferred class of the heteroatom fatty acids are oxy and thio-substituted fatty acid analog substrates of myristoylating enzymes, which analogues contain at least one oxygen or sulfur in place of a methylene group in a carbon position from 4 to 13 in a fatty acid chain of a 13–14 carbon atoms. The hetero-atoms fatty acids have been shown to be useful in the treatment of retroviral infections. These compounds are also drugs as defined herein. These oxy and thio-substituted fatty acid analogs are described in European Patent Application 415, 902.

It is preferred that the drugs that are to be utilized in the present invention are fatty acids or the thio or oxy substituted fatty acid and analogs described hereinabove. Other preferred drugs include the arylacetic acids derivatives, such as ibuprofen and naproxen and the like. The most preferred drugs have the formula:

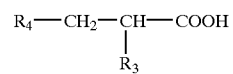

wherein $R_3$ is hydrogen or lower alkyl and
$R_4$ is hydrogen; hydrocarbyl containing from 1 to 22 carbon atoms in a principal chain and up to a total of 26 carbon atoms, said principal chain may contain 1–5 double bonds or 1–2 triple bonds; phenyl which may be unsubstituted or substituted with lower alkyl; naphthyl, which may be unsubstituted or substituted with lower alkoxy; or $R_5ZR_6$;
Z is O or S;
$R_5$ and $R_6$ are independently a hydrocarbyl chain containing from 1–21 carbon atoms in the principal chain and up to a total of 25 carbon atoms, said chain may be completely saturated or may contain 1–5 double bonds or 1–2 triple bonds, such that the sum of carbon atoms in $R_3$ and $R_4$ is not greater than 25.

As used herein, the pharmaceutically acceptable salts include the acid and basic salts. Basic salts for pharmaceutical use are potassium, sodium, calcium, magnesium, zinc and the like. Suitable acids include for example, hydrochloric, sulfuric, nitric, benzenesulfonic, toluenesulfonic, acetic, maleic, tartaric and the like which are pharmaceutically acceptable.

The term "lower alkyl" refers to an alkyl group containing from 1 to 6 carbon atoms and may be straight chain or branched. It includes such groups as methyl, ethyl, propyl, isopropyl, butyl, sec-butyl, isobutyl, t-butyl, pentyl, amyl, hexyl and the like. The preferred lower alkyl group is methyl.

The term hydrocarbyl refers to an aliphatic group which contains only carbon and hydrogen atoms in the principal chain. It may contain 1–5 multiple bonds, such as double or triple bonds, although preferably it contains 1–2 double bonds or triple bonds. Preferably the multiple bond is a double bond. The hydrocarbyl group contains 1 to 22 carbon atoms in a principal chain, but may contain branches of alkyl group substituents, with the total number of carbon atoms in the hydrocarbyl group being no greater than 26. When at least one of the methylene groups ($CH_2$) on the hydrocarbyl principal is replaced by O or S, then the term "heteroatom hydrocarbyl" shall be used. When one of the methylene groups is replaced by O or S, the heteroatom hydrocarbyl shall contain no greater than 21 carbon atoms in the principal chain. Furthermore, the hydrocarbyl as well as the heteroatom hydrocarbyl chain may be unsubstituted or substituted with such groups as halo or hydroxy, lower alkoxy, lower alkylthio, and the like.

The term "fatty acid" shall mean a carboxylic acid derived from or contained in animal or vegetable fat or oil. Said fatty acids may be saturated or unsaturated and are composed of a chain of alkyl groups containing from 4 to 26 carbon atoms, usually even numbered. The fatty acids are characterized by a terminal carboxy group. They also may contain a hydroxy group or a second carboxy group. It is preferred that the second carboxy group, when present, is located at the omega (last) carbon position of the principal chain.

Examples of fatty acids are described in SCIENTIFIC TABLES, 7th Edition, published by CIBA-Geigy Limited, Basle Switzerland, p. 365–372 (1970), and the contents are incorporated by reference as if fully set forth herein. These examples include the natural product fatty acids, such as propionic acid, n-butyric acid, valeric acid, caproic acid, enanthic acid, caprylic acid, pelargonic acid, capric acid, undecylic acid, lauric acid, margaric acid, stearic acid, nondecylic acid, arachidic acid, heneicosanoic acid, behenic acid, tricosonoic acid, lignoceric acid, pentacosanoic acid, cerotic acid, acrylic acid, trans-(α)-crotonic acid, iso(β)-crotonic acid, $\Delta^2$ hexenoic acid, $\Delta^4$-decenoic acid, $\Delta^9$-dodecenoic acid, $\Delta^4$ dodecenoic acid, $\Delta^6$-dodecenoic acid, tsuzuic acid, physteric acid, myristoleic acid, palmitoleic acid, petroselinic acid, oleic acid, eladic acid, trans- and cis-vaccenic acid, $\Delta^{12}$-octadecenoic acid, gadoleic acid. $\Delta^{11}$-eicosenoic acid, cetoleic acid, erucic acid, brassidic acid, selacholeic acid, ximenic acid, sorbic acid, linoleic acid, hiragonic acid, α-eleosteric acid, β-eleostearic acid, linolenic acid, stearidonic acid, arachidonic acid, behenolic acid, isobutyric acid, isovaleric acid, tiglic acid, isomyristic acid, anteiomargic acid, tuberculostearic acid, phytanic acid, myocolipenic acid, myococeranic acid, and the like. Preferably, the term fatty acid as used herein shall contain 10 to 22 carbon atoms, and more preferably shall contain 13 to 18 carbon atoms. Most preferably, the fatty acid shall contain 4–8 carbon atoms or 13–15 carbon atoms.

As used herein, the term "fatty acyl of a fatty acid" is defined as a fatty acid in which the carboxy terminus is replaced by an acyl group

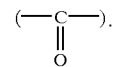

In other words, said term has the formula

wherein $R_7$ is a is a hydrocarbyl group as defined herein. For example, the fatty acyl of myristic acid is

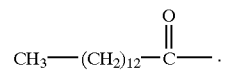

The term heteroatom fatty acid is a fatty acid containing from 3 to 25 carbon atoms containing at least one oxygen or sulfur in the principal chain. The heteroatom fatty acid may be saturated or contain one or two multiple bonds, especially double bonds. The heteroatom fatty acid may be straight-chained or branched, but it is preferred that it is straight-chained. These heteroatom fatty acids may contain more than one oxy group or thio group or combination thereof. It is preferred, however, that the heteroatom fatty acid contain 1–3 oxygen or sulfur atoms or a combination thereof. It is especially preferred that the heteroatom fatty acid contains one sulfur or oxygen atom and it is most preferred that the heteroatom fatty acid contain one oxygen atom.

A preferred class of the heteroatom fatty acid is a biologically active fatty acid analog of myristic acid chosen from a saturated or partially unsaturated fatty acid containing 13–14 carbon atoms, wherein at least one methylene group normally present at position 4 to 13 is replaced by one oxygen or sulfur or combination thereof. It is especially preferred that only one methylene group is replaced by oxygen or sulfur and it is most preferred that said methylene group is replaced by oxygen.

Preferred heteroatom fatty acids employable in the present invention include but are not limited to: 11-(ethylthio)undecanoic acid [$CH_3CH_2S(CH_2)_{10}COOH$]; 5-(octylthio)pentanoic acid [$CH_3(CH_2)_7S(CH_2)_4COOH$]; 11-(methoxy)undecanoic acid [$CH_3O(CH_2)_{10}OCOOH$]; 11-(ethoxy)undecanoic acid [$CH_3CH_2O(CH_2)_{10}COOH$]; 12-(methoxy)dodecanoic acid [$CH_3O(CH_2)_{11}COOH$]; 10-(propylthio)decanoic acid [$CH_3(CH_2)_2S(CH_2)_9COOH$]; 10-(propoxy)decanoic acid [$CH_3(CH_2)_2O(CH_2)_9COOH$]; 11-(1-butoxy)undecanoic acid [$CH_3(CH_2)_3O(CH_2)_{10}COOH$]; [10-(2-propynoxy)decanoic acid [$HC{\equiv}CCH_2O(CH_2)_9COOH$]; and the like.

Additionally, the term heteroatom fatty acid is a saturated or unsaturated $C_4$ to $C_{26}$ fatty acid which is substituted by halo, hydroxy, alkoxy, mercapto or alkylthio. More preferably, the heteroatom fatty acid is a saturated or unsaturated fatty acid containing 13 to 16 carbon atoms which is substituted with halo, or hydroxy. More preferred heteroatom fatty acids are saturated or unsaturated fatty acids which contain 13 to 14 carbon atoms and are substituted by chloro, bromo or hydroxy. Still more preferred are saturated or unsaturated fatty acids which contain 13 to 14 carbon atoms which are substituted by chloro, bromo or hydroxy at the 2-position.

Additionally, it is to be understood, within the spirit and scope of the present invention, the term heteroatom fatty acid may also be a $C_4$ to $C_{26}$ saturated or unsaturated fatty acid wherein a methylene group normally at carbon position 5 to 21 is replaced by oxygen or sulfur, and further, said fatty acid may be substituted, preferably at the 2-position, by halo, hydroxy, alkoxy, mercapto or alkylthio.

The term "alkyl heteroatom fatty acid acyl group" as defined herein is defined as a heteroatom fatty acid in which the carboxy terminus is replaced by an acyl group

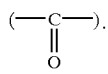

As used herein, the term halo shall mean one or more members of Group VII A of the periodic table, including fluorine, chlorine, bromine, and iodine; most preferably, fluoro or chloro and especially bromo.

The term alkoxy denotes an o-alkyl group, wherein alkyl is defined hereinabove. Examples of alkoxy are methoxy, ethoxy, propoxy, butoxy, pentoxy, hexoxy, and the like.

The term alkylthio is defined as an alkyl, as hereinbefore defined, containing a thio group.

The term mercapto shall mean HS.

The term "omega (w) carbon" refers to the last carbon in the principal chain.

The term penultimate carbon refers to the next to last carbon on the principal chain. For example, in the decyl substituent, $C_{10}$ is the omega carbon while $C_9$ is the penultimate carbon.

The term "heteroatom is bonded to the penultimate carbon" or any equivalence thereof, means that the heteroatom is bonded between the omega and penultimate carbon. For example, if Z is a heteroatom, and if it is stated that Z is bonded to the penultimate carbon, this means that in the principal chain, Z is located between the last and the next to last carbon:

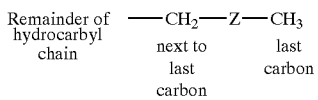

As defined herein, R is part of the polar head group and is a distinguishing portion of a glycerophospholipid. The polar group may be naturally occurring or analogs thereof. There are many types of polar groups on glycerol phospholipids found in nature. The more common R groups thereon are inositol, ethanolamine, choline and serine. But recently other head groups have been found, e.g., N-methyl ethanolamine, N,N-dimethyl ethanolamine, (See Casal et al., *Biochemica et Biophysica Acta*, 1983, 735, 387–396), and sulfocholine, (See Mantsch et al. *Biochemical et Biophysica Acta*, 1982, 689, (63–72) and the like. The present invention contemplates these groups found in naturally occurring glycerophospholipids and analogs thereof.

The polar groups used herein have a dipole moment. These polar groups may contain heteroatoms, such as O, S or N or P. In fact, they may contain more than 1 heteroatom, e.g., 2, 3, 4, 5 or 6–9. Thus, there may be as many as 8 or 9 heteroatoms present in the R group. The polar head group may be a natural sugar (e.g., inositol) or combination of natural sugars (e.g., inositol-glycon) or the R group may consist of an alkylene chain in which a methylene group is replaced by a heteroatom or a heteroatom lower alkyl (N—$CH_3$, e.g.) or heteroatom diloweralkyl [e.g. $S(CH_3)_2$], or if the heteroatom is nitrogen, a triloweralkyl heteroatom. Examples include inositol, ethanolamine, choline, sulfocholine, serine, a N-methyl ethanolamine, N,N-dimethyl-ethanolamine, and the like.

The prefix "sn-" as employed herein is used to denote the carbons of the glycerol backbone of the fatty acid according to the stereospecific numbering system established for lipid nomenclature. In other words, sn-1 denotes the carbon at the first position, sn-2 denotes the carbon at the second position, etc.

The phospholipid ester depicted hereinabove can exist in two forms,

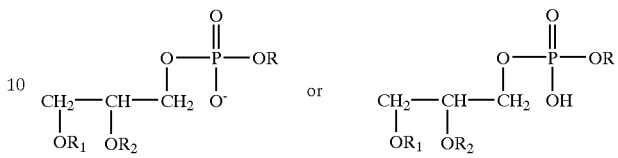

The term "basic salts" contemplates the former form, wherein basic salts are as defined herein.

The carbon atom at the sn-2 position of the phospholipid ester depicted hereinabove contains an asymmetric center. Thus, the phospholipid ester as well as the drug derived therefrom may exist in two stereochemical configurations, the L-stereoisomeric form (the natural configuration) or the D- form. Both stereoisomeric forms are contemplated by the present invention.

Of course, there may be additional chiral centers present on the R, $R_1$ and $R_2$ groups which also gives rise to various stereoisomeric forms. These various stereoisomeric forms are also contemplated to be within the scope of the invention. Therefore, all of the various configurations around each chiral center in the phospholipid drug, including the various enantiomers and diastereomers as well as racemic mixtures and mixtures of enantiomers, diastereomers or both are contemplated by the present invention. If there are any chiral centers on $R_1$ and $R_2$, it is preferred that the configuration at the carbon centers be in the same configuration as the drug with which it is reacted.

As employed herein, the term "improving" the efficacy refers to ameliorating or enhancing the pharmacokinetics of a drug, i.e. stability, metabolism, absorption or distribution of the drug. This enhancement of the drug results from the formation of the phospholipid compound in accordance with the acylation reaction described hereinabove. The phospholipid compound, in accordance with the present invention may be, for example, more potent and may have greater activity than the drug relative to a particular utility, as measured by standard assays known to one skilled in the art.

The nonacylated drugs may have deleterious side effects such as they may be toxic to the cell or it may be metabolized into molecules that may be toxic to the cell. However, by acylating the drug onto a glycerol phospholipid, in accordance with the present invention, the resulting molecules are frequently less toxic to the cell than the non-reactive cell. Thus, greater amounts of the acylated compound can be administered to the cell relative to the non-reacted form. The administration of phospholipid drug derivatives of the present invention to the animal provides a less toxic method to introduce biologically active molecules or drugs into cells. Thus, the term improving the efficacy of the drug includes the reduction of toxicity when the drug is reacted to form the phospholipid derivative, in accordance with the present invention.

The formation of the phospholipid derivative may serve an additional advantage. Certain drugs are unable to reach diseased areas because of the inability to permeate the cellular membrane. Biological membranes consist mainly of lipids and proteins, and the drug phospholipids of the present invention may more easily permeate the cellular membrane and enter the cell than the corresponding non-phospholipid drug. Consequently, by transforming the drugs into the drug phospholipids in accordance with the present invention, the inventors have found a way to allow a drug to more quickly enter the diseased cell and impart its effect on the diseased state. Thus, it may require less time to achieve a desired effect when using the phospholipid drug of the present invention relative to the non-reacted drug. This characteristic is also included in the term "improving the efficacy" of the drug.

Furthermore, the phospholipid derivatives prepared in accordance with the present invention may be useful in controlling the delivery of drugs to the target cells. As indicated hereinabove, the drug phospholipid prepared in accordance with the present invention facilitate the permeation of the drug across the cell membrane into the target cell. As indicated hereinbelow, phospholipids of the present invention may form liposomes. Liposomes are common vehicles for the sustained release of pharmaceuticals. In those cases where the target cell utilizes the non acylated drug, the acylation of the drug to the phospholipid in accordance with the present invention permits the non-acylated drug to be slowly released at the target site of the cell. Without wishing to be bound, it is believed that the phospholipases may slowly release the drug from the phospholipid through hydrolysis. This characteristic.may be extremely useful in cases where the non-acylated drug may have deleterious side effects, e.g. toxic to the cell at higher concentrations; through the acylation reaction described herein, the inventors have, in effect, found a vehicle to allow these non-acylated drugs to be utilized by the cells at higher concentrations.

Another advantage of the phospholipid drug relative to the non-reacted drug is its unique ability for drug targeting. The disposition of the phospholipid drug can be somewhat controlled. For example, in the case of the drug being a fatty acid or heteroatom fatty acid, single chain phospholipid analogs tend to form micelles while double chain phospholipid analogs tend to form liposomes. It has been shown that after injection into animals or man, liposomes will concentrate in macrophages, and micelles will not. Micelles do not concentrate in the reticular endothelial system, while liposomes are targeted mostly to the reticulo-endothelial system. Many liposomes, for example, are passively targeted to the liver, spleen and lung. Furthermore, by controlling the head group, further control of cellular disposition of the phospholipid drug can be maintained. For example, lipids with phosphatidylserine head groups cross the blood brain barrier and may be useful in treating diseases in the brain. Furthermore, the diacylated lipid analog may be useful for treating HIV infected macrophage during active viremias; and the single chain phospholipid may be more acceptable for treating non-macrophage cells, such as T-cells. On the other hand, phospholipids with phosphatidylethanolamine head group can form micelles (if single chain) or inverted hexagonal (if double chained) and may be more evenly distributed through the body. Thus, the phospholipid drugs containing biologically active fatty acid molecules in the alkyl chains can be modified such that the dispersion properties of the phospholipids can be used to control, in part, the in vivo disposition. This ability to control the disposition is not available with the non-phospholipid drug. Thus, less active ingredient of the phospholipid drugs of the present invention would be necessary to be given to the patient relative to the non-reacted drug in order to obtain a given effect.

Moreover, the phospholipid drug may be the more stable form in vivo relative to the non-acylated form. Thus, by acylating the drug to the glycerophospholipid in accordance with the present invention, a means in promoting the in vivo stability of the non-acylated drug could be achieved.

The term "acylating" as defined herein refers to an esterification reaction between the carboxy group of the drug and a hydroxy group on the sn-i or sn-2 position of the glycerol backbone under esterification conditions, as defined hereinbelow.

Compounds resulting from the acylating reactions (esterification) can be prepared in accordance with art-recognized techniques. Exemplary procedures are described below.

The drug having a carboxy group that is activated by standard methods for acylation may be reacted with the hydroxy group on the glycerol backbone. The reaction may be run in inert solvents that will dissolve both reagents or it may be run in a biphasic solvent. Examples include DMSO, crown ethers and the like. The reaction is run at temperatures facilitating acylation. These temperatures may range from room temperature to the reflux temperature of the solvent, although it is preferred that the reaction is run at about room temperature or slightly above. Furthermore, the reaction may be run under reduced pressure, such as under vacuum.

Alternatively, the reaction may be run by first converting the acid to an acylating derivative, such as the acid halide (e.g., acid chloride, acid bromide) or anhydride, under reaction conditions known to one skilled in the art. The acylated derivative is then reacted with the hydroxy group on the glycerol backbone of the glycerol phospholipid under esterification conditions as described hereinabove. In other words, the reaction may be run in an inert solvent that will dissolve both regents or it may be run in a two-phase solvent system. The reaction is run at temperatures facilitating acylation. These temperatures may range from room temperature to the reflux temperature of the solvent, although it is preferred that the reaction is run at about room temperature or slightly above. Further, the reaction may be run under reduced pressure.

The reactions described hereinabove can be schematically represented as follows:

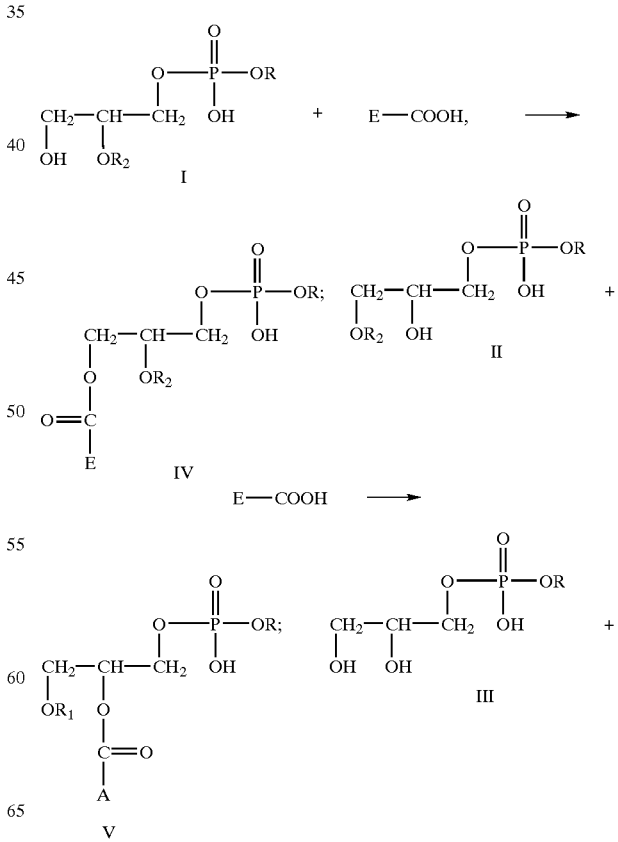

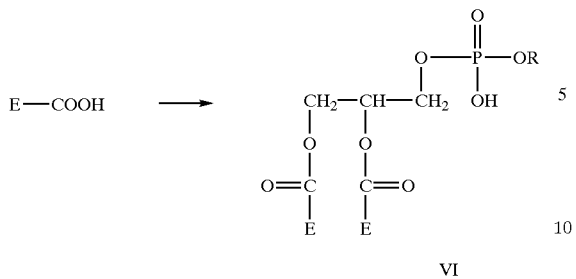

In the above schemes, $R_1$, $R_2$ and $R$ are as defined hereinabove and E—COOH is the drug having the free carboxy group.

Compounds of Formula III are either available commercially or can be prepared by art recognized methods.

Compounds of Formula II wherein $R_1$ is other than hydrogen can be prepared from compounds of Formula III as follows:

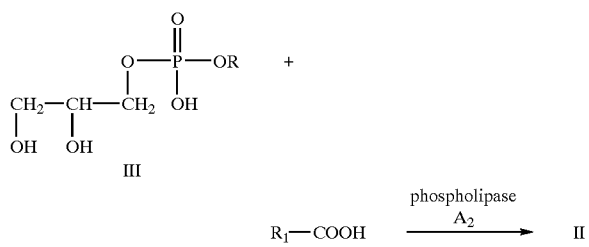

Acylation of III with an excess of acylating derivative of $R_1$—COOH (e.g., the acid halide, anhydride or acid) under esterification conditions will produce the diacylated compounds. The esterification conditions are similar to those described hereinabove. Hydrolysis of the acylated compound with phospholipase $A_2$ will produce the compound of Formula II.

Similarly, compounds of Formula I wherein $R_2$ is other than hydrogen can be prepared from compounds of Formula III as follows:

$$III + R_2\text{—COOH} \xrightarrow{\text{phospholipase } A_1} I$$

Acylating III with an excess of an acylating derivative of $R_2$—COOH (e.g., the acid halide, anhydride or acid) under esterification conditions as described hereinabove will produce the diacylated compounds. Hydrolysis of the diacylated compounds with phospholipase A will produce the compound of Formula I.

In both cases described hereinabove, the acid halide can be prepared from the corresponding acid with thionyl chloride or bromide. Similarly, the anhydride can be prepared from the corresponding acid by reacting the acid with a dehydrating agent, such as $P_2O_5$ or dicyclohexylcarbodiimide. Alternatively, the anhydride can be prepared by reacting the acid halide with the corresponding salt of the acid.

Furthermore, diacylated analogs containing either a glycerol (PG), serine (PS) or ethanolamine (PE) headgroup can be synthesized by transphosphatidylation using phospholipase D treatment of diacylated phosphatidyl choline analogs, as described hereinbelow.

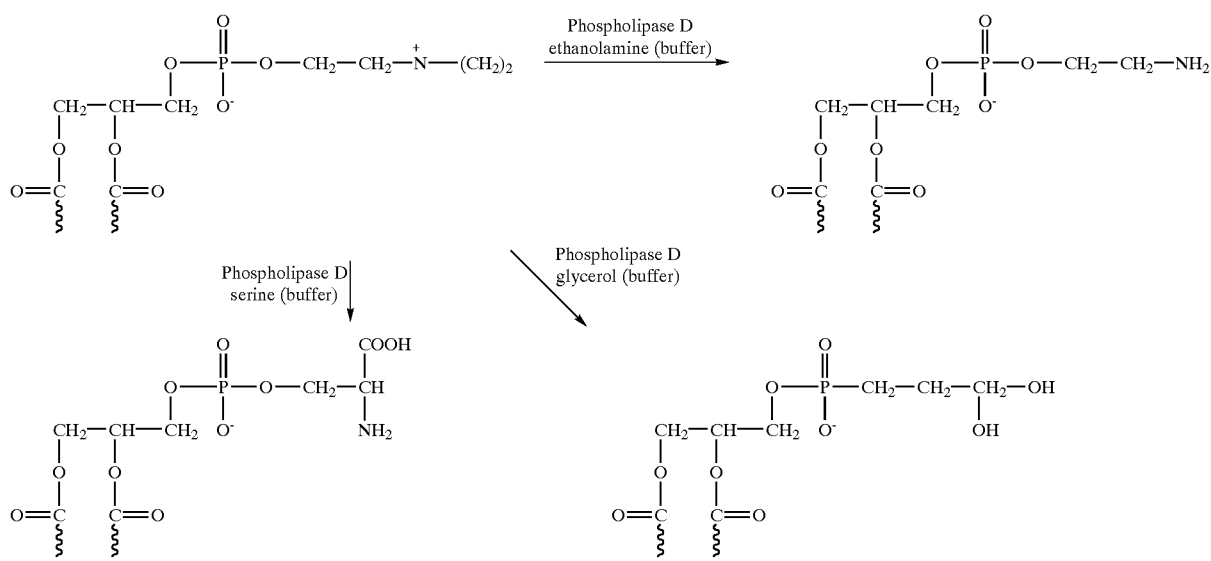

wherein { represents the remainder of the fatty acid chain. The transphosphatidylation with phospholipase is D effective with both the L- and D- stereoisomers of the glycerophospholipid. Cleavage with phospholipase $A_1$ or phospholipase $A_2$ of the L-isomer will produce the 1-hydroxy or 2-hydroxy analog, respectively.

The acylating derivative of the drug containing the carboxy group can be prepared in accordance with art-recognized procedures. For example, the acid chloride can be prepared by reacting the drug with thionyl chloride. The anhydride can be prepared by reacting the drug containing a free carboxy group with a dehydrating agent, such as $P_2O_5$ or dicyclohexylcarbodiimide, acetic anhydride, trifluoroacetic anhydride, methoxyacetylene and the like. Alternately, the anhydride can be prepared by treating the acid halide (such as acid chloride) of the drug with the acid salt of the drug.

Alternatively, and especially in the case of the phospholipid drugs of myristic acid derivatives, the phospholipid drug can be prepared using immobilized artificial membranes (IAM), as described in Markovich, et al. in *Anal Chem.*, 1991, 63, 1851–1860, the contents of which are incorporated herein by reference. The procedure will be described in more detail hereinbelow. Generally, the glycerol phospholipid of the formula:

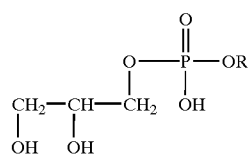

(hereinafter referred to as GP) wherein R is as defined hereinabove (1 mMol) is solubilized in MeOH (0.5–2.0 ml) and is adsorbed onto an IAM packing material, prepared as described hereinbelow by dropwise addition of the methanolic-PC solution. The MeOH was allowed to evaporate after the IAM surface was completely loaded with GP. The IAM/GP solid material was dried overnight in a vacuum at 45° C. After drying, the IAM/GP powdered was suspended in dry chloroform containing the dried acylating derivative of the drug (acid halide, anhydride, and the like) and dried equivalent of a catalyst, such as dimethylaminopyridine and the like.

The monoacylated phospholipid compounds of the present invention (lyso form) can also be prepared from the diacylated phospholipids by using the appropriate phospholipase. For example, phospholipase $A_2$ selectively hydrolyzes the ester at the $sn_2$ position of the glycerol backbone to form a compound having the Formula II hereinabove:

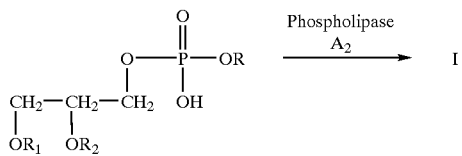

In the above scheme, R, $R_1$ and $R_2$ are as defined hereinabove, except that $R_1$ and $R_2$ are not hydrogen.

Similarly, the other lyso form having Formula I can be prepared from the diacylated phospholipid by using phospholipase $A_1$, which selectively hydrolyzes the ester at the $sn_1$ position of the glycerol backbone:

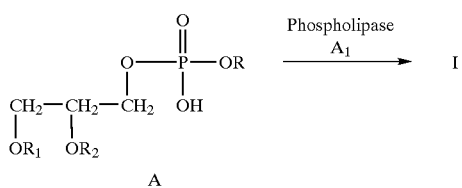

Finally, the compound of Formula IV can be prepared by hydrolysis of I with phospholipase $A_2$, hydrolysis of II with phospholipase $A_1$ or hydrolysis of A with phospholipase $A_1$ and phospholipase $A_2$ in either order. It is to be noted that in the above schemes, R, $R_1$ and $R_2$ are as defined hereinabove, except that $R_1$ and $R_2$ are not hydrogen.

In the acylation reactions described above, $A_1$ COOH or $A_2$ COOH may be unsubstituted or substituted. If substituted, it is preferred that the substitution is on the α carbon (the carbon atom adjacent to the carboxy group). Further, the preferred substituents are hydroxy, lower alkoxy, mercapto or alkyl thio.

These compounds can be prepared from art recognized techniques. For example, the α-hydroxy compound can be prepared from the corresponding α-halo carboxylic acid by reacting the latter with base (OH—) under substitution reaction conditions. Furthermore, the mercapto compound can be prepared from the corresponding α-halo carboxylic acid by reacting the latter compound with $HS^-$ under substitution reaction conditions, while the α-alkylthio carboxylic acid can be prepared from the corresponding α-halo carboxylic acid by reacting the latter with lower alkylthiolate under substitution reaction conditions. The α-lower alkoxy derivative can be prepared by reacting the α-halo carboxylic acid with lower alkoxide under Williamson reaction conditions.

The α-halo carboxylic acid can be prepared by reacting $E_1$ COOH (or $E_2$ COOH) with phosphorous and halogen (preferably $Cl_2$ or $Br_2$) or phosphorus trihalide under Hell-Volhard-Zelinsky reaction condition as described hereinbelow on Pages 53–54. Alternatively, the α-halo carboxylic acid can be prepared from the malonic acid ester synthesis described hereinbelow on Page 54–55.

It is to be understood that in some of the reactions described hereinabove, it may be necessary to employ protecting groups on reactive functional groups, such as hydroxy, that may be present. The protecting groups to be employed are obvious to one skilled in the art. Examples of various protecting groups can be found in "Protective Groups in Organic Synthesis" by T. W. Green, John Wiley and Son, 1981, which is incorporated herein by reference.

In the reactions described hereinabove, the various products can be separated and purified by art recognized techniques known to one skilled in the art, such as flash chromatography or HPLC.

The phospholipid compounds resulting from the above reactions can be used to treat diseases in animals, especially mammals, by administering to said animal an effective amount of the compound to treat said diseased state. As indicated hereinabove, the compounds resulting from the reaction described hereinabove are compounds having formula IV–VI, as described hereinabove. The present invention is directed to those compounds as well as the use of the compounds in treating diseases. It is to be noted that the compounds prepared from the present invention have a similar utility as the drug, as defined herein, from which it is prepared.

Thus, the following compounds are prepared from reactions described hereinabove:

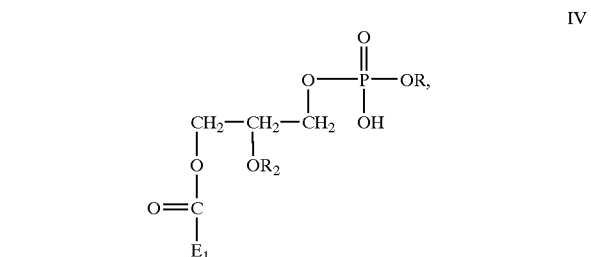

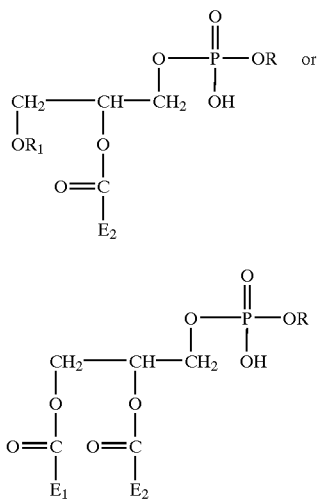

or pharmaceutically acceptable salts thereof; wherein $R_1$, $R_2$ and R are as defined hereinabove and $E_1$ and $E_2$ are drug molecules as defined hereinabove less the respective carboxy groups. (In other words, $E_1$ COOH and $E_2$ COOH represent drug molecules having a free carboxy group.) It is preferred that when $E_1$ and $E_2$, are present that $E_1$ and $E_2$ have the same meaning. As used herein, the term "drug" is as defined hereinabove. However, it is preferred that for compounds of Formula IV, $R_2$ is not hydrogen or an alkyl fatty acid acyl group when $E_1$ is acylic hydrocarbyl group having 4–26 carbon atoms. Furthermore, it is preferred that for compounds of Formula V, $R_1$ is not hydrogen or an alkyl fatty acid acyl group when $E_2$ is an acylic hydrocarbyl group having 4–26 carbon atoms. Finally, in Formula VII, it is preferred that $E_1$ and $E_2$ are both not acylic hydrocarbyl groups having 4–26 carbon atoms.

It is to be noted that when $R_2$ or $R_1$ is hydrogen in compounds of Formula IV or V respectively, these compounds represent the lysophospholipids of the present invention.

In the compounds of Formula IV–VII, the carbon atom at the sn-2 position is a chiral center and can therefore exist in two stereochemical configurations, the L-configuration or the D-configuration. Both stereoisomeric forms are contemplated by the present invention.

Of course, there may be additional chiral centers present on $E_1$, $E_2$, $R_1$, $R_2$ and R which also gives rise to various stereoisomeric forms. These various stereoisomeric forms are also contemplated to be within the scope of the invention. Therefore, all of the various stereochemical forms around each chiral center including the various enantiomers and diastereomers as well as racemic mixtures and mixtures of enantiomers, diastereomers or both are contemplated to be within the scope of the present invention. It is preferred, however, that the R group be in the L-configuration.

It is preferred that when $R_2$ or $R_1$ is other than hydrogen, $R_2$ and $R_3$ are not branched, but are straight chained.

In a preferred embodiment, $E_1$ or $E_2$, whenever present, is an heteroatom hydrocarbyl group, i.e. a hydrocarbyl containing 3 to 25 carbon atoms and at least an oxygen or sulfur in the principal chain. It is preferred that the hydrocarbyl group is saturated. It is further preferred that the hydrocarbyl group be a straight chain. The heteroatom hydrocarbyl group may contain more than one oxygen atom, sulfur atom or combination thereof in the principal chain, although oxygen is the preferred heteroatom. It is more preferred, however, that the principal chain contain only one oxygen or sulfur.

Furthermore, it is preferred that the heteroatom not be a to the acyl group or be on the omega position of the chain. It is most preferred that there may be only one heteroatom in the principal chain and that the heteroatom is oxygen.

Another preferred value of $E_1$ and $E_2$ are 1-substituted alkyl groups containing 3–25 carbon atoms and the substituents are hydroxy, halo, lower alkoxy, mercapto or alkylthio. In a more preferred embodiment, the substituent is hydroxy or halo, preferably bromo or chloro. In another preferred embodiment, the hydrocarbyl chain contains 13–15 carbon atoms. In the most preferred embodiment, the hydrocarbyl chain contains 13–15 carbon atoms and most preferably 13–14 carbon atoms and is 1-substituted hydroxy or halo.

Of course, various combinations and permutations are possible, as described below, from compounds in which $E_1$ and $E_2$ are independently heteroatom alkyl group, 1-substituted alkyl group or heteroatom 1-substituted alkyl group. These various combinations and permutations are contemplated to be within the scope of the present invention.

Preferred embodiments of the present invention are directed to compounds of Formulae IV, V or VII, wherein R is as defined hereinabove, $R_1$ and $R_2$ are hydrogen, alkyl fatty acid acyl group having 4–26 carbon atoms, or alkyl heteroatom fatty acid acyl group having 4–25 carbon atoms, and $E_1$ and $E_2$ are independently a heteroatom hydrocarbyl group containing 3 to 25 carbon atoms containing at least one oxygen or sulfur. The preferred definitions of $E_1$ and $E_2$ are as defined hereinabove.

In the embodiments described hereinabove in Formulae IV–VII, it is preferred that $R_1$ and $R_2$ wherever present, are independently hydrogen or alkyl fatty acid acyl group having 4–8 carbon atoms. Furthermore, it is preferred that the alkyl fatty acid acyl group have a carboxy substituent at the omega carbon. It is further preferred that $R_1$ and $R_2$ be straight chained.

In a further embodiment, the present invention contemplates a phospholipid drug of the formula:

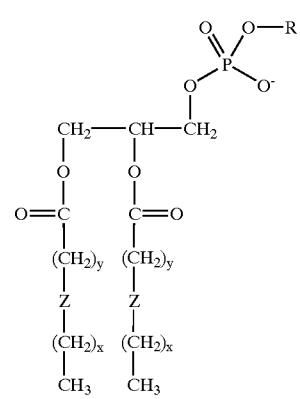

wherein R is as defined hereinabove;

Z is oxygen or sulfur;

each x is independently 0 to 13;

each y is independently 1 to 13; and x+y=11–15 and most preferably 11.

The present invention also contemplates a phospholipid drug of the formulae:

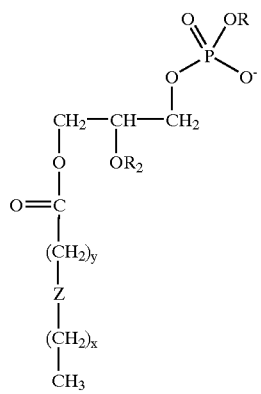

IX

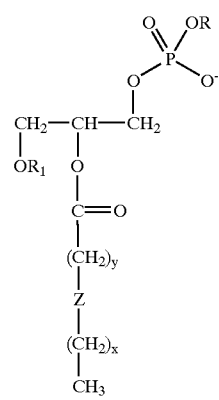

IXA wherein R is as defined hereinabove;

$R_2$ is hydrogen or alkyl fatty acid acyl group having 4–26 carbon atoms, and more preferably 4–8 or 14 carbon atoms, Z is oxygen or sulfur;

each x is independently 0–13;

each y is independently 1–13; and x+y=11–13, and most preferably 11.

In a further embodiment, the present invention relates to a phospholipid drug of the formula:

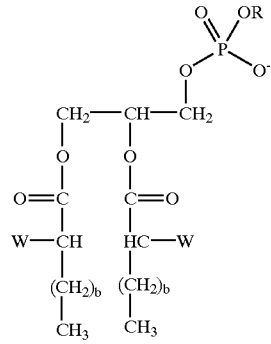

X wherein W is halo, hydroxy, alkoxy, mercapto or alkylthio;

and R is as defined hereinabove and b is 11–13 and most preferably 11.

Another preferred embodiment of the present invention relates to a phospholipid drug of the formulae:

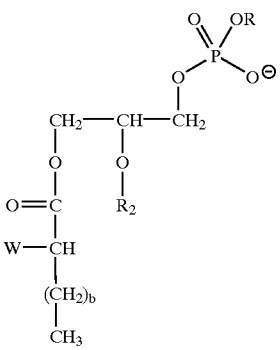

XI or

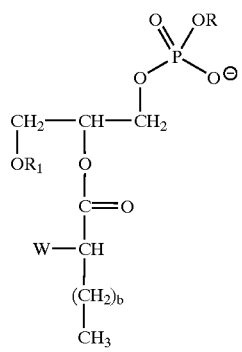

XII wherein R is as defined hereinabove;

$R_1$ and $R_2$ are independently hydrogen or alkyl fatty acid acyl group having 4–26 carbon atoms and more preferably 4–8 or 14 carbon atoms, b is 11–13, and most preferably 11 and W is selected from halo hydroxy, mercapto or alkylthio.

In a still further embodiment, the present invention relates to a phospholipid drug of the formula:

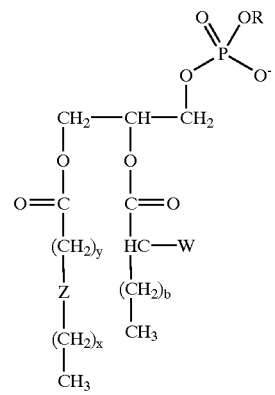

XIII wherein R, Z, W, x, y and b are as defined hereinabove.

Another embodiment of the present invention contemplates a phospholipid drug of the formula:

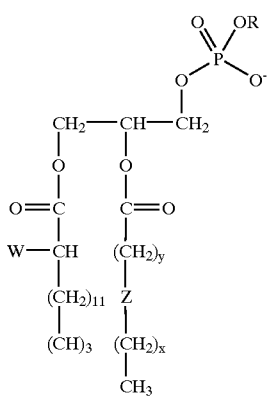

wherein R, Z, W, x and y are as defined hereinabove.

In a further embodiment, the present invention contemplates a phospholipid drug of the formula:

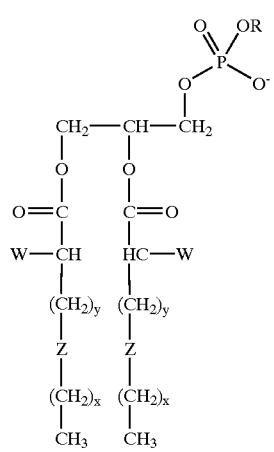

wherein R, Z, W, x, y are each as defined hereinabove.

In the various embodiments described herein, including the compounds of Formulae I–XV and A, it is preferred that R is

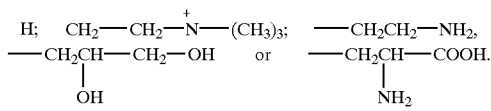

Preferably, R is

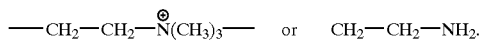

In all the embodiments contemplated in Formula VIII–XIV hereinabove, it is most preferred that Z is O or S, x=0, y=10 or 11 and W is hydroxy.

In the embodiments described hereinabove, all of the various combinations and permutations of the various variables, E, R, $R_1$, $R_2$, W, Z, x, y, b, etc., wherever possible, is contemplated by the inventors. Furthermore, the present invention encompasses embodiments (compounds, methods, compositions, etc.) which contain one or more elements of each of the Markush groupings in E, $R_1$, $R_2$, W, Z, x, y, b, etc. and the various permutations and combinations thereof.

In still another embodiment, the present invention contemplates the compound 1-myristoyl-2-(12-methoxydodecan-oyl)-sn-3-phosphalidylcholine (AC1) represented by the formula:

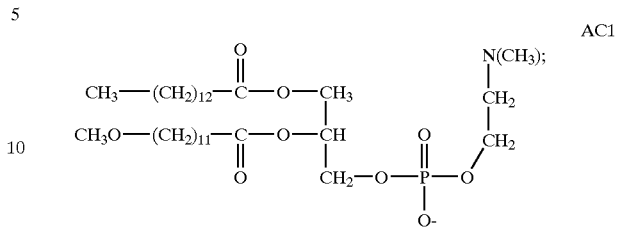

is clearly seen, AC1 contains the fatty acid 12MO bonded to the sn-2 position of the glycero backbone, while a myristoyl group is bonded at the sn-1 position. The present invention contemplates both the L- and D- stereoisomers.

In another embodiment, the present invention contemplates the compound 1,2-(di-12-methoxydodecanoyl)-sn-3-phosphatidylcholine (L-AC2) represented by the formula:

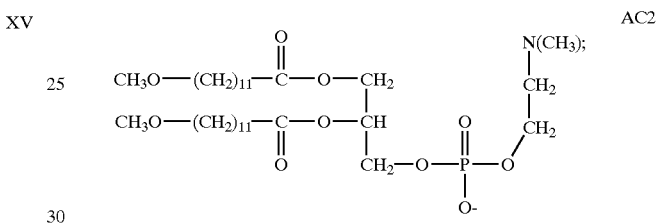

Compound AC2 contains the fatty acid 12MO bonded to both the sn-1 and sn-2 positions of the glycero backbone. Furthermore, the configuration at the sn-2 carbon of the glycero backbone is in the L configuration.

The present invention also contemplates the D-AC2 molecule, wherein the configuration at the sn-2 carbon of the glycerol backbone is in the D configuration.

In still another embodiment, the present invention contemplates the compound: 1-(12-methoxydodecanoyl)-sn-3-glycerophosphatidylcholine represented by the formula:

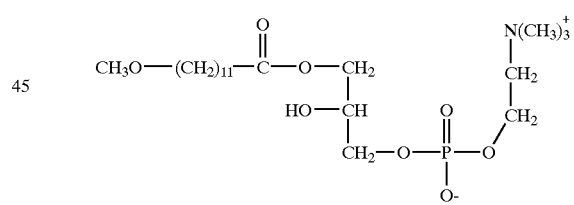

Hereinafter referred to as the "lysolipid analogs". The lysolipid analog contains the fatty acid 12MO bonded to the sn-1 position and hydrogen bonded at the sn-2 position of the glycerol backbone. Alternatively, the lysolipid analogs may contain the heteroatom fatty acid, (e.g., 12MO) bonded to the sn-2 position and the hydrogen bonded to the sn-1 position. Again, both the D- and L-stereoisomers contemplated by the present invention.

Compounds of Formulae VIII–XV in which the sum of x+y=11–12 and b is 11–12 are useful for the treatment of retroviral infections, including AIDS. These compounds interfere with HIV-1 replication in infected cells. Without wishing to be bound, it is believed that the compounds interfere with protein myristoylation.

The HIV-1 genome encodes for two myristoylated proteins: $p^{17gag}$ and $p^{27nef}$. In situ myristoylation of these proteins is critical for the establishment and maintenance of HIV infection. These myristoylation reaction can be represented as follows:

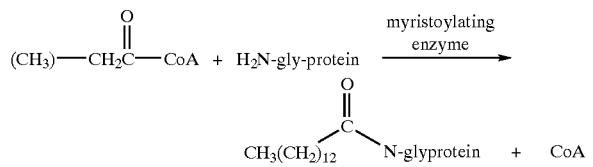

N-myristoyltransferase (NMT) is the enzyme that cotranslationally transfers the myristoyl group to endogenous cellular and viral proteins. It is believed that the compounds of the formulae VII–XV in which the sum of x+y=11–12 and b is 11–12 exhibit inhibitory activity against viruses that produce myristoylated proteins.

Interference with protein myristoylation has been a drug target site for inhibiting HIV replication. It has been reported that heteroatom analogs of myristic acid containing oxygen or sulfur substituted for alkyl methylene groups exhibit activity against HIV replication in infected cells. European Patent Application 415,902 alleges that oxy and thio substituted fatty acid analog substrates of myristoylating enzymes in which a methylene group at carbon position 4 to 13 is replaced by an oxygen or sulfur can be used to treat retroviral infections. It has also been reported that metabolic activation of 2-substituted derivatives of myristic acid inhibits myristoyl CoA: Protein N-myristoyltransferase. See Paige, et al., Biochemistry 1990, 29, 10566–10573.

However, the present inventors have discovered that the efficacy of these compounds have been significantly enhanced by acylating these molecules to the glycerol backbone of a phospholipid in accordance with the present invention, thus generating new phospholipid drugs. More particularly, the fatty acid analogs of myristic acid are acylated to one or both of the hydroxy groups of the glycerophospholipid, i.e. the non-polar end. The acylation at the non-polar end of the phospholipid significantly influences the ability to inhibit HIV replication in macrophages and T cells and also alters the toxicity of the fatty acid analogs. Additionally, these acylated phospholipids may be sensitive to phospholipases A1 and A2, thereby providing a specific cleavage mechanism for the acyl group(s) containing the biologically active fatty acids, once the product is transported into the cell.

The present compounds can be formulated with suitable pharmaceutically acceptable carriers into unit dosage form and can be administered orally, transdermally parenterally or rectally. The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers and the like. Such compositions and preparations should contain at least 1% of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains a pharmaceutically effective amount which can be determined by the physician. For example, the oral dosage unit form may contain between about 0.5 and 1000 mg of active compound.

The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such a peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

The active compound may also be administered parenterally or intraperitoneally. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene, glycol, and liquid polyethylene glycol and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in unit dosage form for ease of administration and uniformity of dosage unit. Dosage form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. The physician can determine the amount of drug to be utilized. A unit dosage form can, for example, contain the principal active compound in amounts ranging from about 0.5 to about 1000 mg. In the case of compositions containing supplementary active ingredients, the dosages are determined by reference to the usual dose and manner of administration of the said ingredients.

The general descriptions above with respect to the present invention are illustrated with the AC1, AC2, and the lyso analog, described hereinbelow. The following application of the generalizations hereinabove are provided solely for illustrative purposes. The invention is not to be limited in any way by the exemplification hereinbelow. The AC1 and AC2 and the lyso compound in the most preferred embodiments of the present invention can be prepared by art recognized synthetic procedures. Exemplary schemes are as outlined below.

Heteroatom-fatty Acids

The general synthetic scheme for synthesizing heteroatom-fatty-acids is outlined in EPA 0,415,902. For example, their preparation can be carried out by methods analogous to the preparation of mixed ethers by the Williams synthesis. Thus, an appropriate ω-bromo carboxylic acid can be reacted with an alcoholate or an alkyl thiol to produce, respectively, the oxy-substituted fatty acid ether or thio-substituted fatty acid ether.

For example, they may be prepared by procedures analogous to the synthesis of heteroatom substituted analogs of stearic acid, as described by Pascal and Ziering, *J. Lipid Res.* 27, 221–224 (1986). Using these methods, the sulfur containing fatty acids are prepared by the condensation of appropriate alkyl thiols and ω-bromo carboxylic acids in the presence of alcoholic base, as illustrated by the process:

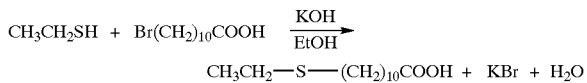

Similarly, the oxygen-containing fatty acids can be prepared by the reaction of the ω-bromo acids with alcoholic base. This can be illustrated as follows:

Other oxy- and thio-substituted fatty acid compounds can be prepared by similar such methods by selecting appropriate alkyl and fatty acid chain lengths in the reactant compounds to produce the desired products. Both of the foregoing type reactions are carried out in organic solvent medium at refluxing temperatures until the desired reaction is essentially complete.

Synthetic scheme:

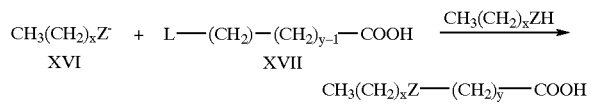

wherein x, y and Z are as defined hereinabove and L is a leaving group, such as halo, OTS, OMS and the like. A base having Formula XVI is reacted with a carboxylic acid of Formula XVII under Williamson-like conditions in $CH_3(CH_2)_xZH$. The reaction is run at effective temperatures, which may range from room temperature up to reflux temperatures, although it is preferred that the reaction be carried out under reflux temperatures. The following example illustrates the formation of the heteroatom fatty acids.

The general synthetic scheme for obtaining 12 MO is outlined below. A flame dried 300-ml round bottom flask was cooled before 8.4 g (0.030 mol) of 12-bromododecanoic acid was mixed with 6.5 g (0.120 mol) sodium methoxide in 200 ml of absolute methanol. The yellow solution was refluxed at 85° C. for 16–20 hours under a nitrogen atmosphere. After refluxing, the mixture was allowed to cool and the solvent was removed by rotoevaporation. After removing most of the solvent, approximately 2–4 milliliters of residue remained and was extracted by the addition of ethyl acetate 100 ml, ether 50 ml and $H_2O$ 50 ml. Prior to acidification, the organic layer was clear and the top aqueous layer was yellow. This organic/aqueous mixture was acidified to pH 3 with 1 N HCl causing the organic layer to yellow and the aqueous layer to become clear. The aqueous and organic layers were separated and the aqueous layer was extracted twice with 30–50 ml of ethyl acetate. The organic extracts were pooled and washed once with 50 ml of $H_2O$. The organic layer was dried using anhydrous $Na_2SO_4$ and filtered. After removing the solvent by rotoevaporation, the residue was heated (50° C.) under vacuum for 5 hours to remove trace organic solvents. TLC analysis using ethyl acetate:hexanes:formic acid 88:9:3, gave rf=0.25. Typical yields range from about 80–95%.

Hetero-atom-fatty-acid Anhydrides

The corresponding anhydride of the heteroatom fatty acid is formed by coupling the heteroatom fatty acid with a dehydrating agent, such as dicyclohexylcarbodiimide, as illustrated by the exemplary procedure hereinbelow.

The anhydride was prepared in a flame dried 50-ml round bottom flask containing 5.4 g (0.024 mol) of 12-methoxydodecanoic acid completely dissolved in 20 ml of dry THF under a nitrogen atmosphere. After adding DCC 2.40 g (0.012 1 mol) dropwise over 5 minutes, the reaction was complete in under 25 minutes as monitored by the disappearance of the DCC imine vibration band (centered at 2100 $cm^{-1}$). Preliminary studies showed if solid DCC was added to the reaction mixture then several side products were found by TLC. Consequently DCC was melted, weighed into a flame dried beaker, and diluted with 5 ml of dry THF. Dicyclohexylurea (DCU) precipitates within the first few minutes of DCC addition. DCU was removed by paper filtration (Whatman #1). The solvent was removed by rotoevaporation and placed under a heated vacuum (50° C.) for 12 hours. FTIR and TLC analysis (ethyl acetate:hexanes:formic acid 88:9:3) revealed no DCU or DCC in the final product. Typical yields were 90–95%.

Substituted Myristic Acid Analogs

The synthesis of the substituted myristic acid is also prepared by art recognized techniques. Although the reaction substrate described hereinbelow is myristic acid, the following examples are exemplary and are applicable to fatty acids in general.

The fatty acid can be halogenated as follows:

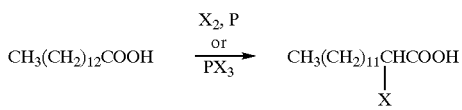

wherein X is halo, e.g., bromo or chloro. The fatty acid is halogenated with phosphorus in the presence of halogen, or with $PX_3$ under Hell-Volhard-Zelinsky reaction conditions to form the α-halogenated product. Alternatively, the acid may be formed in two steps using a variation of the malonic ester synthesis:

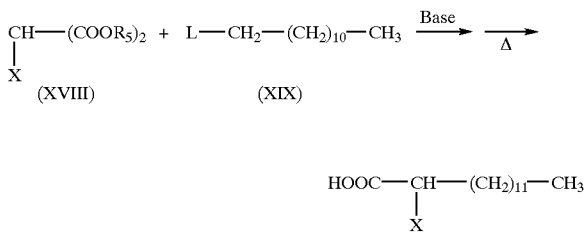

In the above scheme, X is halo, $R_5$ is lower alkyl, such as methyl, ethyl and the like, and L is a better leaving group than X, such as OTS, OMS and the like. For example, if X if F, then L may be OTS, OMS, Br, I and the like.

As described hereinabove, halo malonic acid ester (XVIII) is reacted with a strong base to remove the acidic hydrogen on the α-carbon. The resulting anion is then reacted with an alkyl halide (XIX) and forms the coupled diester. The reaction is run in an inert solvent, such as dimethyl formamide, and preferably under anhydrous conditions. The resulting product is then heated at temperatures effective for decarboxylation to form the final product.

The reaction is further exemplified by the following example.

The general synthetic scheme for synthesizing substituted myristic acid analogs is similar to the synthesis of 2-fluoromyristic acid which can be synthesized as follows: To a suspension of 0.32 g (11.2 mmol) of an 80% oil dispersion of NaH in 8 mL of dry DMF was added dropwise 2 g (11.2 mmol) of diethyl fluoromalonate under argon. The suspension was then stirred for 4.5 h after which time, 2.79 g (11.2 mmol) of 1-bromododecane was added and the solution was heated at 90° C. for 18 h. The yellow suspension was then poured into 10 mL of water and extracted with ether (2×15 mL). The combined ether layers were washed, dried and evaporated. A yellow oil resulted, which was used for the next reaction without further purification. A mixture of 3.8 g of the crude diethyldodecylfluoromalonate (8), 30 mL of 6 N HCl, and 50 mL of dioxane was refluxed for 72 h. After cooling, the yellow solution was dissolved in 100 mL of petroleum ether (bp 40–60° C.). The organic layer was separated and washed with water (3×50 mL) and 10% KOH (2×250 mL). The combined aqueous layers were acidified to pH 1.0 with concentrated HCl and extracted with ether (3×100 mL). The ether layer was dried, filtered and evaporated to dryness to yield a green solid. The solid was decolorized with activated carbon and recrystallized from petroleum ether (bp 40–60° C.) to give 1.501 g (54% overall yield) of 2-fluoromyristic acid (2) as white needles.

2-bromomyristic acid was purchased from Aldrich and 2-hydroxymyristic acid was purchased from Fluka.

A beta hydroxy acid can be formed by reacting a β-halo ester with an aldehyde in the presence of zinc under Reformatsky reaction conditions in an inert solvent, such as toluene or DMF.

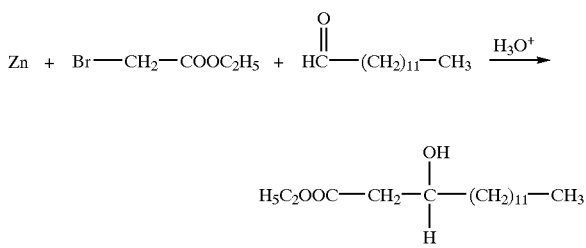

The resulting product is then hydrolyzed to form the corresponding acid.

The β-hydroxy compound can then be converted to the corresponding halide by art recognized techniques, such as reaction with thionyl bromide or chloride, phosphorous trihalide, ($SO_2Cl_2$, $SO_2Br_2$, $PCl_3$, $PI_3$) and the like.

The corresponding anhydrides of the substituted fatty acid analog can be prepared by coupling the substituted fatty acid analog prepared hereinabove with a dehydrating agent, such as decyclohexylcarbodiimide, as illustrated by the exemplary procedures hereinabove.

Phospholipids

The phospholipids are prepared by art recognized techniques by reacting an acylating derivative of the fatty acid, such as the fatty acid anhydride, with the glycerol phosphate of the formula:

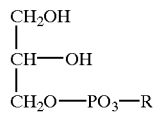

wherein R is as defined hereinabove, under esterification conditions. This reaction is illustrated hereinbelow. Although the reaction is illustrated using the heteroatom fatty acid to form the heteroatom fatty acid phospholipid, the reactions described hereinbelow are applicable using the substituted fatty acid analogs to form the phospholipid containing the substituted fatty acid analogs.

The chemical reaction for the solid phase adsorption synthesis of L-AC2 is given in Rxn. 1. The synthetic route for obtaining the anhydride used in Rxn. 1 is given above.

Rxn.1
Solid
Phase
Synthesis

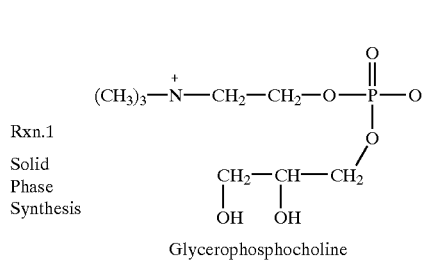 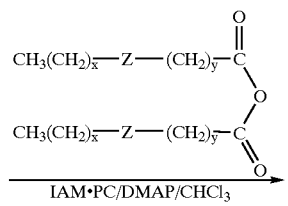

Glycerophosphocholine

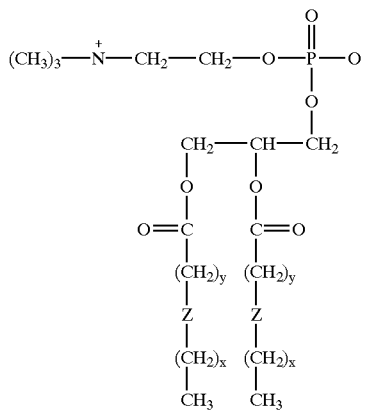

Diacylated phosphatidlycholine analogs x = 0–11
y = 0–11
x+y = 11
Z = oxygen or sulfur Phospholipids are not difficult to synthesize, but the present novel-synthetic-method overcomes several experimental inconveniences associated with phospholipid synthesis. During the synthesis of diacylated phospholipids, experimental inconvenience involves the insolubility of glycerophosphocholine (OPC) in common organic solvents. Although GPC is soluble in dimethylsulfoxide (DMSO), the use of DMSO requires vacuum distillation and in addition, DMSO makes the purification of phospholipids more difficult. The inventors have developed a novel method for synthesizing molecules when all reactants are not soluble in the same organic solvent. The method involves using a chromatographic surface to promote the interaction between one insoluble surfactant and one soluble reactant. In other words, the insoluble-reactant is initially adsorbed to the chromatographic surface, and the soluble-reactant partitions into the chromatographic interface during the reaction. Partitioning of the soluble-reactant between the chromatographic surface and the reaction solvent permits the insoluble molecule, adsorbed at the interfacial region, to react with the soluble reactant. Although other chromatographic surfaces may be useful, IAM.PC chromatographic surfaces were utilized.

The synthesis of AC2 demonstrates the solid-phase-synthetic procedure shown in Rxn. 1. GPC (250 mg, 1 mMol) solubilized in MeOH (0.5 ml), was adsorbed to IAM.PC (200 mg) by dropwise addition of the methanolic-GPC solution; the MeOH was allowed to evaporate after the IAM.PC surface was completely loaded with GPC. The IAM.PC/GPC solid material was dried overnight in a vacuum oven at 45° C. After drying, the IAM.PC/GPC powder was then suspended in dry $CHCl_3$ containing 1 equivalent of the appropriate anhydride per GPC alcohol, and 1 equivalent of catalyst (i.e., dimethylaminopyridine denoted as DMAP). Both the anhydride and DMAP were dried by vacuum at 45° C. After 6 hours, TLC confirmed the reaction was complete, and the phospholipid product was purified by acetone precipitation and/or silica chromatography. Normally the synthesis would have required 4–5 days per phospholipid and 2 equivalents of anhydride, but this method requires approximately 1–2 days and 1 equivalent of anhydride.

General structures of mono- and diacylated phospholipids whereby all alkyl chains are biologically active fatty acids are shown below. For both the mono- and diacylated phospholipids: x=0–11; y=0–11, and x+y=11 for any given analog. "Z" denotes the hetero-atom and will be either oxygen or sulfur. The chemical reactions for the synthesis of each compound is also given below.

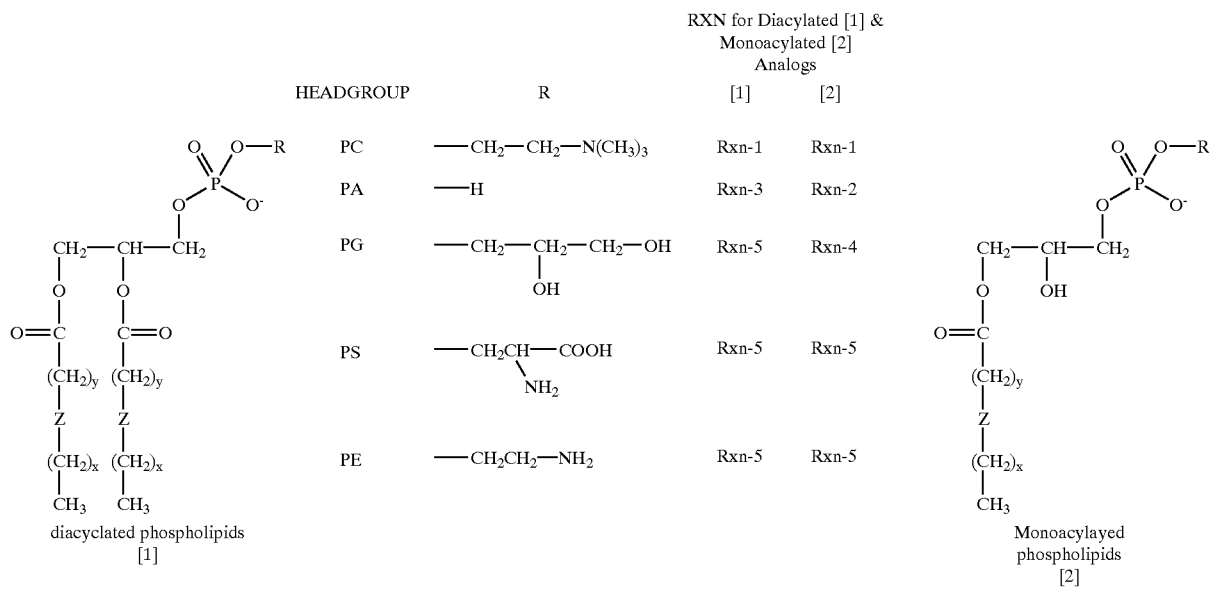

diacyclated phospholipids [1]

Monoacylayed phospholipids [2]

Chemical reactions 2–6 for the above synthetic routes are illustrated below. Briefly, diacylated analogs are prepared by a solid-phase adsorption method (see Rxn. 1 of Pages 54–55 of the application), monoacylated analogs can be prepared from phospholipase A2 treatment of the diacylated compounds, and diacylglycerol analog can be prepared from a separate reaction scheme (i.e., reaction 6). Reaction 6 involves first protecting glycidol epoxide using diphenyl-yl-(t)-butylchloride to form glycidol-tert-butyldiphenylsilyl ether. The epoxide ring is then opened with base, the protected glycerol is diacylated with 12-methoxydodenoyl anhydride. The final step in reaction 6 involves protecting the diacylglycerol sn-3 alcohol using n-butylamonium fluoride.

Diacylated phosphatidylcholine analogs containing oxygen or sulfur substituted for methylenes can be hydrolyzed with phospholipase A2 to obtain the corresponding lysolecithin analogs.

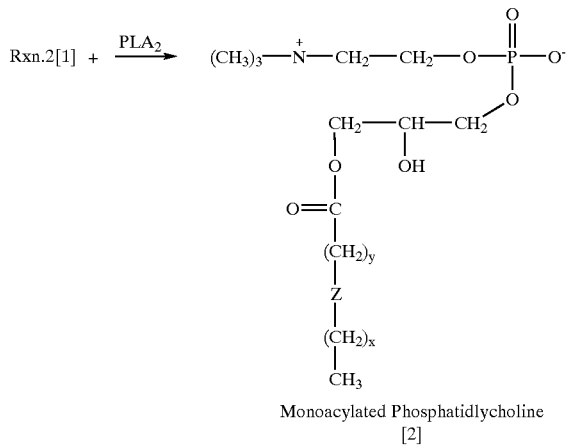

Monoacylated Phosphatidlycholine [2]

Diacylated phosphatidic acid analogs can be synthesized by reacting L-glycerol-3-phosphate with the appropriate anhydride oh the surface of an immobilized artificial membrane particle. This reaction was described in detail in the discussion of reaction 1 using glycerophosphatidylcholine as starting material (see Reaction 3).

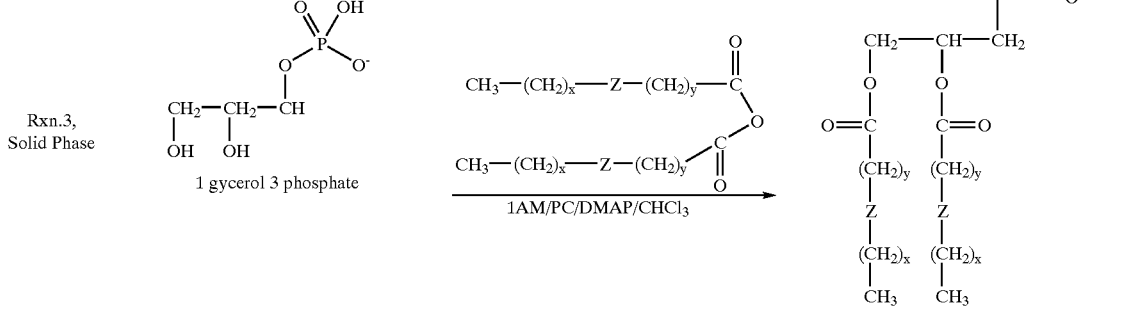

Monoacylated analogs of phosphatidic acid can be obtained by phospholipase A2 cleavage of the diacylated analogs denoted by [3] in reaction 3. This reaction is described hereinbelow:

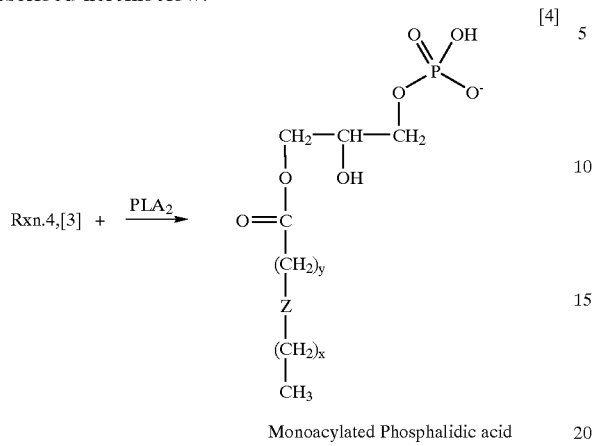

Monoacylated Phosphalidic acid

Diacylated analogs containing either a glycerol serine (PS), or ethanolamine (PE) headgroup can be synthesized by transphosphatidylation using phospholipase D treatment of diacylated phosphatidylcholine analogs denoted (1) in rxn. 5. The lysolipid analogs with these headgroups can then be obtained by further reaction with phoslipase A2 cleavage.

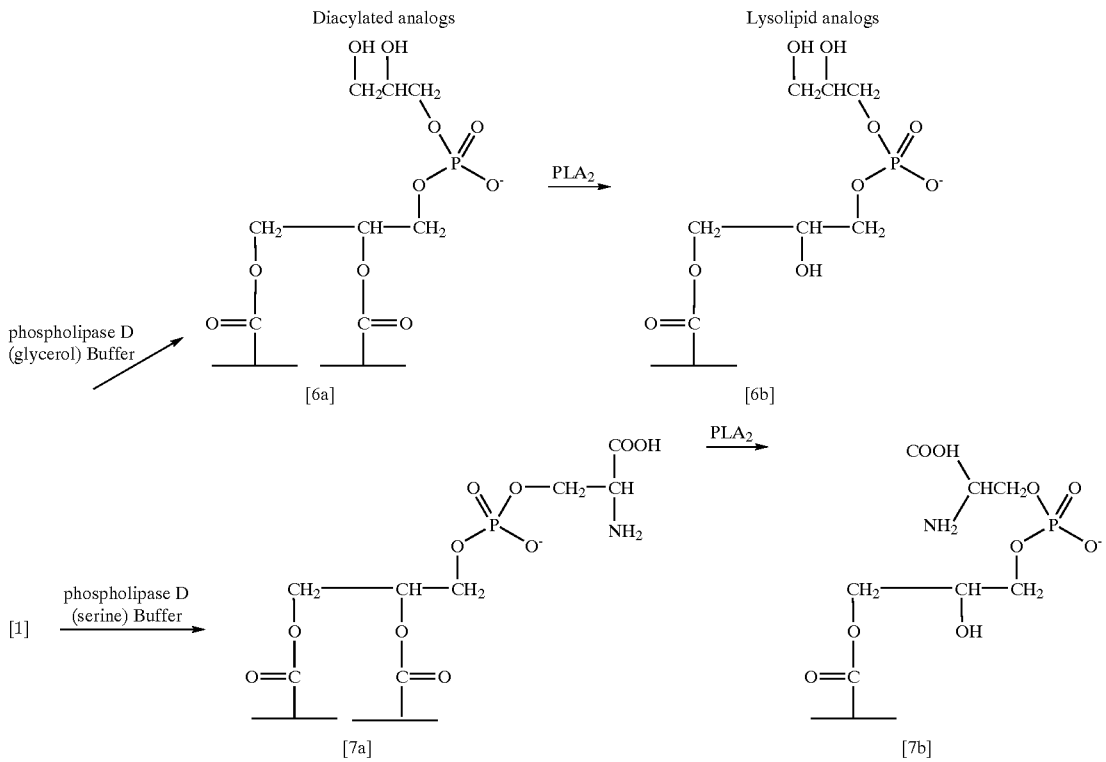

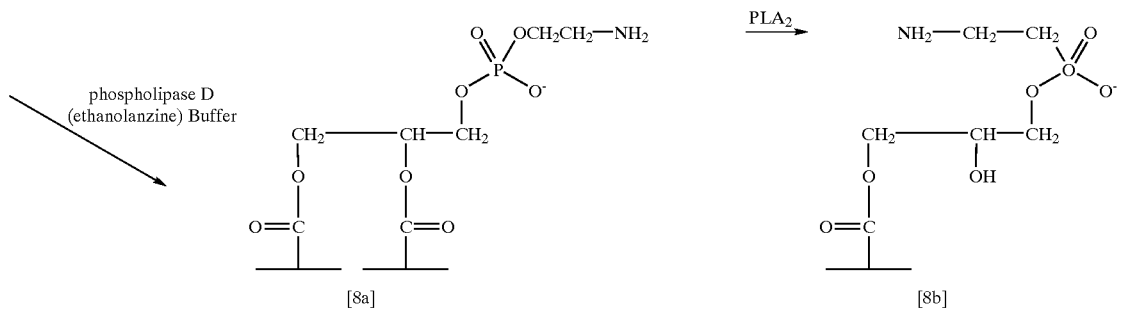

[8a] → PLA₂ → [8b]

(~~~) denotes the rest of the fatty acid chain.

Diacylglycerol analogs containing two identical stero-atom-fatty acids can be synthesized from (t)butyldiphenylsilyl-O-glycidol. This reaction is performed by solid base adsorption method employed in reaction 1 using glycerophosphatidylcholine as substrate.

Rxn.6,

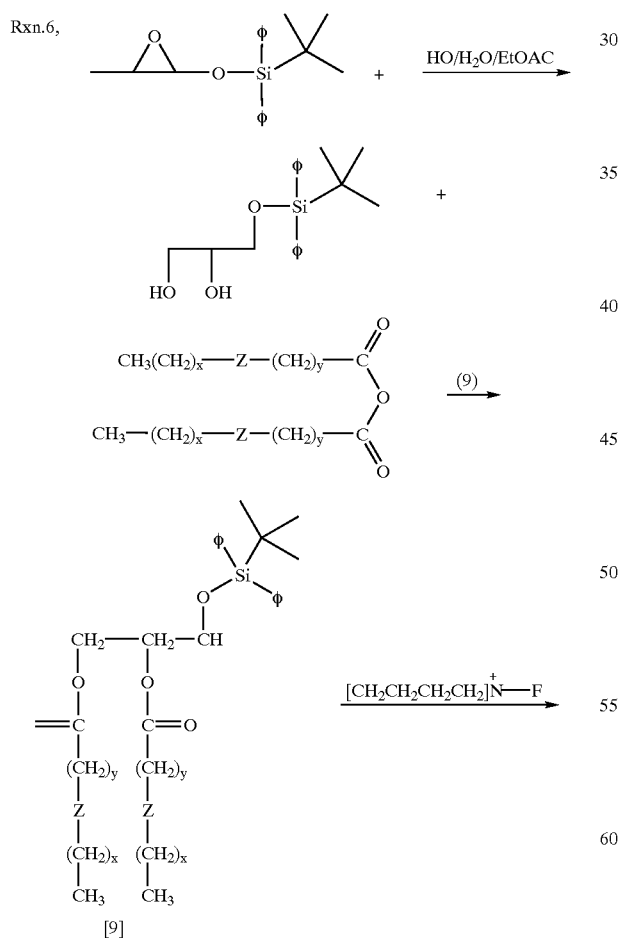

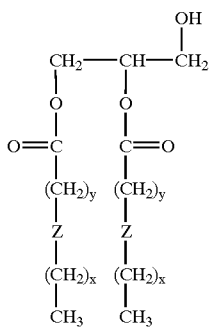

Diacylglycerol analogs

EXAMPLES

GENERAL SYNTHESIS

Lecithins are 'diacylated' phospholipids and scheme 1 and scheme 2 show the general synthetic pathway used to obtain anti-HIV lecithins containing the phosphatidyletha-nolamine headgroup. Scheme 1 shows the general synthetic scheme used to prepare a lipid containing two 12-methoxydodecanoyl groups and a phosphatidylethanola-mine headgroup; this lipid is denoted as di-12MOGPE. Briefly, L-α-GPE was reacted with Fmoc-NHS to form GPE-Fmoc in a mixed solvent system; this reaction protected the 1° amine of GPE. GPE-Fmoc was then acylated with 12-MO-anhydride in dry chloroform to form the diacylated product (di-12MOGPE-Fmoc). Di-12MOGPE was then obtained by removing Fmoc with piperidine. Scheme 2 shows the general synthetic scheme used to prepare the anti-HIV lecithin containing one 12-methoxydodecanoyl group and one saturated fatty acid. Briefly, monomyris-toylphophatidylethanolamine (MMPE) was reacted with Fmoc-NHS to form MMPE-Fmoc; this reaction protected the 1° amine of MMPE. MMPE-Fmoc was then acylated with 12-MO-anhydride in dry tetrahydrofuran to form the diacylated product. 1-M-2-12MOGPE-Fmoc. 1-M-2-12MOGPE was then obtained by removing the Fmoc group with piperidine.

Scheme 3 shows the general synthetic scheme used to prepare the anti-HIV lipid containing the phosphatidylcho-line headgroup. Briefly, diacylated lecithins were prepared from both the L and D form of glycerophospocholine (L-α-GPC and D-α-GPC) by acylation using 12-MO anhydride. The single chain analog of the L configuration was then prepared from phospholipase A2 cleavage of the diacylated product. For all reactions described above, acylation using the 12-MO-anhydride used 2 equivalents of anhydride per alcohol and 1.5 equivalents of catalysts (DMAP) per alcohol.

CHEMICAL AND SOLVENTS

Chemicals and solvents were used as received unless stated otherwise. 1-myristoyl-sn-glycero-3-phosphoethanolamine (MMPE) was purchased from Avanti Polar Lipis Inc. (Birmingham, Ala.). L-α-glycerophosphoethanolamine (GPE) and N-(9-Fluorenylmethoxycarbonyloxy) succinimide (Fmoc-NHS) were purchased from Sigma Chemical Company. D-α-glycerophosphocholine was purchased from Biochemisches Labor, Berne CH, Switzerland. Dimethylaminopyridine (DMAP) purchased from Aldrich was crystallized 2 times from ethyl ether. Dicylohexylcarbodiimide (DCC) was purchased from Aldrich. Sodiumbicarbonate ($NaHCO_3$) was obtained from Fisher Scientific Chemical Company. Analytical grade chloroform ($CHCl_3$), methanol (MeOH), and tetrahydrofuran (THF) were obtained from Fischer Scientific. $H_2O$ was double distilled from glass containers. Dry THF and Dry $CHCl_3$ were prepared by distillation over calcium hydride. Calcium hydride was purchased from Alpha Products, Danver, Mass. 12-methoxydodecanoic acid 12MO was prepared as described hereinabove. 12-methoxydodecanoyl anhydride (MO-anhydride) was prepared using DCC an purified by crystallization using ethylacetate. Piperidine was obtained from Fisher Scientific Chemical Company. Ninhydrin and Phospray were purchased from Supelco Inc. Bellefonte, Pa.

Thin layer chromatography (TLC) was used to monitor all reactions. Silica gel TLC plates were 60 F-254, 0.25 mm thickness (E. Merck, Darmstadt, FGR). Two TLC solvent systems were used: solvent system A contained $CHCl_3$/$CH_3OH$/$H_2O$ 65:25:5 V:V:V; solvent B contained $CHCl_3$/$CH_3OH$/$H_2O$/THF 64:34:7:30 V:V:V:V. TLC plates were sprayed with either Ninhydrin (Supelco Inc. Bellefonte, Pa.) to visualize amines or Phospray (Supelco Inc. Bellefont, Pa.) to visualize phosphate. The extent of reaction was routinely quantified using a scanning densitometer (Shimadzu CS 9000) operating in the reflectance mode. TLC plates were sprayed with Phospray prior to scanning at 600 nm. Phospholipid standards were always included on the same TLC plate used for lipid quantification. Silica gel for flash chromatography was grade 60, 230–400 mesh and obtained from Aldrich Chemical Company. The solvent systems described hereinabove were also used to purify the heteroatom containing phospholipid drugs by flash chromatography.

L-α-Glycerophosphoethanolamine-fluorenylmethyloxycarbonyl (GPE-Fmoc).

GPE (93 μmole, 20 mg), Fmoc-NHS (130 μmole, 45 mg) and $NaHCO_3$ (288 μmoles, 24 mg) were transferred into a round bottom flask, and 10 mls of $CHCl_3$/$CH_3OH$/$H_2O$ (32:17:2 V:V:V) was immediately added to the flask. The reaction mixture was stirred at room temperature. GPE and Fmoc are soluble in this solvent system but $NaHCO_3$ is only slightly soluble. Based on TLC in solvent system A, quantitative yields are obtained in approximately three and half hours. The reaction mixture was filtered to remove $NaHCO_3$ (solid) and the filtrate was rotoevaporated to dryness. After rotoevaporation the residue was redissolved in $CHCl_3$ (~1 ml) and loaded on to dry silica gel loosely packed in a cylindrical glass frit filtration funnel (~5 g of silica per 1 g of reaction mixture). The unreacted Fmoc-NHS washed off with $CHCl_3$ (10 mls), and NHS washed off with $CH_3OH$ (10 mls). The product was then washed with $CHCl_3$/$CH_3OH$ 1:1 V:V (10 mls) to obtain pure GPE-Fmoc. GPE-Fmoc ($R_f$ of 0.24) shows one spot on TLC plates developed in solvent system A. GPE-Fmoc is UV positive, Phospray positive, and Ninhydrin negative.

di-(12-Methoxydodecanoyl)-sn-glycero-3-phosphoethanolamine-fluorenylmethyloxycarbonyl (di-12MOGPE-Fmoc)

GPE-Fmoc, MO-anhydride and DMAP were dried in a vacuum desiccator at 40° C. for at least four hours before use. GPE-Fmoc (93 μmol, 40 mg), MO-anhydride (410 μmol, 180 mg) and DMAP (200 μmol, 24 mg) were added to a flame dried round bottom flask and freshly distilled $CHCl_3$ (10 mls) was added. The reaction mixture was under a $N_2$ atmosphere and stirred at 40° C. After 20 hours, TLC in solvent system A confirmed that the reaction was virtually complete; the major product di-12MOGPE-Fmoc had an Rf of 0.46. Rotoevaporation of the reaction solvent left a dry residue which was redissolved in minimal $CHCl_3$ (~1 ml). The $CHCl_3$ solubilized residue was loaded on to silica gel packed inside a cylindrical glass-frit filtration funnel (~5 g silica/g of residue). The unreacted MO-anhydride washed off the silica with $CHCl_3$ (~200 ml); TLC in solvent system A was used to monitor MO-anhydride in the filtrate. We note that it is important to remove MO-anhydride from the crude product-mixture to avoid decreased retention times and coelution of the products and reactants during column chromatography. After the anhydride was removed, $CHCl_3$/$CH_3OH$/$H_2O$ (60:35:5 V:V:V) (~50 mls) was used to wash off the reaction products. Rotoevaporation of the filtrate left a crude product-mixture. The product mixture was redissolved in a minimum volume of mobile phase $CHCl_3$/$CH_3OH$/$H_2O$ (65:25:4 V:V:V) and purified using flash chromatography (3 cm×21 cm column, ~2 mg of reaction mixture per 1 g of silica gel). Fractions eluting from the column (10 ml/fraction) were analyzed by TLC in solvent system A. Fractions containing di-12MOGPE-Fmoc were pooled and the solvent removed by rotoevaporation. The pure product (di-12MOGPE-Fmoc) showed one UV positive TLC spot that was also Ninhydrin negative and Phospray positive. The yield was ~70%.

1,2 di-(12-Methoxydodecanoyl)-sn-glycero-3-phosphoethanolamine (di-12MOGPE)

di-12 MOGPE-Fmoc was dissolved in dry $CHCl_3$ (20 mg/ml) at room temperature and piperidine was added [1:80 di-12MOGPE-Fmoc:piperidine]. Fmoc is completely removed in 2 hours but if twice the amount of piperidine is used, then 100% conversion occurs within 45 minutes. On TLC in solvent system A, di-12-MOGPE has an Rf of 0.3 and is both Ninhydrin and Phospray positive but UV negative which indicates that the Fmoc group has been removed. The reaction solvent was removed by rotoevaporation and the crude residue dissolved in 1 ml of solvent system A and purified by flash chromatography (3 cm×21 cm) using the same solvent system. Fractions were collected (10 ml/fractions) and analyzed by TLC in solvent system A. Fractions containing the product were pooled and the solvent removed by rotoevaporation to obtain pure di-12MOGPE. The final lecithin product (di-12MOGPE) exhibited one spot on TLC in solvent system A and was Ninhydrin positive, Phospray positive, and UV negative.

FAB-MS: $MH^+$ 640.3. IR ($CaF_2$, neat) $v_{as}$ $CH_2$ 2917.4; ν $CH_2$ 2850.4; ν C=O 1738.4; $\delta_{as}$ $CH_2$ 1454.0; $v_{as}$ $PO_2$ 1230.6; νC—O—C 1077.8; $v_s$ $PO_2$ 1027.9. $^1H$ NMR (500 MHz, $CDCl_3$) results: δ 5.18 ppm (br s, 1H, CH), 4.35 ppm (m, 1H, $CH_2OP$), 4.11 ppm (m, 1H, $CH_2OP$), 4.05 ppm (br s, 2H, $CH_2OP$), 3.90 ppm (br s, 2H, $CH_2OCO$), 3.33 ppm (t, 4H, $OCH_3$), 3.30 ppm (s, 6H, $OCH_3$), 3.12 ppm (br s, 2H, $NCH_2$), 2.28 ppm (m, 4H $CH_2COO$), 1.55 ppm (m, 8H $\underline{CH_2}CH_2COO$, $\underline{CH_2}CH_2OCH_3$), 1.25 ppm (br s, 28H, $(CH_2)_7$).

1,3 di-(12-Methoxydodecanoyl)-sn-glycero-2-phosphoethanolamine-fluorenylmethyl-oxycarbonyl (1,3 di-12MOGPE-Fmoc)

Headgroup migration occurred during the preparation of di-12MOGPE-Fmoc and the migration product was 1,3 di-12MOGPE-Fmoc. This migration product was purified by flash chromatography as described above for di-12MOGPE-Fmoc. 1,3 di-12MOGPE-Fmoc exhibited one spot on TLC in solvent system A with an Rf=0.4.

$^1$H NMR (500 MHz, CDCl$_3$/CD$_3$OD) results: δ 7.68 ppm (d, 2H, aromatic), 7.55 ppm (d, 2H, aromatic), 7.30 ppm (t, 2H, aromatic), 7.22 ppm (t, 2H, aromatic), 4.33 ppm (br s, 1H, CHOP), 4.28 ppm (d, 2H, CH$_2$CHCC), 4.10 ppm (t, 1H, CHCC), 4.15 ppm (m, 1H CH$_2$OP), 3.90 ppm (m, 1H, CH$_2$OP), 3.82 ppm (br s, 2H, CH$_2$OP), 3.80 ppm (br s, 2H, CH$_2$OCO), 3.42 ppm (br s, 2H, NCH$_2$), 3.30 ppm (t, 4H, OCH$_2$), 3.23 ppm (s, 6H OCH$_3$), 2.15 ppm (t, 4H, CH$_2$COO), 1.50 ppm (m, 8H CH$_2$CH$_2$COO, CH$_2$CH$_2$OCH$_3$), 1.20 ppm (br s, 28H, (CH$_2$)$_7$).

1-Myristoyl-sn-glycero-3-phosphoethanolamine-fluorenylmethyl-oxycarbonyl (MMPE-Fmoc)

MMPE (9.88 mmoles, 4.2 g) and insoluble NaHCO$_3$ (29 mmoles, 2.4 g) were mixed in 50 mls of CHCl$_3$/CH$_3$OH/H$_2$O 32:17:4 V:V:V for 2 minutes at room temperature prior to the addition of Fmoc-NHS (13.3 mmoles, 4.5 g). After 2–3 hours the reaction was virtually complete based on TLC in solvent system A. Without NaHCO$_3$ the yield was always 50–60% regardless of reaction conditions. The reaction was filtered through a fine glass-frit funnel to remove NaHCO$_3$ (solid) and the filtrate was rotoevaporated to obtain a residue. The dry residue (~9 g) was redissolved in minimum CHCl$_3$ (2–3 ml) and loaded on to dry silica loosely packed in a glass filtration funnel (~5 g of the silica gel per g of reaction mixture). Based on TLC in solvent system A, unreacted Fmoc-NHS washed off the silica with CHCl$_3$ (~100 mls/g-product). After removing Fmoc-NHS from the product-mixture, both the phospholipid-product and NHS byproduct coeluted using ~300 mls of CHCl$_3$/CH$_3$OH/H$_2$O (32:17:4 V:V:V). The mixed solvent containing the product was removed by rotoevaporation and the residue extracted with CHCl$_3$/CH$_3$OH/H$_2$O 8:4:3 V:V:V to remove NHS and other impurities. The product remained in the organic phase during the extraction. During extraction approximately 20% of the product was lost into the aqueous phase but was recovered by reextraction of the aqueous phase with fresh organic solvent. MMPE-Fmoc was an amorphous white solid after lyophilization from benzene. The pure MPE-Fmoc shows one spot (Rf of 0.36) during TLC in solvent system A. MMPE-Fmoc is UV positive, Phospray positive and Ninhydring negative. Product yields ar 70–90% based on 2 reactions.

IR (CaF$_2$, neat) results: OH 3336.0 (broad); $v_{as}$ CH$_3$ 3064.7; $v_s$ CH$_3$ 2953.1, δ$_{as}$ CH$_2$ 2923.9; $v_s$ CH$_2$ 2852.9; vC=O 1721.7; v1533.8; δ$_{as}$ CH$_2$ 1450.3; $v_{as}$ PO$_2$ 1236.2; vC—O—C 1108.5; $v_s$ PO$_2$ 1069.0. $^1$H NMR (500 MHz, CDCl$_3$/CD$_3$OD) results: δ 7.55 ppm (d, 2H, aromatic), 7.18 ppm (t, 2H, aromatic), 7.10 ppm (t, 2H, aromatic), 4.15 ppm (m, 1H, CH$_2$OP), 3.95 ppm (t, 1H, CHCC), 3.90 ppm (d, 2H, CH$_2$CHCC), 3.75 ppm (m, 1H, CH$_2$OP), 2.70 ppm (br s, 2H, CH$_2$OP), 3.65 ppm (br s, 2H, CH$_2$OCO), 3.18 ppm (t, 2H, NCH$_2$), 2.08 ppm (t, 2H, CH$_2$COO), 1.35 ppm (m, 2H CH$_2$CH$_2$COO), 1.05 ppm (br s, 20H, (CH$_2$)$_{10}$), 0.70 ppm (t, 3H, CH$_3$).

1-Myristoyl-2-[12-methoxydodecanoyl]-sn-glycero-3-phosphoethanol-amine-fluorenylmethyloxycarbonyl (1-M-2-12MOGPE-Fmoc)

MMPE-Fmoc, MO-anhydride and DMAP were dried in a 45° C. vacuum desiccator for at least 4 hours. MMPE-Fmoc (154 μmol, 100 mg) was dissolved in freshly distilled THF in a flame dried round bottom flask, and 12-MO-anhydride (632 μmole, 280 mg) and DMAP (460 μmol, 56 mg) were also dissolved in distilled THF but in a separate flask. Both flasks were heated to 45° C. and after the reactants dissolved, MO-anhydride and DMAP were carefully transferred to the flask containing MMPE-Fmoc (20 mg reactant/ml solvent). The reaction mixture was purged with nitrogen and stirred. After 1 hour the reaction was cooled to room temperature and allowed to react for another 14 hours. The solvent was removed by rotoevaporation and a minimum volume of CHCl$_3$ (~1–2 ml) was used to dissolve the residue. Unreacted MO-anhydride was removed from the reaction mixture and the product was purified as described above for di-12MOGPE-Fmoc with the minor modification that the mobile phase solvent was solvent system B. The purified product (1-M-2-12MOGPE-Fmoc) exhibited one spot (Rf= 0.48) on TLC plates developed in solvent system B. 1-M-2-12MOGPE-Fmoc was Ninhydrin negative, phospray positive and UV positive. The yield was ~92% based on 1 reaction.

1-Myristoyl-2-[12-methoxydodecanoyl]-sn-glycero-3-phosphoethanolamine (1-M-2-12MOGPE)

FMOC was removed from 1-M-2-12MOGPE-Fmoc by piperidine and the lecithin product (1-M-2-12MOGPE) purified by flash chromatography as described above for di-12MOGPE. Similar to purification of di-12MOGPE, the purification of 1-M-2-12MOGPE was simple because Fmoc elutes at the solvent front whereas piperidine remains at the origin when CHCl$_3$/CH$_3$OH/H$_2$O/THF (64:34:7:30) is used as an isocratic solvent system during flash chromatography. The final product, 1-M-2-12 MOGPE, shows one spot on the TLC plates developed in solvent system A. 1-M-2-12-MOGPE is UV negative, and positive when sprayed with either Ninhydrin or Phospray. The yield was ~84% based on 1 reaction.

FAB-MS: MH$^+$ 638.5. IR (CaF$_2$, neat) results: $v_{as}$ CH$_2$ 2918.3; $v_s$ CH$_2$ 2850.6; v C=O 1739.0; δ$_{as}$ CH$_2$ 1467.4; $v_{as}$ PO$_2$ 1230.8; v C—O—C 1078.8; $v_s$PO$_2$ 1028.2. $^1$H NMR (500 MHz, CDCl$_3$), δ 5.18 ppm (br s, 1H, CH), 4.35 ppm (m, 1H, CH$_2$OP), 4.11 ppm (m, 1H, CH$_2$OP), 4.05 ppm (b s, 2H, CH$_2$OP), 3.90 ppm (br s, CH$_2$OCO), 3.33 ppm (t, 2H, OCH$_2$), 3.30 ppm (s, 3H, OCH$_3$), 3.12 ppm (br s, 2H, NCH$_2$), 2.28 ppm (m, 4H, CH$_2$COO), 1.55 ppm (m, 6H CH$_2$CH$_2$COO, CH$_2$CH$_2$OCH$_3$), 1.25 ppm (br s, 34H, (CH$_2$)$_7$, (CH$_2$)$_{10}$), 0.85 ppm (t, 3H, CH$_3$).

Preparation of DAC2, LPE1 and LPE2

The preparation of D-AC2 was identical to L-AC2 except D-glycerolphosphocholine, which was obtained from Synthetische Phosphor-Lipide, Biochemisches Labor, Bern CH Switzerland was used. L-PE2 was prepared by reacting glycerolphosphatidylethanolamine (L-α-GPE) with N-(9-Fluorenylmethoxycarbonyloxy) succinimide (FMOC-succinimide) to form L-α-GPE-FMOC followed by diacylation with 12MO anhydride then deprotection of FMOC with piperidine. L-PE1 was prepared by diacylating L-α-GPE-FMOC with myristic anhydride, then PLA2 cleavage to remove the sn-2 chain, then acylation with 12MO anhydride, and finally deprotection with piperidine to remove FMOC.

Scheme 1

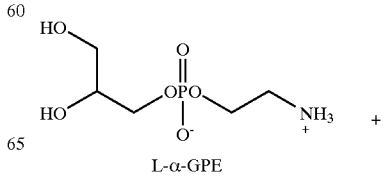

L-α-GPE

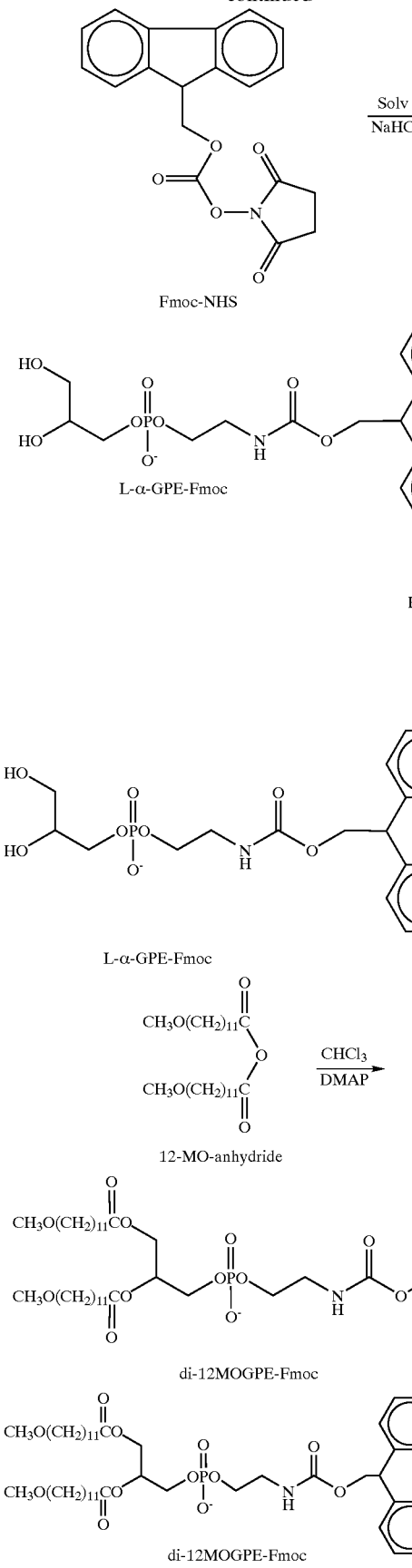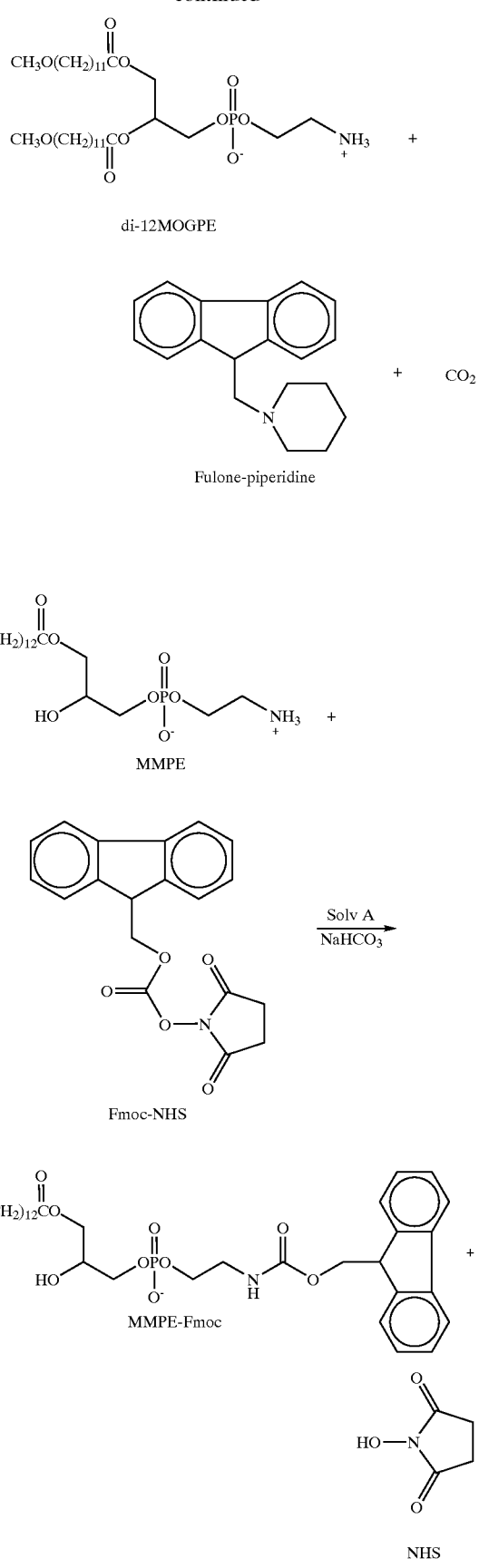

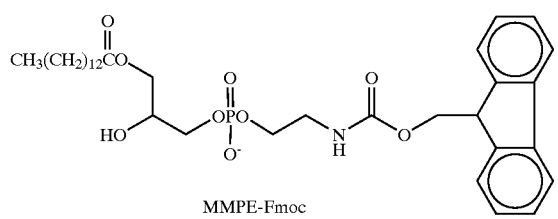

MMPE-Fmoc

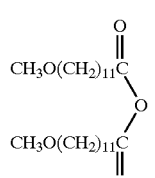

12-MO-anhydride

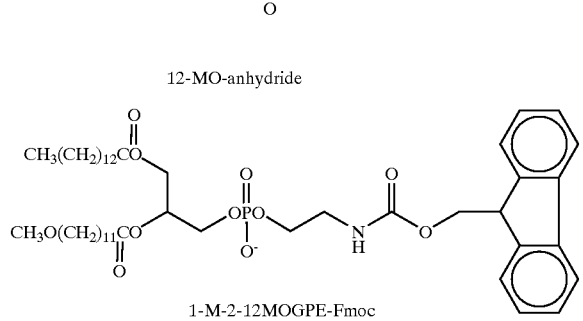

1-M-2-12MOGPE-Fmoc

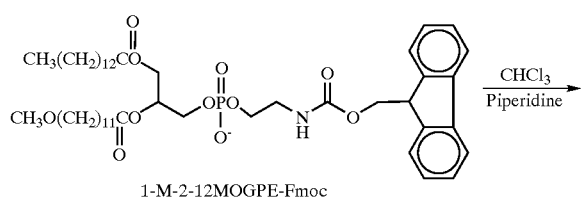

1-M-2-12MOGPE-Fmoc

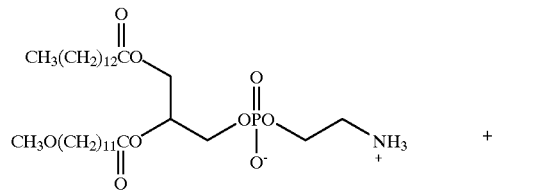

1-M-2-12MOGPE

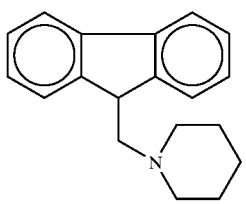

Fulone-piperidine

Scheme 3

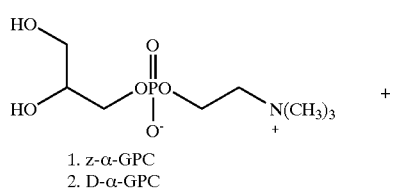

1. z-α-GPC
2. D-α-GPC

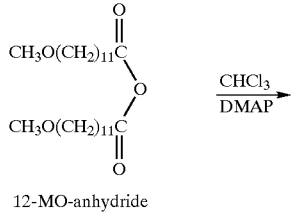

12-MO-anhydride

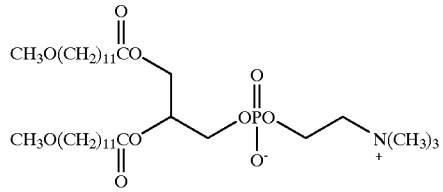

3. z-α-di-12MOGPC
2. D-α-di-12MOGPC

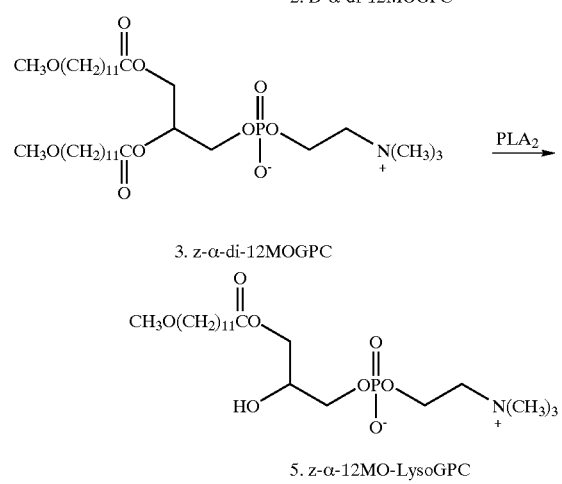

3. z-α-di-12MOGPC 5. z-α-12MO-LysoGPC

Single chain phospholipid analogs are known to form micelles, whereas double chain analogs form liposomes. After injection into animals or man, liposomes concentrate in macrophages, yet micelles do not. Thus, phospholipid analogs containing biologically active fatty acid molecules in the alkyl chains can be modified such that the dispersion properties of the phospholipids can be used to control, in part, the in vivo disposition of these anti-HIV drugs. Macrophages and T-cells are both CD4 positive cells and consequently, HIV avidly infects both of these cells. Thus, liposome forming anti-HIV drugs have unique application for combination therapy against HIV, particularly during viremia. If inhibitors of the HIV-CD4 binding interaction are found and employed for HIV therapy, then during viremia, HIV may not concentrate in T-Cells. However, this may cause the HIV infection to shift to other cells such as blood monocytes and macrophages, which internalize foreign particles regardless of the presence of CD4. The ability to control the in vivo disposition of, for e.g., phosphatidylcholine anti-HIV compounds, by changing the number of acyl chains on the phospholipids, is therefore significant.

It is believed that liposome forming anti-HIV active phospholipids will most likely not be able to treat HIV infected tissue macrophages because liposomes cannot efficiently exit the blood compartment of the host. However, single chain lysolipid analogs which form micelles are expected to distribute into tissues outside of the blood compartment since lysolipid analogs bind to albumin and are transported by albumin to different tissues.

The incorporation of biologically active fatty acids themselves into liposomes, for delivery to mononuclear phagocytic cells, will also concentrate the drug in blood monocytes/macrophages. However, no control over the incorporation of hetero-atom fatty acids into the cellular lipid pool exists for this delivery system. In contrast, feeding cells biologically active fatty acids covalently linked to particular phospholipids allows some control over the cellular disposition of the biologically active fatty acids. Thus a key concept for the delivery of biologically active fatty acids in the form of phospholipids is that the in vivo disposition of the drugs can be controlled by liposome forming analogs and the cellular disposition of biologically active fatty acids can be altered for therapeutic benefit by using specific phospholipid headgroups for the preparation of the drugs.

I. Experimental Designs and Methods Overview of Assay Methods

Three assays for anti-HIV activity were used and the $IC_{50}$ was calculated from these assays; (i) syncytial cell assays, (ii) reverse transcriptase assays, and (iii) direct cytotoxicity assays. In addition, direct drug cytotoxicity was tested 'as a control' in each assay which merely means that the drug was dosed to the cells without virus present. This control assured that only the antiviral effect of the compound is measured. However, this drug cytotoxicity was not used to calculate the $TC_{50}$ because the $TC_{50}$ required doses of drug that were higher than the effective concentrations. Thus the $TC_{50}$ is the dose of drug that kills 50% of the cells without virus present and was measured in MTT assays using the same cells type to evaluate antiviral activity. The therapeutic index was calculated from $TC_{50}/IC_{50}$. The ability of anti-HIV phospholipids to inhibit direct cytopathic effect caused by HIV infection was also measured.

Anti-HIV Activity of AC2, AC1, lysoAC2 and 12MO Viral Stocks

The S5G7 strain of HIV was used. S5G7 is a subclone of HTLVIIIB grown in H9 cells, and highly virulent regarding T cell infectivity, but less so for monocytes; this strain was obtained from Abbott Laboratories.

Anti-HIV Activity: (1) Direct Cytotoxicity Assay

This assay measures the ability of a drug to inhibit the HIV virus from killing cells. CEM cells were used for this assay. The protocol is given in the next two paragraphs.

The T-cell HIV inhibition assay method of acutely infected cells is an automated tetrazolium based calorimetric assay adapted from Novak, et al., *Aids Res. and Human Retroviruses*, 6, 973 (1990). Assays were performed in 96-well tissue culture plates. CEM cells were grown in RPMI-1640 medium (Gibco) supplemented with 10% fetal calf serum and were then treated with polybrene (2 $\mu$g/ml). A 80 $\mu$l volume of medium containing $1\times10^4$ cells was dispensed into each well of the tissue culture plate. To each well was added a 100 $\mu$l volume of test compound dissolved in tissue culture medium (or medium without test compound as a control) to achieve the desired final concentration and the cells were incubated at 37° C. for 1 hour. A frozen culture of HIV-1 was diluted in culture medium to a concentration of $5\times10^6$ $TCID_{50}$ per ml ($TCID_{50}$=the dose of virus that infects 50% of cells in tissue culture), and a 20 $\mu$l volume of the virus sample (containing 1000 $TCID_{50}$ of virus) was added to wells containing test compound and to wells containing only medium (infected control cells). This results in a multiplicity of infection of 0.1 (MOI=# of infectious virus particles/# of cells in culture). Several wells received culture medium without virus (uninfected control cells). Azidothymidine (AZT) was tested as a positive drug control. Test compounds were dissolved in DMSO and diluted into tissue culture medium so that the final DMSO concentration did not exceed 1.5%. DMSO had no significant effect on results as determined in controls.

Following the addition of virus, cells were incubated at 37° C. in a humidified, 5% $CO_2$ atmosphere for 7 days. Additional aliquots of test compounds were added on days 2 and 5. On day 7 post-infection, the cells in each well were resuspended and a 100 $\mu$l sample of each cell suspension was removed for assay. A 20 $\mu$l volume of a 5 mg/ml solution of 3-(4,5-dimethylthiazol-2-yl)-2,5-diphenyltetrazolium bromide (MTT) was added to each 100 $\mu$l cell suspension, and the cells were incubated for 4 hours at 37° C. in 5% $CO_2$ environment. During this incubation, MTT is metabolically reduced by living cells resulting in the production in the cell of colored formazan product. To each sample was added 10 ml of 10% sodium dodecylsulfate in 0.01N HCl to lyse the cells, and samples were incubated overnight. The absorbance of each sample was determined at 590 nm using a Molecular Devices microplate reader. The % reduction of the virus induced cytopathic effect (CPE) by the test compounds was calculated from the equation.

$$\% \text{ reduction } CPE = \frac{(\text{Abs compound-treated infected sample}) - (\text{Abs of virus control})}{(\text{Abs of cell control}) - (\text{Abs of virus control})} \times 100$$

The direct cytotoxicity of each compound to CEM cells is labeled above each histogram bar in FIG. 1. Starting from the top graph in FIG. 1, AC1 was not toxic to the CEM cells at dose up to 400 $\mu$M, AC2 was toxic to CEM cells at 400 $\mu$M, lysoAC2 was not toxic up to 400 $\mu$M, and 12MO was toxic to CEM cells at 400 $\mu$M but 12MO also showed toxicity at 40 $\mu$M. 12MO was the most toxic analog tested in this series.

The $IC_{50}$ of AC2 could not be accurately determined from the data because the activity was too high but the $IC_{50}$ is less than 4 $\mu$Molar, and it is estimated that the $IC_{50}$ is ~1 $\mu$M. It is also interesting that anchoring the biologically active fatty acid in the sn-2 position significantly reduced the activity (i.e., AC1 top graph), but the lysolecithin analog containing the biologically active fatty acid in the glycero sn-1 position was active with an $IC_{50}$ ~100 $\mu$Molar. This may be due to the metabolism of lysolipids compared to diacylated lipids or it may indicate the myristoyl group is stored in the sn-1 chain of endogenous membrane lipids. AC1 and the lyso compound were significantly less toxic than the biologically active fatty acid of AC2.

Anti-HIV Activity: (2) Macrophages

Anti-HIV activity was next measured in macrophages using a p24 antigen capture assay. The assay protocol is outlined below.

Figure 2:
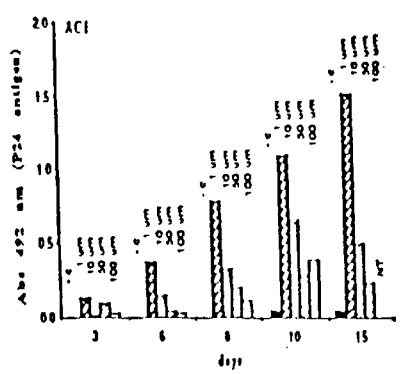
FIGS. 2(A–C) shows the anti-HIV activity in macrophages of L-AC1, L-AC2 and 12MO measured with an HIV p24 antigen assay.
Figure 2:
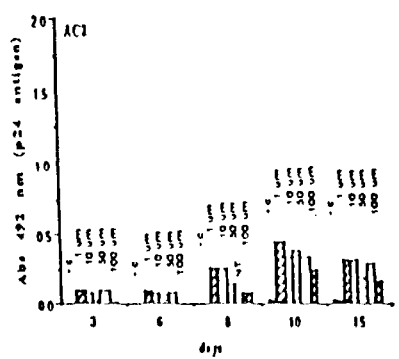
Figure 2:
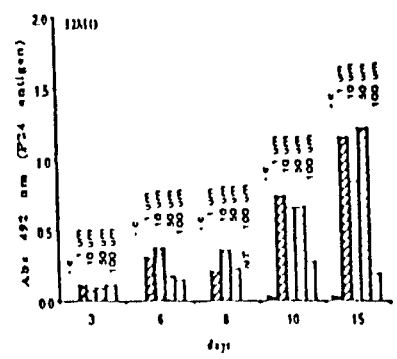

Absorbance values (492 nm) for HIV-1 p24 antigen were detected by enzyme-immunoassay (EIA) in culture supernatants of HIV-1 (3B) infected monocyte-derived macrophages (MDM). Human peripheral blood MDM were prepared by adherence to plastic in 24-well tissue culture plates (Costar, Cambridge, Mass.). Briefly, $1\times10^7$ Ficoll-Paque (Pharmacia, Piscataway, N.J.) gradient purified mononuclear cells in RPMI-1640 with 20% heat-inactivated fetal bovine serum, L-glutamine, and gentamycin (Gibco, Grand Island, N.Y.) were placed in each well and allowed to adhere at 37° C. for 3 hours. Non-adherent cells were removed by gentle washing with warm (37° C.) Hank's balanced saline solution (HBSS-Gibco) and the cells incubated in a 5% $CO_2$ in air atmosphere at 37° C. in 2 ml of media. Remaining non-adherent cells were further removed by washing again after 24 hours and 5 days. After 7 days in culture, the cells were infected with HIV-1 3B by removing the media from each well, washing with HBSS and adding 0.2 ml of virus-containing supernatant from a 5 day culture of a MDM permissive subclone of HIV-1 3B grown in H9 cells. The plate was rocked at 37° C. for 3.5 hr, the viral inoculum removed and the cells washed 3 times each with 2 ml of warm HBSS to remove non-MDM-associated viral particles. Media containing 0, 1, 10, 50 or 100 μM of AC1, AC2 or 12MO were added to the appropriate wells and the cells incubated as previously described. On days 1, 3, 6, 8, 10 and 15 after infection, 200 μl of supernatants were removed from each well for p24 antigen EIA assay (HIVAG-1; Abbott Laboratories, North Chicago, Ill.). On day 8, following the sampling for p24 antigen, 1 ml of fresh media containing AC1, AC2, or MO was added to the appropriate wells to restore a concentration of 1, 10, 50 or 100 μM of each compound. Data is presented as absorbance values reflecting HIV-1 p24 antigen concentration produced by infected MDM as detected in culture supernatants. The experiment shown in FIG. 2 is representative of 3 experiments using 3 cell donors. In FIG. 2 the dose of drug is given above each bar in the histogram, and −C is the negative control (no virus, no drug).

FIG. 2 shows that AC2 was very potent and completely inhibited the AIDS infection in macrophages at all doses tested. Even at the low dose of AC2, i.e., 1 μM, AC2 was completely effective. AC1 gave a dose response with almost complete inhibition at 100 μM. 12MO exhibited little activity except at 100 μM where the HIV infection was completely suppressed. At this concentration, however, 12MO was toxic.

Anti-HIV Activity: (3) Syncytial Cell Assays

Figure 3:
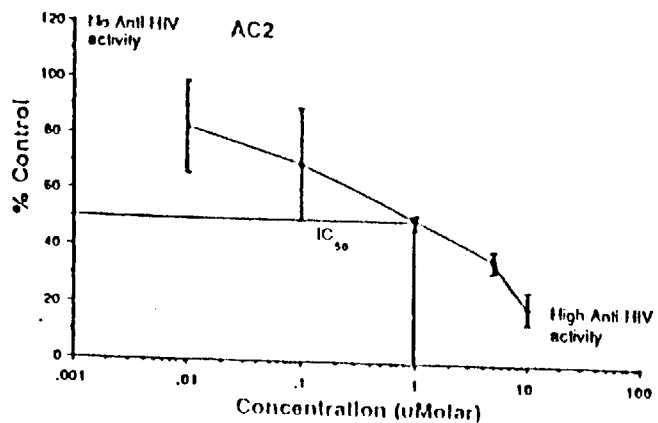
FIGS. 3(A–B) depicts the anti-HIV activity of L-AC2 and 12MO in MT-4 cells using syncytial cell assays.
Figure 3:
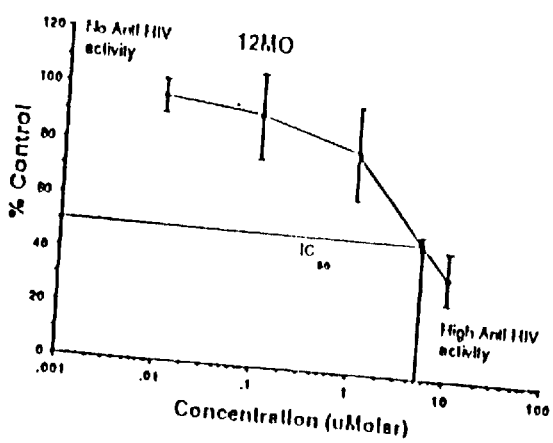

Briefly, the assay was performed as follows. On Day 0, MT4 cells were infected with HIV. On Day 3, mix $10^3$–$10^4$ infected cells (resuspend cells at $10^4$–$10^5$ cells/ml so that the desired number of cells is in a volume of 100 μl) with $10^5$ SupT1 cells (suspended at $10^6$/ml, so that there are $10^5$ cells per 100 μl) in a 96 well plate. Infected cells are titered to find the optimum number of syncytial cells to count. Cells are counted either manually or by flow cytometry. Syncytia begin to form at 8–10 hours, but optimum time for MT4 cells is about 18 hours. The time intervals for other cell lines may vary. To assay drugs that block syncytia formation, 50 μl SupT1, 50 μl infected (MT4) cells (total cell number is the same), and 100 μl of drug are present. Typical results are shown in FIG. 3 which compares the $IC_{50}$ of AC2 to 12MO. The $IC_{50}$ of AC2 is ~1 μM and the $IC_{50}$ of 12MO is ~4 μM.
Antiviral Activity in PHA-Lymphoblasts: (4) Reverse Transcriptase Assay Mononuclear cells were obtained from the whole blood of normal donors by ficoll/Hypaque (Pharmacia) density gradient centrifugation. These cells are initially washed with buffer and then stimulated with PHA-M (Gibco) for 72 hours. The cells are then counted for number, and also viability using trypan blue exclusion, followed by infection with S5G7, a subclone of HTLVIIIB or a wild type strain, at a multiplicity of infection (MOI) of 0.2 (i.e., 1 virus/5 cells) in a volume of 0.2 ml of culture supernatants for 2 hours at 37° C. Control cells not challenged with virus are used to evaluate drug toxicity. Cells are then washed three times in RPMI+10% fetal calf serum (FCS) and plated in a 96-well tissue culture plate in RPMI+10% FCS, 10 mM L-GLN, 10 mM Sodium pyruvate, IL-2, gentamicin. Cells are refed every 24 hours with complete media containing replacement drug and IL-2. Seven days after infection, samples are taken for the reverse transcriptase assay. These samples are frozen at −70° C. until analysis.

The procedure for measuring RT (reverse transcriptase) activity can be routinely performed by one of ordinary skill. Briefly, 50 μl of HIV culture supernatant are mixed with 50 μl of a 2×RT assay buffer containing Tris, 0.1M, pH 7.9, KCl, 0.32M, dithiothreitol, 0.012M, MgCl$_2$, 0.012M, reduced glutathione, 1.2 mM, ethylene glycolbis(beta-aminoethylether)-N,N,N',N'-tetraacetic acid, 1 mM, ethylene glycol, 4%, sterile, distilled water, 10 μl, Triton X-100, 0.2%, template primer poly(rA).p(dT), 1 μ/ml, 0.05 μ/sample, (Pharmacia), and 10 μCi$^3$H-dTTP (Amersham). Samples are incubated for 24 hours at 37° C. in microtiter plates, after which the reaction is stopped with 200 μl cold 10% tetrachloroacetic acid containing 0.2 M sodium PPi. The plate is then allowed to incubate for 2 hours on ice, after which, samples are harvested onto DE-81 filter paper discs (Whatman) using a cell harvester. The discs are washed 8 times in 5% trichloroacetic acid and absolute ethanol, dried and placed into glass scintillation vials. They are then counted on a beta scintillation counter. Negative (uninfected cell supernatants are used to determine the background DNA polymerase activity, if any) and known positive controls are assayed simultaneously. Results measured in counts per minute (cpm) are plotted as % of the control (i.e., cpm obtained without drug present but with virus infection) as shown in FIG. 4.

Figure 4:
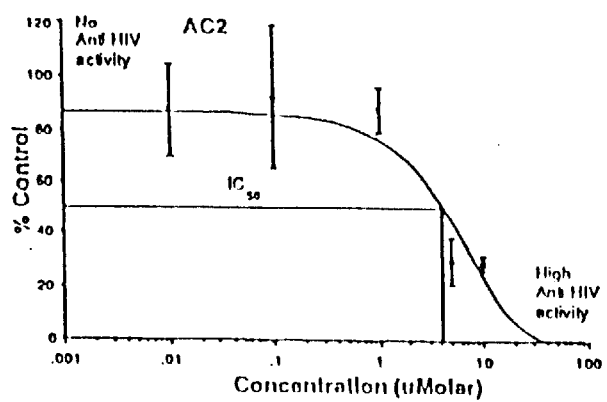
FIGS. 4(A–B) depicts the antiviral activity of L-AC2 and 12MO in peripheral blood monocytes (PBMC's) measured by reverse transcriptase assay. The results are depicted as the % of control.
Figure 4:
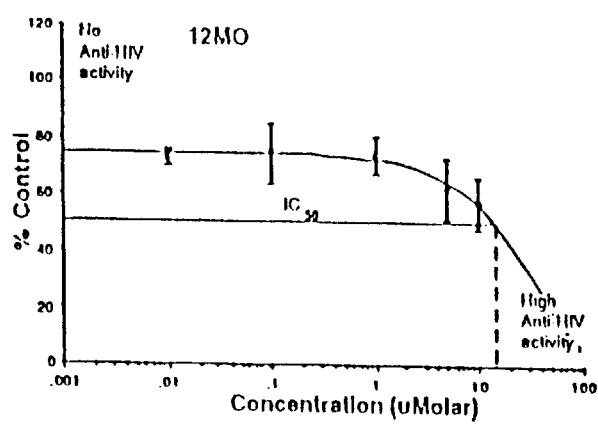

FIG. 4 shows that the IC50 of AC2 is ~4 μM and the IC50 of 12MO is ~12 μM in this reverse transcriptase assay.

Drug Cytotoxicity Using MTT Assay (Calculation of TC$_{50}$)

MT4 cells were plated in 96-well microtiter plates at 8×10$^4$ cells/well in a volume of 90 μl. [Note: To compare TC50 to IC50, the same cell type used in antiviral assays was tested in the MTT assay; for these experiments, MT4 cells were used to evaluate the syncytial cell assays and PBMC's were used to compare the PBMC/RT assay]. To this was added one minimum cytotoxic dose of HIV in a volume of 10 μl. The test drug was added in 100 μl aliquots at several concentrations. A control plate using uninfected MT4 cells was set up simultaneously to assess cytotoxicity due to the drug alone. The plates were then incubated for five days at 37° C. Then the media was aspirated from the wells and replaced with 100 μl MTT solution (3-(4,5-dimethylthiazol-2-yl)-2,5-di-phenyltetrazolium bromide, 1 mg/ml in PBS) and incubated for 4 hours at 37° C. The plates were then centrifuged to pellet the cells, and the supernatants were removed (centrifugation can be omitted if the supernatants are removed carefully). Acidic isopropanol (0.04N HCl in isopropanol), 100 μl, was then added to the wells and shaken for 15–30 minutes to dissolve the formazan crystals. Plates were read on an ELISA reader at Abs 570 nm. The difference between the uninfected and infected plates represent the antiviral activity of the drug. This assay was used to determine drug toxicity alone. A similar method has been described in the AIDS Research and Reference Reagent Program Courier, 90–01:8–9, 1990.

Figure 5:
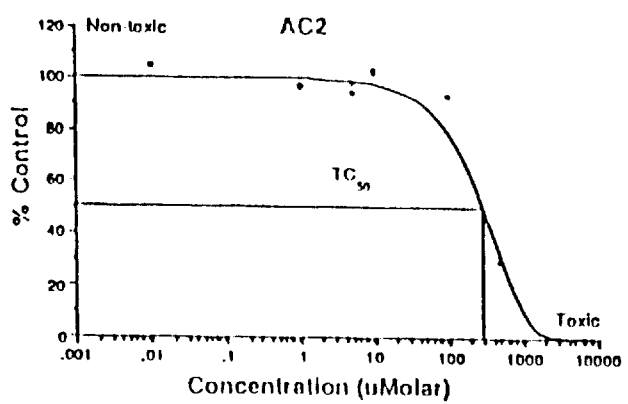
FIGS. 5(A–B) demonstrates the toxicity activity of L-AC2 and 12MO used to evaluate the concentration of drug that kills 50% of MT-4 cells in the absence of virus. Dose response curves were used to evaluate the concentration of drug that kills 50% of MT4 cells. This 50% effective toxicity to cells is denoted as TC50 in each graph.
Figure 5:
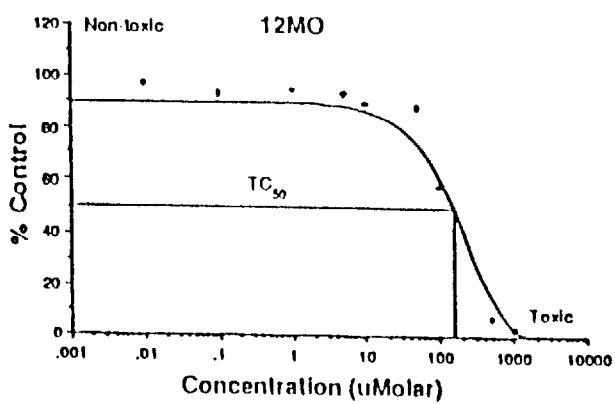

FIG. 5 shows the results of a typical experiment run in MT 4 cells which can be compared directly to the syncytial cell assay shown in FIG. 3 because the same cell line was used. The TC50 of AC2 was 280 μM and the TC50 of 12MO was 140 μM as shown in FIG. 5.

Therapeutic Index of Lipids Having Anti-HIV-activity

Table 1 summarizes the data shown in FIGS. 1–5 by comparing the therapeutic index for 12MO and AC2. The therapeutic index compares the toxic dose (TC50) to the effective dose (IC50). The therapeutic index values given in Table 1 are calculated from toxicity data and activity data that were obtained in the same cell line. In syncytial cell assays using MT 4 cells the therapeutic index for AC2 is 280 whereas for 12MO the therapeutic index is only 35. In PBMC's, the therapeutic index for AC2 is 31 whereas for 12 MO the therapeutic index is 37.

Moreover, L-AC2 was significantly more potent than 12MO in HIV infected monocyte-derived macrophages (MDM) shown in FIG. 1. During a 15 day acute infection, L-AC2 at 1 μM completely suppressed the HIV infection in MDM yet 12MO had little activity at doses from 1 to 50 μM. However, the 100 μM dose of 12MO suppressed HIV replication in MDM which demonstrates that 12MO exhibited a very steep dose response effect in MDM i.e., little activity at 50 μM and virtually 100% activity at 100 μM. No dose response was observed in MDM for L-AC2 because the lowest dose of L-AC2 tested (1 μM) completely inhibited the HIV infection in MDM.

In HIV infected MDM, L-AC1 exhibited dose responsive activity and 50 μM L-AC1 completely suppressed HIV p24 antigen production; this dose of L-AC1 had little activity in CEM cells using a direct cytopathic assay (FIG. 1). Diacylated phospholipids form liposomes, and as expected both L-AC1 and L-AC2 formed liposomes in aqueous buffers. The increased activity of L-AC1 in MDM compared to CEM cells may be due to the phagocytosis of L-AC1 liposomes in MDM.

L-AC2 and AZT is not due to increased cellular toxicity from administering both drugs concurrently; it is believed that the synergism is due to direct inhibition of HIV by two different mechanisms. AZT is a reverse transcriptase inhibitor; whereas, L-AC2 putatively inhibits endogenous myristoylation of the HIV proteins.

Anti-HIV Activity of D-AC2

L-AC2 contains the natural configuration of glycerophosphocholine and is quantitatively hydrolyzed by bee venom phospholipase A2 (PLA2) within minutes. PLA2s stereospecifically hydrolyze phospholipids. However, the D-isomer, i.e., D-AC2 was prepared to test the hypothesis whether

TABLE 1

$IC_{50}$ and Therapeutic Index of L-AC2 and 12MO

|  | $TC_{50}$ Cytotoxicity[a] MTT Assay μM | $IC_{50}$[b] 50% Reduction in syncytial cell formation MT4 cells[d] μM | Therapeutic Index[c] MT4 cells | $IC_{50}$[b] 50% Reduction in Reverse Transcriptase Activity PBMC[e] μM | Therapeutic Index[c] PBMC |
|---|---|---|---|---|---|
| 12 MO | 140 (MT4 cells) | 4 | 35 | | |
| | 340 (PBMC cells) | | | 19 | 17 |
| L-AC2 | 280 (MT4 cells) | 1 | 280 | | |
| | 220 (PBMC cells) | | | 6 | 37 |

[a]Drug cytotoxicity in the absence of HIV was determined using MT4 cells or PBMC's. The $TC_{50}$ is the concentration of the drug that killed 50% of the cells during a 4 hour incubation period.
[b]The $IC_{50}$ is the drug concentration that inhibited 50% of the maximum HIV response which was observed when no drug was present. The HIV responses that were measured are syncytial cell formation or reverse transcriptase activity.
[c]The therapeutic index was calculated as $TC_{50}/IC_{50}$.
[d]Syncytial cell assays were performed using MT4 cells infected with HIV and SupT1 cells as target cells. MT4 cells are CD4+ and highly susceptible to HIV infection.
[e]Drug activity was determined in PBMC by measuring inhibition of reverse transcriptase activity.

Compounds of the present invention (IV, V, VI), especially those containing at least one heteroatom fatty acid acyl chain, exhibit synergistic effects when administered with AZT. The more preferred embodiments (compounds of formulae VIII–XV) also exhibit this effect. An illustrative example is given hereinbelow.

Synergism of AC2 with AZT

Another set of data demonstrates the synergism observed with AC2 and AZT in syncytial cell assays using T cells.

Figure 6:
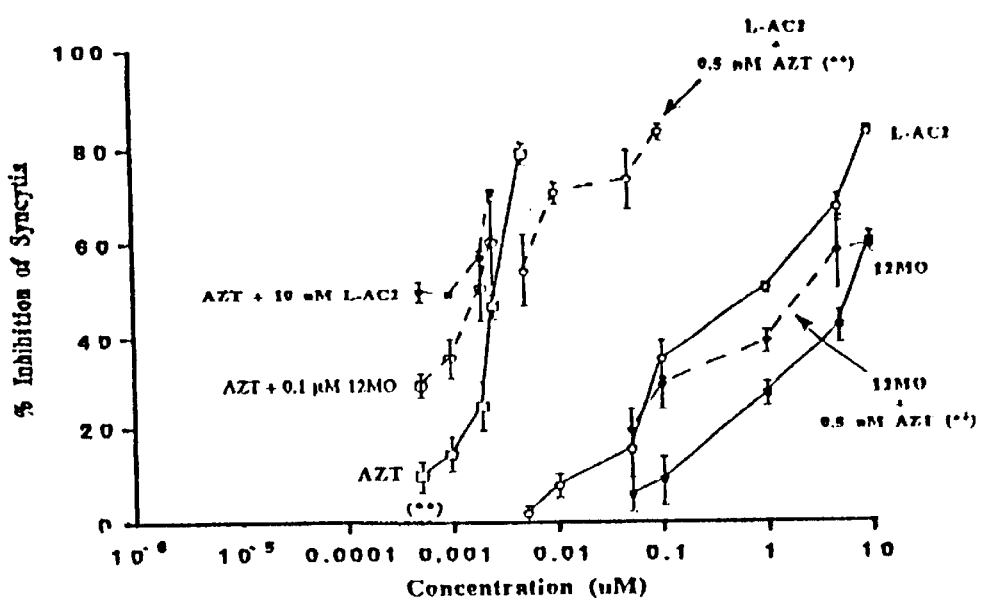
FIG. 6 depicts the potent anti-HIV synergism when L-AC2 and AZT are concurrently administered.

12MO has been reported to act synergistically when administered concurrently with AZT, and the synergism between AZT and either 12MO or L-AC2 using syncytial cell assays was evaluated. (FIG. 6). The dose response curves for each drug alone shows that AZT is ~100 times more potent than L-AC2; however, AZT is ~$10^3$ to $10^4$ times more potent than 12MO. Synergism was evaluated by the shift in the dose response curves when 0.5 nM AZT (an inactive concentration) was added to 12MO and L-AC2; 12MO exhibited less than a factor of 10 increase in activity whereas L-AC2 exhibited approximately 100 fold increased activity (FIG. 6). For instance, FIG. 6 shows that 5 nM L-AC2 (an inactive concentration labelled ** in FIG. 6) and 0.5 nM AZT (an inactive concentration) exhibited ~50% inhibition of syncytia formation in HIV infected MT4 cells. FIG. 6 also shows that 10 nM L-AC2 (an inactive concentration) shifts the dose response curve of AZT approximately 100 fold. Using MT4 cells, concentrations of AZT from 50 nM to 500 nM did not alter the concentration of L-AC2 that killed 50% of uninfected cells, i.e., the $TC_{50}$ of L-AC2 is unchanged in the presence of AZT.

Figure 7:
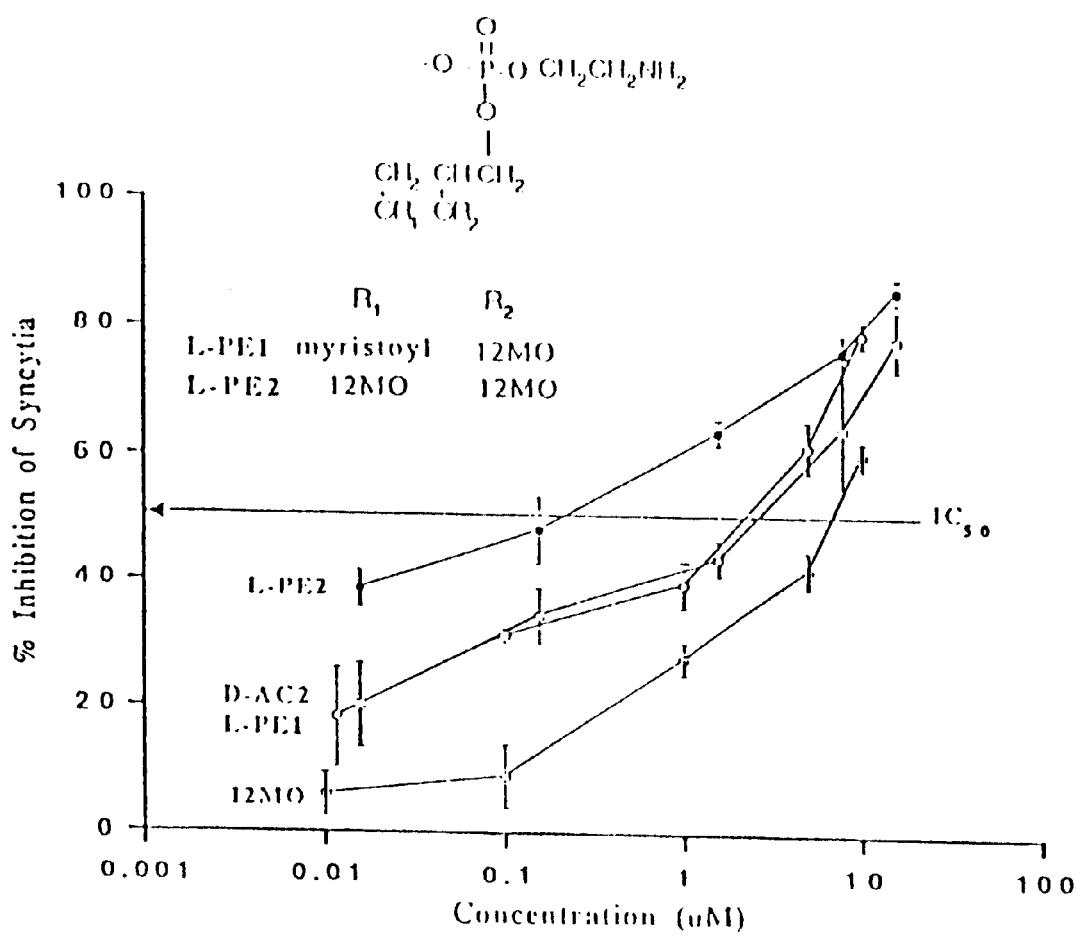
FIG. 7 depicts the anti-HIV activity of D-AC2 (unnatural glycerophosphatidyl choline configuration) and phosphatidylcholine (PE) analogs, L-PE-1 and L-PE-2 compared with 12MO.

FIG. 6 clearly shows the increased synergistic effects of L-AC2 with AZT as compared with 12MO and AZT. Without wishing to be bound, it is believed that the synergism for endogenous PLA2s are responsible for 12MO release from phosphatidylcholine analogs containing 12MO. FIG. 7 shows that the $IC_{50}$ for D-AC2 is ~1 uMolar which is identical to the $IC_{50}$ of L-AC2. Unlike L-$AC_2$, D-AC2 is not hydrolyzed by PLA2.

FIG. 7 also shows the anti-HIV activity of the phosphatidylethanolamine (PE) analogs L-PE1 and L-PE2; these analogs are chemically similar to L-AC1 and L-AC2 respectively except the PC headgroup has been changed to the PE headgroup. The $IC_{50}$ of L-PE1 and L-PE2 are 6 uMolar and 0.02 uMolar respectively; compared to the PC analogs this is approximately a 20–50 fold increase in activity. The anti-HIV activity of L-PE2 is >100 fold more than 12MO (FIG. 7).

Stability of Anti-HIV Phlospholipids in Fresh Blood at 38° C.

Figure 8:
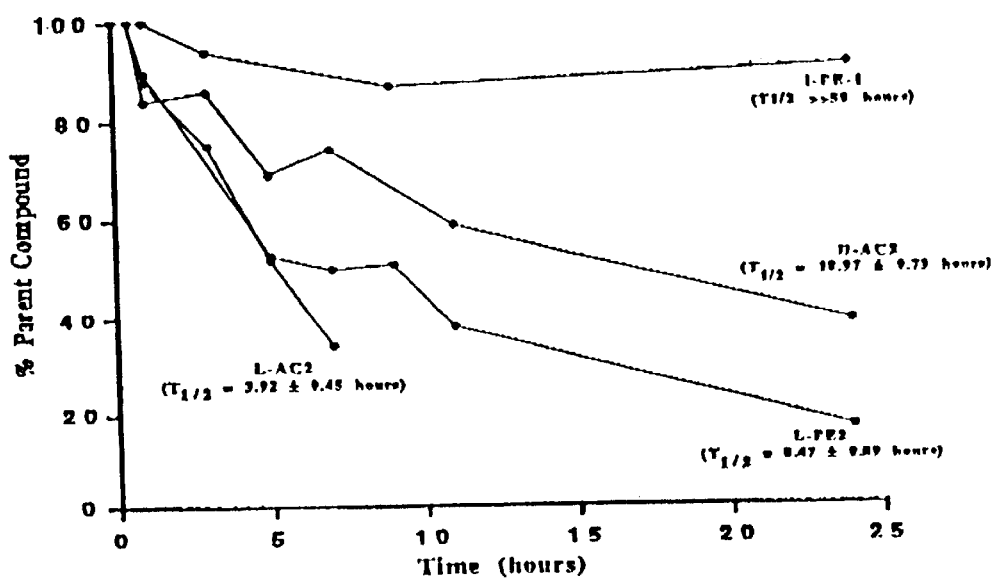
FIG. 8 depicts the stability of various anti-HIV phospholipids, L-PE1, L-AC2, D-AC2 and L-PE2 in fresh blood at 38° C.

Drug development using phospholipids will require that the parent compound is stable in blood. FIG. 8 shows that the halflife of L-AC2 in fresh blood is 4.56 hours and the halflife of D-AC2 is 18.24 hours (~4 times longer). Thus, by changing the stereochemistry of the glycerobackbone to the unnatural configuration the halflife in blood can significantly be increased. Changing the lipid headgroup also increases the stability in blood. L-PE2 has a halflife in fresh blood of 9.36 hours which is approximately 2 times longer than L-AC2 (FIG. 8). It was very surprising that L-PE1 has a very long halflife (T½>50 hours) compared to the L-PE2. L-PE1 and L-PE2 are identical except that the methylene group in the 13 position of the sn-2 alkyl chain has been replaced with an oxygen atom.

Without wishing to be bound, it is believed that the increased activity, particularly of L-AC2 and L-PE2 compared to 12MO, and also the increased synergism of L-AC2 with AZT compared to 12MO and AZT is due to the cellular disposition of phospholipid analogs. When 12MO is delivered to cells as a free fatty acid it is rapidly incorporated into triglycerides and membrane lipids. The T2 for incorporation is approximately 1–2 minutes. Triglycerides are usually thought of as storage depot for fats that are used as a source of energy. If intracellular triglycerides containing 12MO are used primarily as an energy source instead of a source of fatty acids for myristoylation of HIV proteins, then this may be the primary reason why the cellular availability, necessary for anti-HIV activity, of 12MO is 10 fold or 100 fold less than L-AC2 and L-PE2. Thus lipid metabolism and the intracellular disposition of hetero atom fatty acids and anti-HIV phospholipids can significantly affect anti-HIV activity.

The data in the figures and the Table clearly illustrate that acylation of a drug containing a carboxy group to the hydroxy group of the glycerol backbone of a phospholipid significantly enhances the pharmacokinetics of said drug. The phospholipid drug has an increased therapeutic index relative to the non-phospholipid drug. The phospholipid drugs prepared in accordance with the present invention can be more potent (FIG. 1), less toxic (FIG. 1), and more stable (FIG. 8), and can have increased availability or distribution relative to the non-phospholipid drug. The enhanced pharmokinetics of the phospholipid drugs prepared in accordance with the present invention makes it an extremely powerful weapon in the war against diseases.

The foregoing description of the invention has been presented for purposes of illustration and description and is not intended to be exhaustive or to limit the invention to the precise form disclosed. Other variations are possible in light of the teachings presented herein.

What is claimed is:

1. A pharmaceutical composition comprising a pharmaceutically effective amount of a compound of the formula:

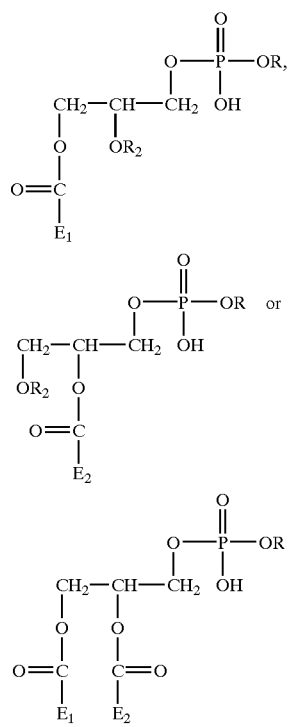

or pharmaceutically acceptable salts thereof and a pharmaceutically acceptable carrier therefor wherein R is a naturally occurring polar head group characteristic of a glycerophospholipid isolated from endogenous sources, $R_1$ and $R_2$ are independently hydrogen or an alkyl fatty acid acyl group having 4–26 carbon atoms and each $E_1$ and $E_2$ are independently a heteroatom hydrocarbyl group having 3–25 carbon atoms wherein one of the carbon atoms in the principal chain is replaced by S, wherein such substitution does not occur on the α-carbon to the acyl group or on the omega carbon.

2. A pharmaceutical composition comprising a pharmaceutically effective amount of a compound of the formula:

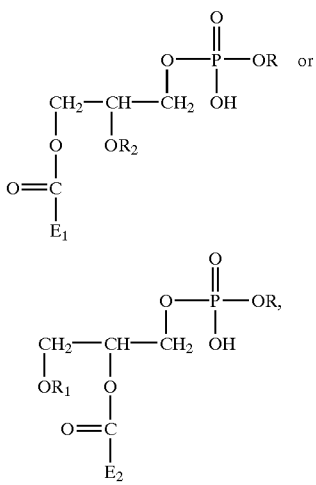

or pharmaceutically acceptable salts thereof and a pharmaceutical carrier therefor wherein R is a naturally occurring polar head group characteristic of a glycerophospholipid isolated from endogenous sources;

$R_1$ and $R_2$ are hydrogen and $E_1$ and $E_2$ are independently heteroatom hydrocarbyl group having 3–25 carbon atoms, wherein at least one of the carbon atoms in the principal chain is replaced by S or O, wherein said substitution does not occur on the α-carbon to the acyl group or on the omega carbon.

3. A pharmaceutical composition comprising a pharmaceutically effective amount of a compound of the formula:

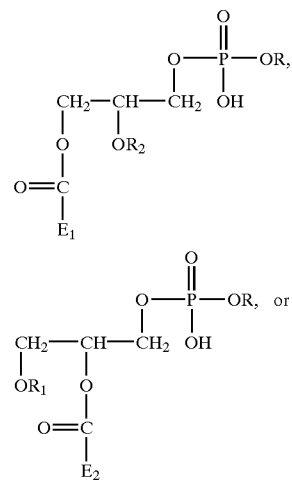

-continued

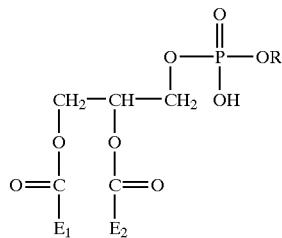

or pharmaceutically acceptable salts thereof and a pharmaceutical carrier therefor wherein R is CH$_2$CH$_2$NR$_8$R$_9$

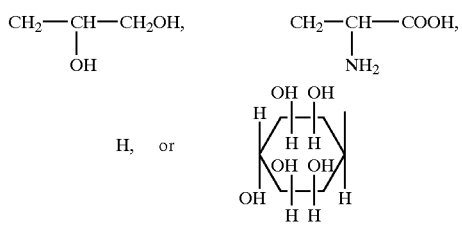

R$_1$ and R$_2$ are independently hydrogen or an alkyl fatty acid acyl group having 4–26 carbon atoms and E$_1$ and E$_2$ are independently heteroatom hydrocarbyl group having 3–25 carbon atoms, wherein one of the carbon atoms in the principal chain is replaced by O or S, and said substitution does not occur on the α-carbon to the acyl group or on the omega carbon and R$_8$ and R$_9$ are independently hydrogen or lower alkyl.

4. A pharmaceutical composition comprising a pharmaceutically effective amount of compound of the formula:

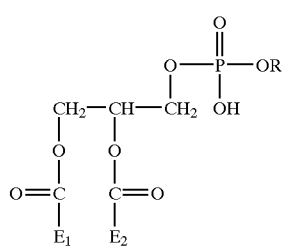

or pharmaceutically acceptable salts thereof and a pharmaceutical carrier therefor wherein R is a naturally occurring polar head group characteristic of a glycerophospholipid isolated from endogenous sources, E$_1$ and E$_2$ are the same and are heteroatom hydrocarbyl group having 3–25 carbon atoms which may be straight chained or branched wherein one of the carbon atoms in the principal chain is replaced by O or S, said substitution does not occur on the α-carbon to the acyl group or on the omega carbon.

5. The pharmaceutical composition according to claim 1, 2, 3 or 4 wherein the configuration at the carbon in the sn-2 position of said compound is L.

6. The pharmaceutical composition according to claim 1, 2, 3 or 4 wherein the configuration at the carbon in the sn-2 position of said compound is D.

7. The pharmaceutical composition according to claim 1, 2, 3 or 4 wherein said compound is substantially pure.

8. The pharmaceutical compositions according to claim 1, 2 or 4 wherein R is:

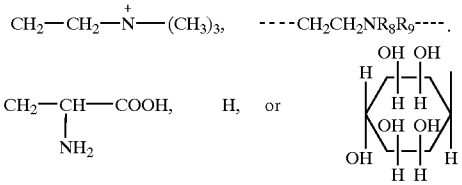

and R$_8$ and R$_9$ are independently hydrogen or lower alkyl.

9. The pharmaceutical compositions according to claim 1, 2, 3 or 4 wherein R$_1$ and R$_2$ are independently hydrogen or an alkyl fatty acid acyl group having 4–18 carbon atoms.

10. The pharmaceutical compositions according to claim 9 wherein R$_1$ and R$_2$ are independently an alkyl fatty acid acyl group having 4–8 carbon atoms.

11. The pharmaceutical compositions according to claim 1 having the formula:

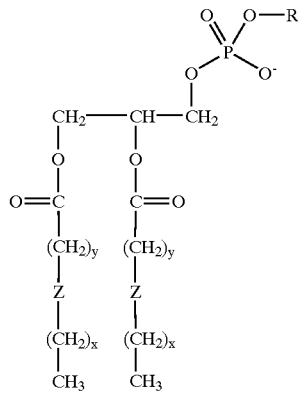

or pharmaceutically acceptable salts thereof wherein
R is a naturally occurring polar head group characteristic of a glycerophospholipid isolated from endogenous sources, one Z is S and the other is O or S;
each x may be the same or different and x=0–13, and
each y may be the same or different and y=1–13, and x+y=11–15.

12. A pharmaceutical composition comprising a pharmaceutically effective amount of a compound having the formula:

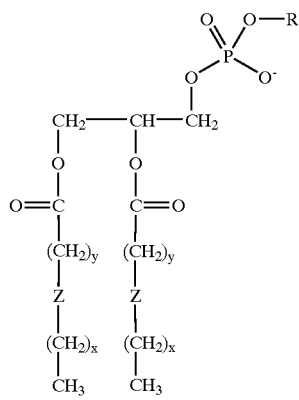

or pharmaceutically acceptable salts thereof and a pharmaceutical carrier therefor wherein
R is a naturally occurring polar head group characteristic of a glycerophospholipid isolated from endogenous sources, both Z's are the same or different and are O or S, each x may be the same or different and x=0–13,
each y may be the same or different and y=1–13 and x+y 11–15.

13. The pharmaceutical compositions according to claim 3 having the formula:

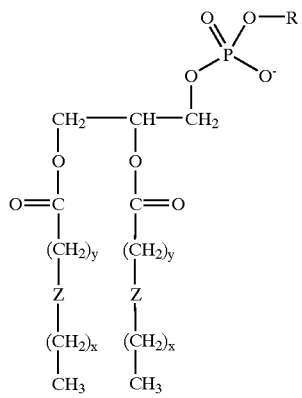

or pharmaceutically acceptable salts thereof wherein each Z is independently or S

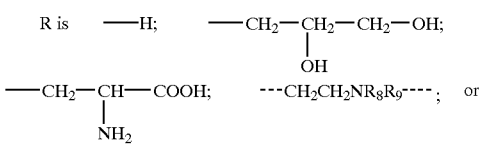

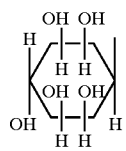

$R_8$ and $R_9$ are independently hydrogen or lower alkyl,
each x may be the same or different and x=0–13,
each y may be the same or different and y=1–13 and x+y=11–15.

14. The pharmaceutical compositions according to claim 4 having the formula:

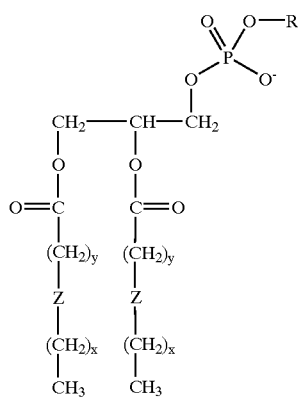

or pharmaceutically acceptable salts thereof wherein
R is a naturally occurring polar head group characteristic of a glycerophospholipid isolated from endogenous sources,
each x may be the same or different, and x=4–13,
each y may be the same or different, each y=1–13, and x+y=11–15, and Z is independently O or S.

15. The pharmaceutical compositions according to claim 11 wherein R is

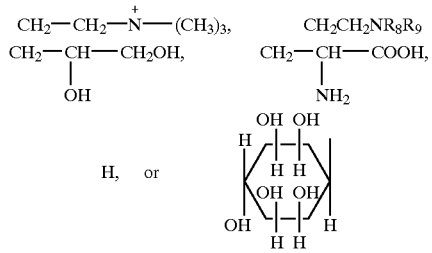

and $R_8$ and $R_9$ are independently hydrogen or lower alkyl.

16. The pharmaceutical compositions according to claim 12 wherein R is

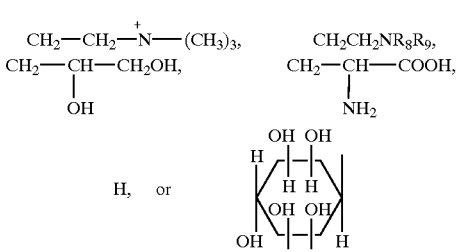

and $R_8$ and $R_9$ are independently hydrogen or lower alkyl.

17. The pharmaceutical compositions according to claim 14 wherein R is

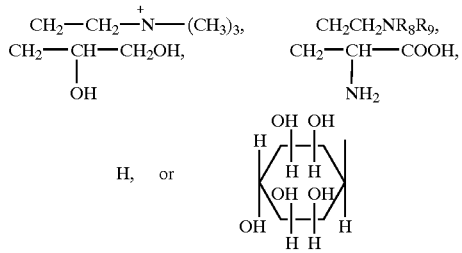

and $R_8$ and $R_9$ are independently hydrogen or lower alkyl.

18. The pharmaceutical compositions according to claim 11 wherein R is

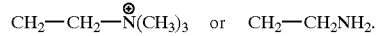

19. The pharmaceutical compositions according to claim 12 wherein R is

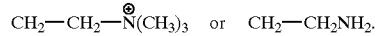

20. The pharmaceutical compositions according to claim 14 wherein R is

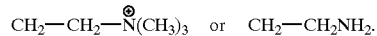

21. The pharmaceutical compositions according to claim 13 wherein R is $CH_2-CH_2-NH_2$.

22. The pharmaceutical compositions according to claim 14 wherein x is O.

23. The pharmaceutical compositions according to claim 12 wherein x is O.

24. The pharmaceutical compositions according to claim 13 wherein x is O.

25. The pharmaceutical compositions according to claim 14 wherein x is O.

26. The pharmaceutical compositions according to claim 11 wherein x+y=11.

27. The pharmaceutical compositions according to claim 12 wherein x+y=11.

28. The pharmaceutical compositions according to claim 13 wherein x+y=11.

29. The pharmaceutical compositions according to claim 14 wherein x+y=11.

30. The pharmaceutical compositions according to claim 12 wherein both x's are the same, both y's are the same and both Z's are the same.

31. The pharmaceutical compositions according to claim 12 wherein Z is O.

32. The pharmaceutical composition according to claim 1 wherein said compound has the formula:

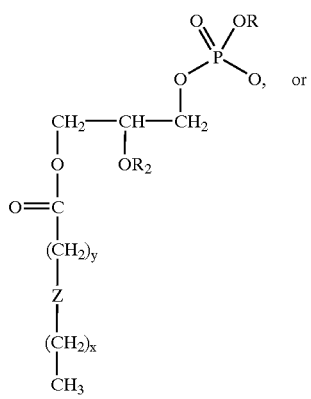

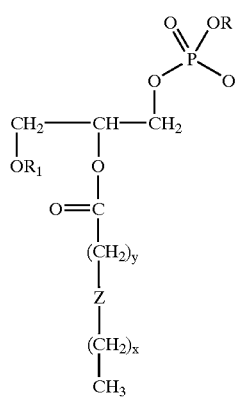

or pharmaceutically acceptable salts thereof wherein

R is a naturally occurring polar head group characteristic of a glycerophospholipid isolated from endogenous sources, $R_1$ and $R_2$ are independently hydrogen or an alkyl fatty acid acyl group having 4–26 carbon atoms, Z is S, x=0–13, and y=1–13 and x+y=11–13.

33. The pharmaceutical composition of claim 2 wherein said compound has the formula:

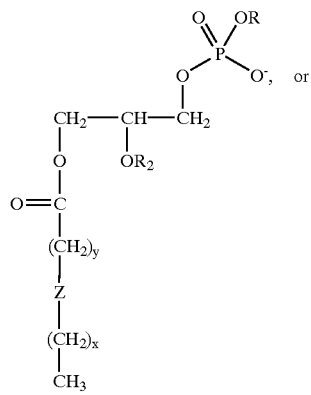

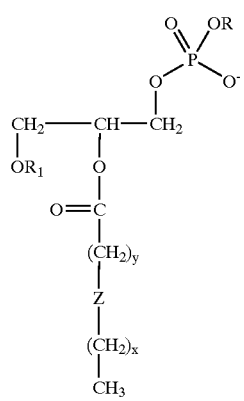

or pharmaceutically acceptable salts thereof wherein

R is a naturally occurring polar head group characteristic of a glycerophospholipid isolated from endogenous sources, $R_1$ and $R_2$ are hydrogen;

Z is O or S;

x=0–13;

y=1–13 and x+y=11–13.

34. The pharmaceutical composition of claim 3 wherein said compound is of the formula:

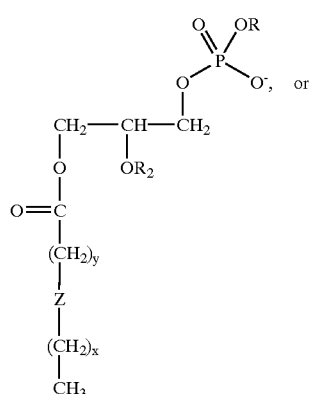

-continued

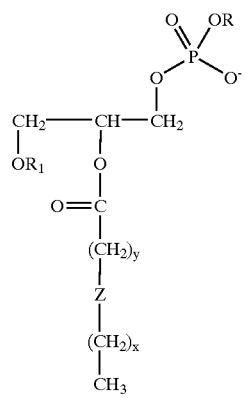

or pharmaceutically acceptable salts thereof wherein

R is

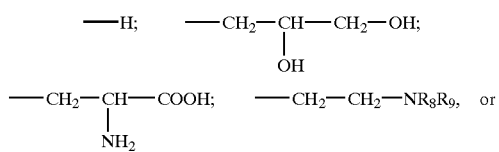

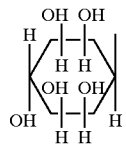

$R_8$ and $R_9$ are independently hydrogen or lower alkyl;

$R_1$ and $R_2$ are independently hydrogen or an alkyl fatty acid acyl group having 4–26 carbon atoms;

Z is O or S;

y=1–11 and x+y=13.

35. The pharmaceutical composition of claim 4 wherein said compound has the formula:

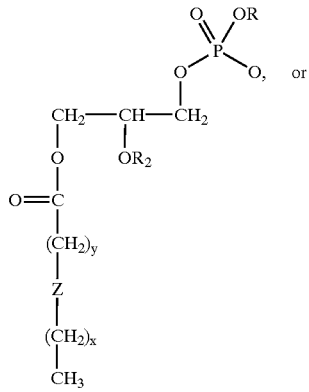

-continued

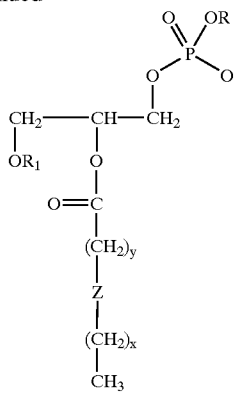

or pharmaceutically acceptable salts thereof wherein
R is a naturally occurring polar head group characteristic of a glycerophospholipid isolated from endogenous sources, $R_1$ and $R_2$ are independently hydrogen or an alkyl fatty acid acyl group having 4–26 carbon atoms;
Z is O or S;
x=4–13;
y=1–13;
x+y=13.

36. A pharmaceutical composition comprising a pharmaceutically effective amount of a compound of the formula:

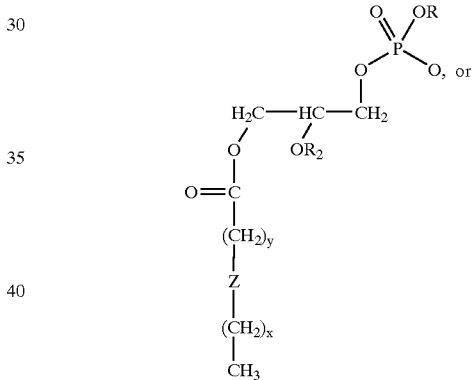

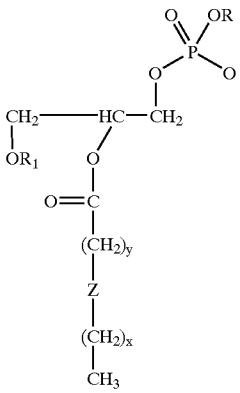

or pharmaceutically acceptable salts thereof and a pharmaceutical carrier therefor, wherein
R is a naturally occurring polar head group characteristic of a glycerophospholipid isolated from endogenous sources;

$R_1$ and $R_2$ are independently hydrogen or an alkyl fatty acid acyl group having 4–26 carbon atoms;

Z is S or O;

x is 0–13;

y=1–13; and x+y=11–13.

37. The pharmaceutical compositions according to claim 32 wherein $R_1$ and $R_2$ are independently hydrogen or fatty acid acyl group containing 4–8 carbon atoms.

38. The pharmaceutical compositions according to claim 33 wherein $R_1$ and $R_2$ are independently hydrogen or fatty acid acyl group containing 4–8 carbon atoms.

39. The pharmaceutical compositions according to claim 34 wherein $R_1$ and $R_2$ are independently hydrogen or fatty acid acyl group containing 4–8 carbon atoms.

40. The pharmaceutical compositions according to claim 35 wherein $R_1$ and $R_2$ are independently hydrogen or fatty acid acyl group containing 4–8 carbon atoms.

41. The pharmaceutical compositions according to claim 36 wherein $R_1$ and $R_2$ are independently hydrogen or fatty acid acyl group containing 4–8 carbon atoms.

42. The pharmaceutical compositions according to claim 33 wherein Z is O.

43. The pharmaceutical compositions according to claim 34 wherein Z is O.

44. The pharmaceutical compositions according to claim 35 wherein Z is O.

45. The pharmaceutical compositions according to claim 36 wherein Z is O.

46. The compounds according to claim 32 wherein R is

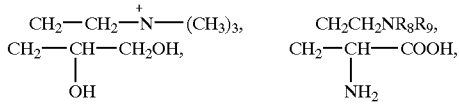

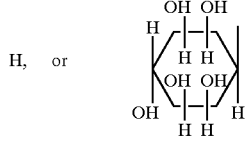

and $R_8$ and $R_9$ are independently hydrogen or lower alkyl.

47. The pharmaceutical compositions according to claim 33 wherein R is

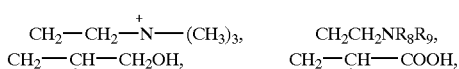

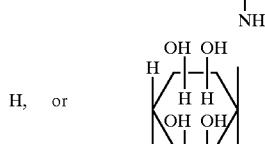

and $R_8$ and $R_9$ are independently hydrogen or lower alkyl.

48. The pharmaceutical composition according to claim 35 wherein R is

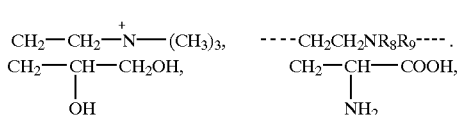

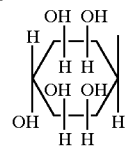

and $R_8$ and $R_9$ are independently hydrogen or lower alkyl.

49. The pharmaceutical compositions according to claim 36 wherein R is

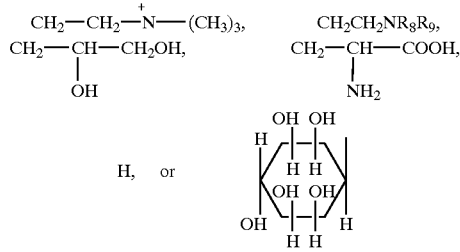

and $R_8$ and $R_9$ are independently hydrogen or lower alkyl.

50. The pharmaceutical compositions according to claim 32 wherein R is

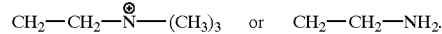

51. The pharmaceutical compositions according to claim 33 wherein R is

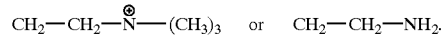

52. The pharmaceutical compositions according to claim 34 wherein R is $CH_2-CH_2-NH_2$.

53. The pharmaceutical compositions according to claim 35 wherein R is

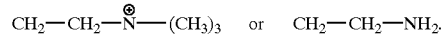

54. The pharmaceutical compositions according to claim 36 wherein R is

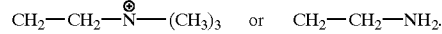

55. The pharmaceutical compositions according to claim 32 wherein x is O.

56. The pharmaceutical compositions according to claim 33 wherein x is O.

57. The pharmaceutical compositions according to claim 34 wherein x is O.

58. The pharmaceutical compositions according to claim 35 wherein x is O.

59. The pharmaceutical compositions according to claim 36 wherein x is O.

60. The pharmaceutical compositions according to claim 32 wherein x+y=11.

61. The pharmaceutical compositions according to claim 33 wherein x+y=11.

62. The pharmaceutical compositions according to claim 34 wherein x+y=11.

63. The pharmaceutical compositions according to claim 35 wherein x+y=11.

64. The pharmaceutical compositions according to claim 36 wherein x+y=11.

65. A compound having the formula:

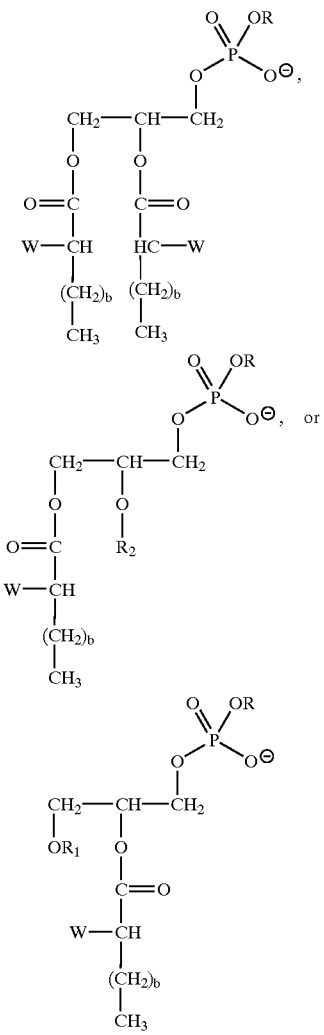

wherein each W is hydroxy or lower alkylthio;

each b is independently 11–13;

R is a naturally occurring polar head group characteristic of a glycerophospholipid isolated from endogenous sources;

$R_1$ and $R_2$ are independently hydrogen or an alkyl fatty acid acyl group having 4–26 carbon atoms.

66. The compound according to claim 62 wherein R is

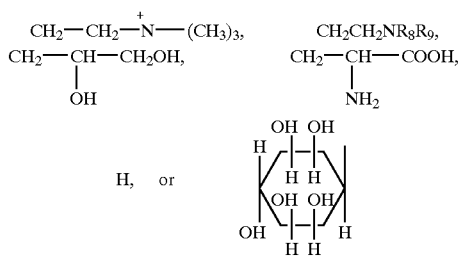

and $R_8$ and $R_9$ are independently hydrogen or lower alkyl.

67. The compound according to claim 65 wherein each b is 11.

68. The compound according to claim 65 wherein R is

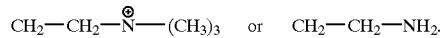

69. The compound according to claim 66 wherein $R_7$ is an alkyl group containing 3–7 or 13 carbon atoms.

70. AC1 or the D or L stereoisomer thereof.

71. AC2 or the D or L stereoisomer thereof.

72. 1-(12 methoxy dodecanoyl)-sn-3-glycerophosphatidyl choline or the D or L stereoisomers thereof.

73. A compound of the formula which is:

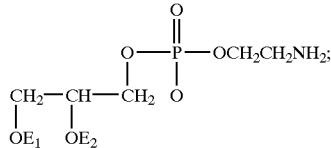

or pharmaceutically acceptable salts thereof wherein $E_1$ is myristoyl or 12-methoxydodecanoyl and $E_2$ is 12-methoxydodecanyl.

74. The D stereoisomer of claim 73.

75. The L stereoisomer of claim 74.

76. A method for the inhibition of protein myristoylation in an animal in need thereof comprising administering to said animal an effective amount of a compound according to any one of claims 11–14, 32–36 or 65–76.

77. A method for the inhibition of retroviral proliferation in an animal in need thereof comprising administering to said animal a retroviral proliferation inhibiting amount of the compound according to any one of claims 11–14, 32–36 or 65–76.

78. A pharmaceutical composition suitable for administration to an animal in need thereof comprising a pharmaceutically acceptable carrier and a pharmaceutically effective amount of a compound according to any one of claims 1–4, 11–14, 32–36 or 65–76.

79. The pharmaceutical composition according to any one of claims 2–4 wherein $E_1$ or $E_2$ is

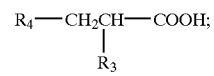

wherein $R_3$ is hydrogen or lower alkyl;

$R_4$ is $R_5$—Z—$R_6$;

Z is O or S;

$R_5$ and $R_6$ are independently an alkyl group containing from 1–18 carbon atoms in the principal chain and up to a total of 23 carbon atoms, such that the sum of the number of carbon atoms in $R_3$ and $R_4$ is no greater than 23.

80. The pharmaceutical compositions according to claim 79 wherein $R_3$ is hydrogen.

81. The pharmaceutical compositions according to claim 79 wherein $R_3$ is hydrogen and $R_5$ and $R_6$ are a straight chain.

82. The pharmaceutical compositions according to claim 81 wherein the sum of the carbon atoms in $R_5$ and $R_6$ is 10–11.

83. The pharmaceutical compositions according to claim 1 wherein $R_6$ is $CH_3$.

84. The compound according to claim 9 wherein $R_1$ and $R_2$ are independently an alkyl fatty acid acyl group having 12–16 carbon atoms.

85. The compound according to claim 32 wherein $R_1$ and $R_2$ are independently hydrogen or fatty acid acyl group containing 13–15 carbon atoms.

86. The compound according to claim 33 wherein $R_1$ and $R_2$ are independently hydrogen or fatty acid acyl group containing 13–15 carbon atoms.

87. The compound according to claim 34 wherein $R_1$ and $R_2$ are independently hydrogen or fatty acid acyl group containing 13–15 carbon atoms.

88. The compound according to claim 35 wherein $R_1$ and $R_2$ are independently hydrogen or fatty acid acyl group containing 13–15 carbon atoms.

89. The compound according to claim 36 wherein $R_1$ and $R_2$ are independently hydrogen or fatty acid acyl group containing 13–15 carbon atoms.

90. A method for the inhibition of protein myristoylation in an animal in need thereof comprising administering to said animal a protein myristoylating inhibiting effective amount of a compound of the formula:

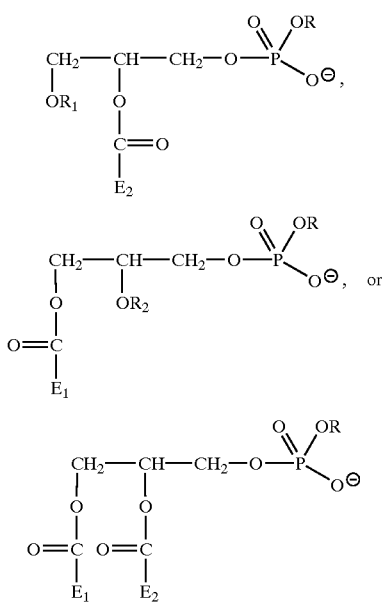

wherein

R is a naturally occurring polar head group characteristic of a glycerophospholipid isolated from endogenous sources;

$R_1$ and $R_2$ are independently hydrogen or an alkyl fatty acid acyl group having 4–26 carbon atoms, and $E_1$ and $E_2$ are independently a heteroatom hydrocarbyl group having 3–25 carbon atoms, wherein at least one of the carbon atoms in the principal chain is replaced by O or S, and wherein such substitution does not occur on the α-carbon to the acyl group or on the omega carbon.

91. The method according to claim 90 wherein the compound has the formula

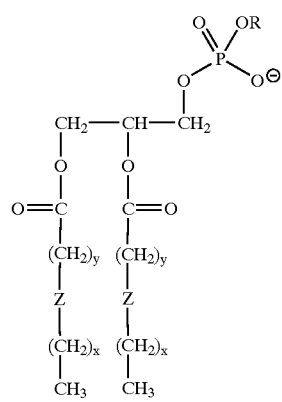

wherein

R is a naturally occurring polar head group characteristic of a glycerophospholipid isolated from endogenous sources;

each Z is independently O or S;

each x may be the same or different and x=0–13;

each y may be the same or different y=1–13 and x+y= 11–15.

92. The method according to claim 90 having the formula

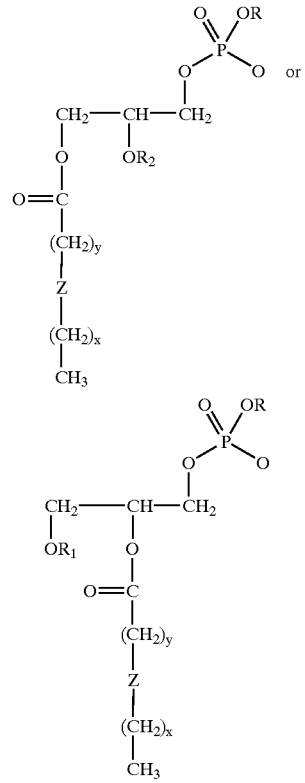

wherein R is a naturally occurring polar head group characteristic of a glycerophospholipid isolated from endogenous sources;

$R_1$ and $R_2$ are independently hydrogen or an alkyl fatty acid group having 4–26 carbon atoms;

Z is O or S;

x=0–13; and y=1–13 and x+y=11–13.

93. The method according to claim 90 wherein the compound has the formula:

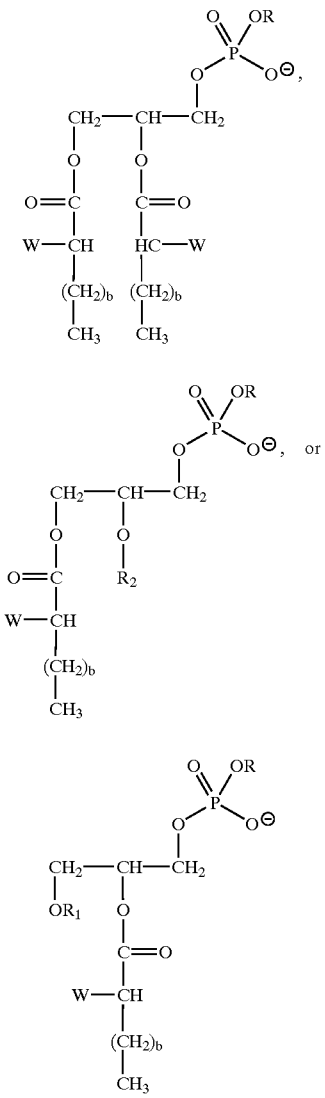

wherein each W is independently hydroxy, halo, alkoxy, mercapto or alkylthio;

each b is independently 11–13;

$R_1$ and $R_2$ are independently hydrogen or alkyl fatty acid acyl group having 4–26 carbon atoms; and R is a naturally occurring polar head group characteristic of a glycerophospholipid Isolated from endogenous sources.

94. The method according to any one of claims 90–93 wherein R is

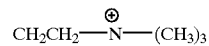 

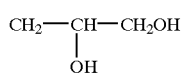 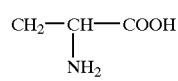

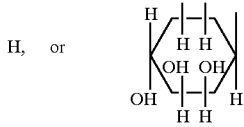

wherein $R_8$ and $R_9$ are independently hydrogen or lower alkyl.

95. A method for the inhibition of retroviral proliferation in an animal in need thereof comprising administering to said animal a retroviral proliferation inhibiting amount of a compound of the formula

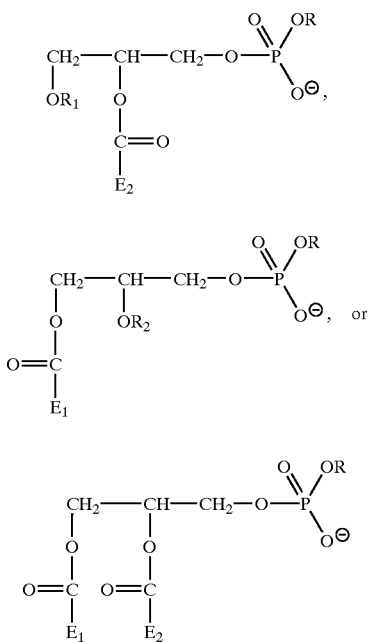

wherein

R is a naturally occurring polar head group characteristic of a glycerophospholipid isolated from endogenous sources;

$R_1$ and $R_2$ are independently hydrogen or an alkyl fatty acid acyl group having 4–26 carbon atoms, and $E_1$ and $E_2$ are independently a heteroatom hydrocarbyl group having 3–25 carbon atoms, wherein at least one of the carbon atoms in the principal chain is replaced by O or S and such substitution does not occur on the α-carbon to the acyl group or on the omega carbon.

96. The method according to claim 95 wherein the compound has the formula

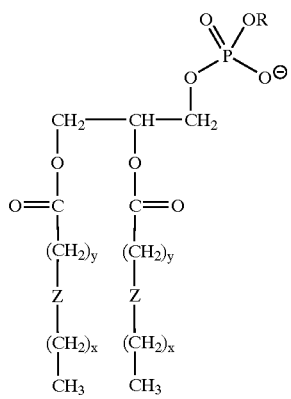

wherein
R is a naturally occurring polar head group characteristic of a glycerophospholipid isolated from endogenous sources;
each Z is independently O or S;
each x may be the same or different and x=0–13;
each y may be the same or different and y=1–13 and x+y=11–15.

97. The method according to claim 95 having the formula

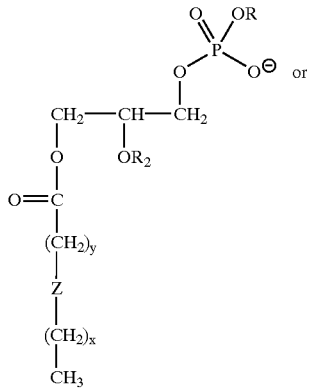 or

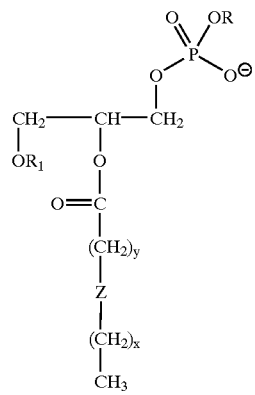

wherein R is a naturally occurring polar head group characteristic of a glycerophospholipid isolated from endogenous sources;
$R_1$ and $R_2$ are independently hydrogen or an alkyl fatty acid acyl group having 4–26 carbon atoms;
Z is O or S;
x=0–13; and
y=1–13 and x+y=11–13.

98. The method according to claim 95 wherein the compound has the formula:

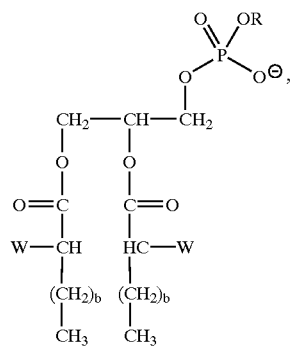

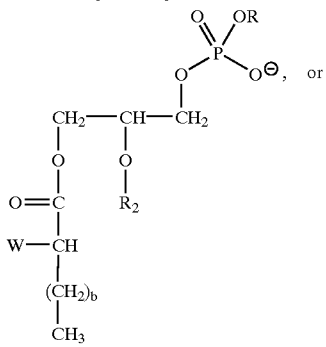 or

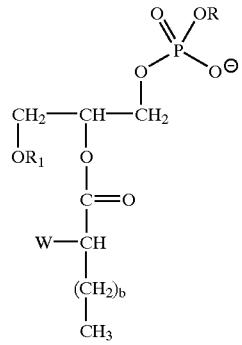

wherein each W is independently hydroxy, halo, alkoxy, mercapto, or alkylthio;
each b is independently 11–13;
$R_1$ and $R_2$ are independently hydrogen or alkyl fatty acid acyl group having 4–26 carbon atoms; and
R is a naturally occurring polar head group characteristic of a glycerophospholipid isolated from endogenous sources.

99. The method according to any one of claims 95–98 wherein R is

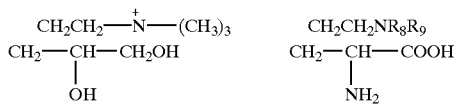

H, or 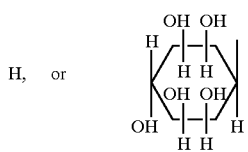

wherein $R_8$ and $R_9$ are independently hydrogen or lower alkyl.

100. The method according to claim 84 wherein the compound is of the formula:

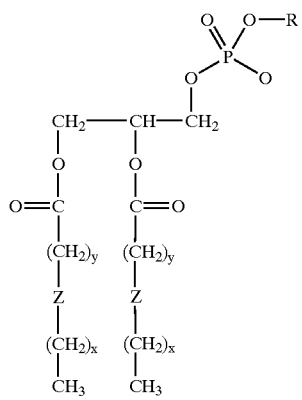

or pharmaceutically acceptable salts thereof wherein

R is a naturally occurring polar head group characteristic of a glycerophospholipid isolated from endogenous sources, one Z is S and the other is O or S;

each x may be the same or different and x=0–13, and each y may be the same or different and y=1–13, and x+y=11–15.

101. The method according to claim 84 wherein the compound is of the formula:

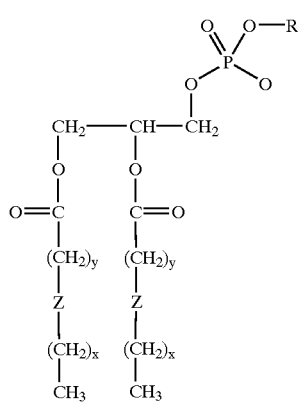

or pharmaceutically acceptable salts thereof wherein

R is a naturally occurring polar head group characteristic of a glycerophospholipid isolated from endogenous sources, both Z's are the same or different and are O or S, each x may be the same or different and x=0–13, each y may be the same or different and y=1–13 and x+y=11–15.

102. The method according to claim 84 wherein the compound is of the formula:

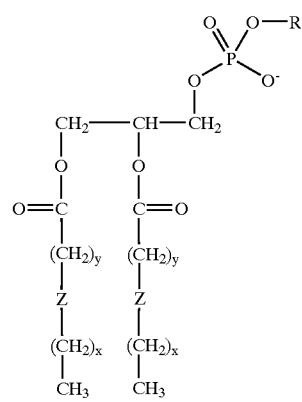

or pharmaceutically acceptable salts thereof wherein
each Z is independently O or S
R is

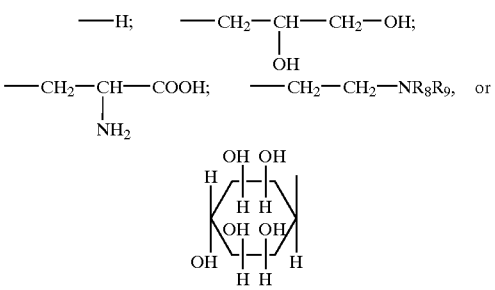

$R_8$ and $R_9$ are independently hydrogen or lower alkyl, each x may be the same or different and x=0–13, each y may be the same or different and y=1–13 and x+Y=11–15.

103. The method according to claim 84 wherein the compound is of the formula:

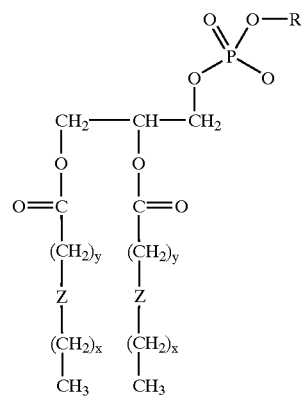

or pharmaceutically acceptable salts thereof wherein

R is a naturally occurring polar head group characteristic of a glycerophospholipid isolated from endogenous sources, each x may be the same or different, and x=4–13, each y may be the same or different, each y=1–13, and x+y=11–15, and Z is independently O or S.

104. The method according to claim 84 wherein the compound is of the formula:

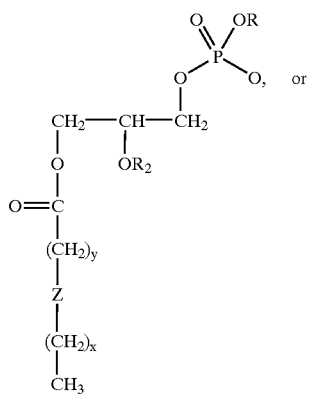

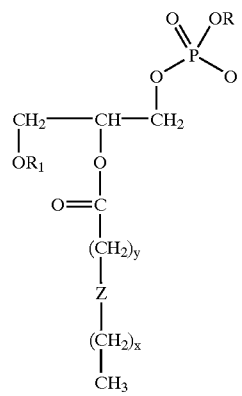

or pharmaceutically acceptable salts thereof wherein

R is a naturally occurring polar head group characteristic of a glycerophospholipid isolated from endogenous sources, $R_1$ and $R_2$ are independently hydrogen or an alkyl fatty acid acyl group having 4–26 carbon atoms, Z is S, x=0–13, and y=1–13 and x+y=11–13.

105. The method according to claim 84 wherein the compound is of the formula:

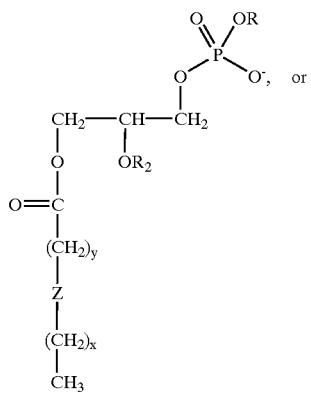

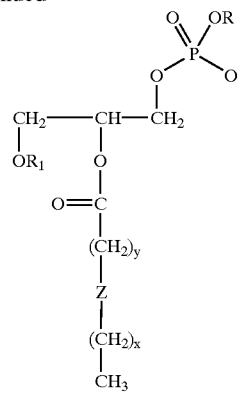

or pharmaceutically acceptable salts thereof wherein

R is a naturally occurring polar head group characteristic of a glycerophospholipid isolated from endogenous sources, $R_1$ and $R_2$ are hydrogen;

Z is O or S;

x=0–13;

y=1–13 and x+y=11–13.

106. The method according to claim 84 wherein the compound is of the formula:

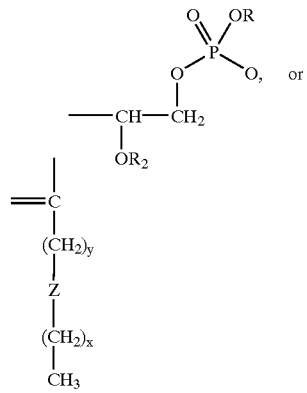

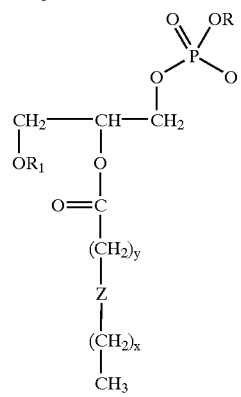

or pharmaceutically acceptable salts thereof wherein

R is

—H;  —CH$_2$—CH—CH$_2$—OH;
              |
              OH

-continued

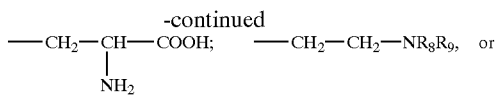

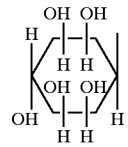

$R_8$ and $R_9$ are independently hydrogen or lower alkyl;

$R_1$ and $R_2$ are independently hydrogen or an alkyl fatty acid acyl group having 4–26 carbon atoms;

Z is O or S;

x=0–13;

y=1–11 and x+y=13.

107. The method according to claim 84 wherein the compound is of the formula:

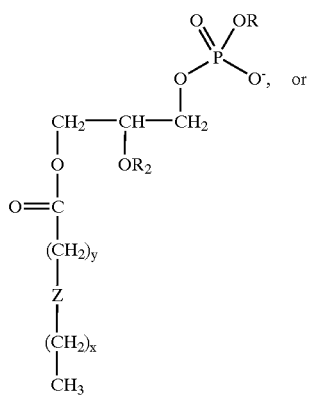

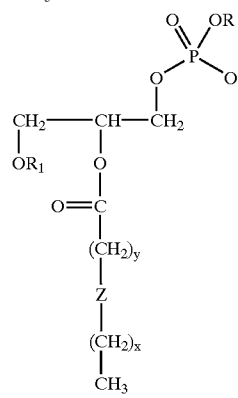

or pharmaceutically acceptable salts thereof wherein

R is a naturally occurring polar head group characteristic of a glycerophospholipid isolated from endogenous sources, $R_1$ and $R_2$ are independently hydrogen or an alkyl fatty acid acyl group having 4–26 carbon atoms;

Z is O or S;

x=4–13;

y=1–13;

x+y=13.

108. The method according to claim 84 wherein the compound is of the formula:

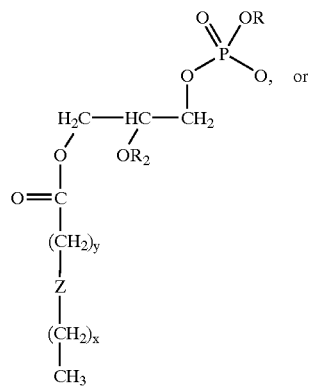

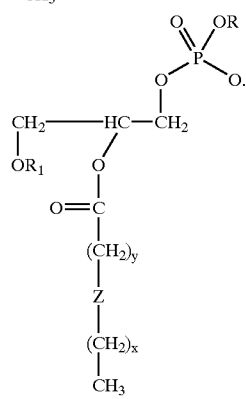

or pharmaceutically acceptable salts thereof

R is a naturally occurring polar head group characteristic of a glycerophospholipid isolated from endogenous sources;

$R_1$ and $R_2$ are independently hydrogen or an alkyl fatty acid acyl group having 4–26 carbon atoms;

Z is S or O;

x is 0–13;

y=1–13; and x+y=11–13.

109. The method according to claim 95 wherein the compound is of the formula:

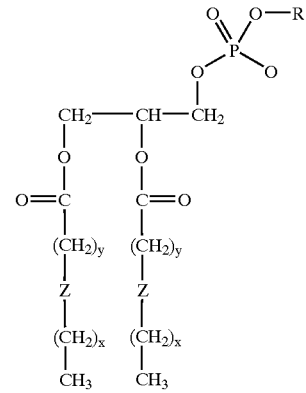

or pharmaceutically acceptable salts thereof wherein

R is a naturally occurring polar head group characteristic of a glycerophospholipid isolated from endogenous sources, one Z is S and the other is O or S;

each x may be the same or different and x=0–13, and each y may be the same or different and y=1–13, and x+y=11–15.

110. The method according to claim 95 wherein the compound is of the formula:

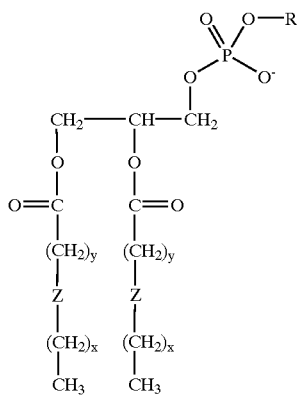

or pharmaceutically acceptable salts thereof wherein
R is a naturally occurring polar head group characteristic of a glycerophospholipid isolated from endogenous sources, both Z's are the same or different and are O or S,
each x may be the same or different and x=0–13,
each y may be the same or different and y=1–13 and x+y=11–15.

111. The method according to claim 95 wherein the compound is of the formula:

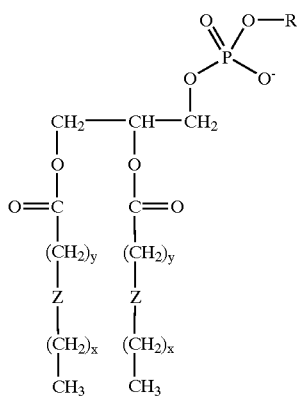

or pharmaceutically acceptable salts thereof wherein
each Z is independently O or S
R is

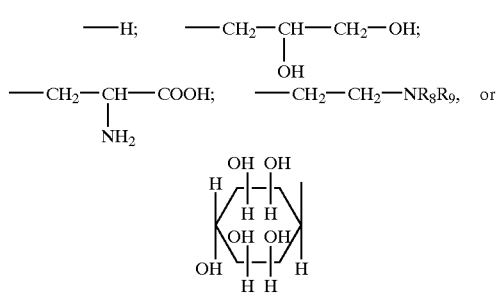

$R_8$ and $R_9$ are independently hydrogen or lower alkyl,
each x may be the same or different and x=0–13, each y may be the same or different and y=1–13 and x+Y=11–15.

112. The method according to claim 95 wherein the compound is of the formula:

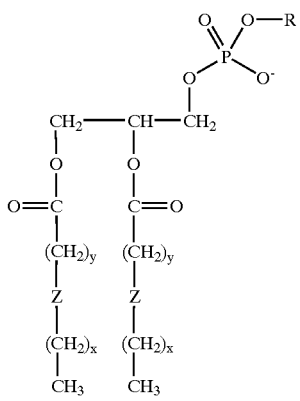

or pharmaceutically acceptable salts thereof wherein
R is a naturally occurring polar head group characteristic of a glycerophospholipid isolated from endogenous sources,
each x may be the same or different, and x=4–13,
each y may be the same or different, each y=1–13, and x+y=11–15, and Z is independently O or S.

113. The method according to claim 95 wherein the compound is of the formula:

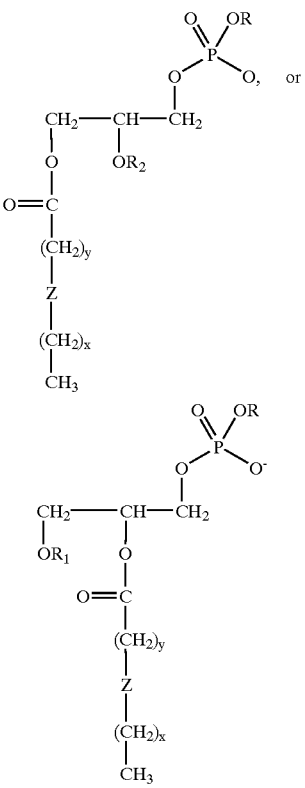

or pharmaceutically acceptable salts thereof wherein
R is a naturally occurring polar head group characteristic of a glycerophospholipid isolated from endogenous sources,
$R_1$ and $R_2$ are independently hydrogen or an alkyl fatty acid acyl group having 4–26 carbon atoms, Z is S, x=0–13, and y=1–13 and x+y=11–13.

114. The method according to claim 95 wherein the compound is of the formula:

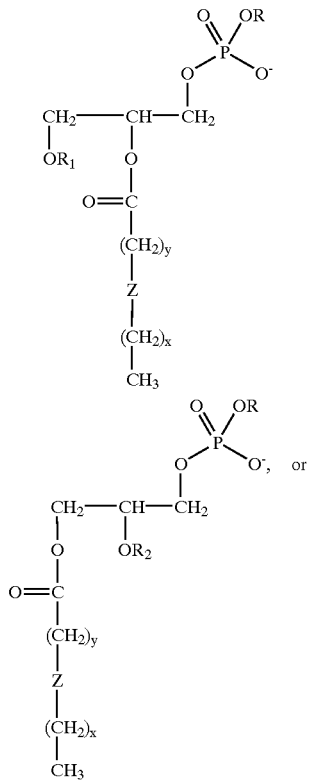

or pharmaceutically acceptable salts thereof wherein

R is a naturally occurring polar head group characteristic of a glycerophospholipid isolated from endogenous sources, $R_1$ and $R_2$ are hydrogen;

Z is O or S;

x=0–13;

y=1–13 and x+y=11–13.

115. The method according to claim 95 wherein the compound is of the formula:

or pharmaceutically acceptable salts thereof wherein

R is $R_8$ and $R_9$ are independently hydrogen or lower alkyl;

$R_1$ and $R_2$ are independently hydrogen or an alkyl fatty acid acyl group having 4–26 carbon atoms;

Z is O or S;

x=0–13 y=1–11 and x+y=13.

116. The method according to claim 95 wherein the compounds is of the formula:

-continued

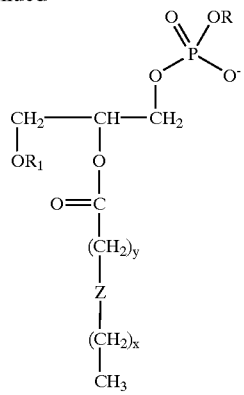

or pharmaceutically acceptable salts thereof wherein
R is a naturally occurring polar head group characteristic of a glycerophospholipid isolated from endogenous sources, R, and R, are independently hydrogen or an alkyl fatty acid acyl group having 4–26 carbon atoms;
Z is O or S;
x=4–13;
y=1–13;
x+y=13.

117. The method according to claim 95 wherein the compound is of the formula:

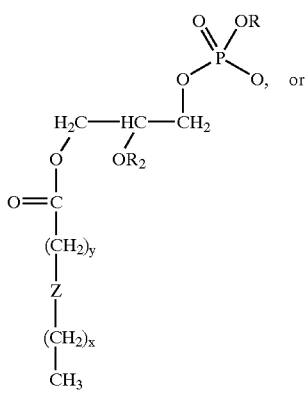

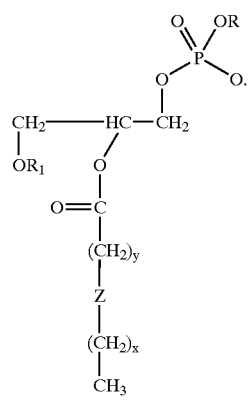

or pharmaceutically acceptable salts thereof
R is a naturally occurring polar head group characteristic of a glycerophospholipid isolated from endogenous sources;
$R_1$ and $R_2$ are independently hydrogen or an alkyl fatty acid acyl group having 4–26 carbon atoms;

Z is S or O;
x is 0–13;
y=1–13; and
x+y=11–13.

118. A compound having the formula:

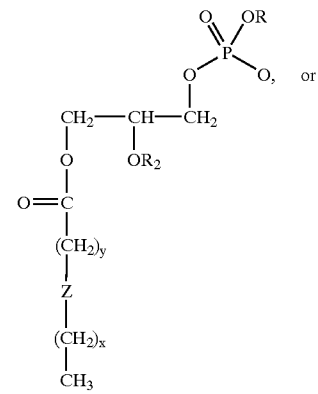

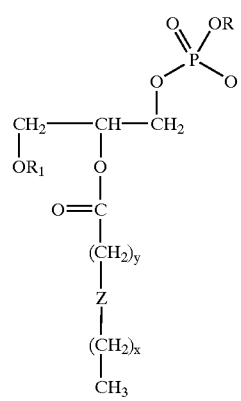

or pharmaceutically acceptable salts thereof wherein

R is a naturally occurring polar head group characteristic of a glycerophospholipid isolated from endogenous sources, $R_1$ and $R_2$ are independently hydrogen or an alkyl fatty acid acyl group having 4–26 carbon atoms, Z is S, x=0–13, and y=1–13 and x+y=11–13.

119. The compound according to claim 32 wherein $R_1$ and $R_2$ are independently hydrogen or fatty acyl group containing 4–8 carbon atoms.

120. The compound according to claim 32 wherein R is $CH_2$—$CH_2$—$\overset{+}{N}$—$(CH_3)_3$,     $CH_2$—$CH_2$—$NR_8R_9$, $CH_2$—$\underset{OH}{CH}$—$CH_2OH$,     $CH_2$—$\underset{NH_2}{CH}$—$COOH$, -continued H, or [cyclohexane ring with OH, OH, H, H, OH, OH, OH, H, H, H substituents]

and $R_8$ and $R_9$ are independently hydrogen or loweralkyl.

121. The compound according to claim 32 wherein R is $$CH_2-CH_2-\overset{\oplus}{N}-(CH_3)_3 \quad \text{or} \quad CH_2-CH_2-NH_2.$$

122. The compound according to claim 32 wherein x is 0.
123. The compound according to claim 32 wherein x+y is 11.

\* \* \* \* \*